(12) United States Patent
Dewdney et al.

(10) Patent No.: US 7,943,618 B2
(45) Date of Patent: *May 17, 2011

(54) BTK PROTEIN KINASE INHIBITORS

(75) Inventors: Nolan James Dewdney, Saratoga, CA (US); Rama K. Kondru, Sunnyvale, CA (US); Yan Lou, San Jose, CA (US); Michael Soth, Milpitas, CA (US); Tobias Gabriel, Basel (CH)

(73) Assignee: Roche Palo Alto LLC, South San Frnacisco, CA (US)

( * ) Notice: Subject to any disclaimer, the term of this patent is extended or adjusted under 35 U.S.C. 154(b) by 7 days.

This patent is subject to a terminal disclaimer.

(21) Appl. No.: 12/288,730

(22) Filed: Oct. 23, 2008

(65) Prior Publication Data

US 2009/0105209 A1 Apr. 23, 2009

Related U.S. Application Data

(60) Provisional application No. 61/000,139, filed on Oct. 23, 2007, provisional application No. 61/086,416, filed on Aug. 5, 2008.

(51) Int. Cl.
*A61K 31/50* (2006.01)

(52) U.S. Cl. .................................. 514/252.01; 544/239

(58) Field of Classification Search .................... 544/239
See application file for complete search history.

(56) References Cited

U.S. PATENT DOCUMENTS

| 2008/0103142 A1 | 5/2008 | Goldstein et al. |
| 2008/0146565 A1 | 6/2008 | Dunn et al. |

FOREIGN PATENT DOCUMENTS

| WO | WO 2006/053121 A2 | 5/2006 |
| WO | WO 2006/053121 A3 | 5/2006 |
| WO | WO 2006/076592 A1 | 7/2006 |
| WO | WO 2006/099075 A2 | 9/2006 |
| WO | WO 2006/099075 A3 | 9/2006 |
| WO | WO 2007/-027528 A2 | 3/2007 |
| WO | WO 2007/-027528 A3 | 3/2007 |
| WO | WO 2007/027729 A1 | 3/2007 |
| WO | WO 2008/-033834 A1 | 3/2008 |
| WO | WO 2008/-033854 A1 | 3/2008 |
| WO | WO 2008/-033857 A2 | 3/2008 |
| WO | WO 2008/-033857 A3 | 3/2008 |
| WO | WO 2008/-033858 A2 | 3/2008 |
| WO | WO 2008/-033858 A3 | 3/2008 |

OTHER PUBLICATIONS

Antonyak, M.A., et. al. "Elevated JNK activation contributes to the pathogenesis of human brain tumors," *Oncogene*, 2002, vol. 21, pp. 5038-5046.
Bennett, B. L., et. al. "JNK: a new therapeutic target for diabetes," *Current Opinion in Pharmacology*, 2003, vol. 3, pp. 420-425.
Blease, K., et. al. "Emerging Treatments for Asthma," *Expert Opinion Emerg. Drugs*, 2003, vol. 8, pp. 71-81.
Bousquet, J., et. al. "Asthma: From Bronchoconstriction to Airways Inflammation and Remodeling," *Am. J. Respir. Crit. Cam Med.*, 2000, vol. 161, pp. 1720-1745.
Bozyczko-Coyne, D., et. al. "Targeting the JNK Pathway for Therapeutic Benefit in CNS Disease," *Current Drug Targets*, 2002, vol. 1, pp. 31-49.
Bradley, B.L.., et. al. "Eosinophils, T-lymphocytes, mast cells, neutrophils, and macrophages in bronchial biopsy specimens from atopic subjects with asthma: Comparison with biopsy specimens from atopic subjects without asthma and normal control subjects and relationship to bronchial hyperresponsiveness," *J. Allergy Clin. Immunology*, 1991, vol. 88, pp. 661-674.
Cripe, L.D., "Role for c-jun N-terminal kinase in treatment-refractory acute myeloid leukemia (AML): signaling to multidrug-efflux and hyperproliferation," *Leukemia*, 2002, vol. 16, pp. 799-812.
Derijard, B., et. al. "JNK1: A Protein Kinase Stimulated by UV Light and Ha-Ras That Binds and Phosphorylates the c-Jun Activation Domain," *Cell*, 1994, vol. 76, pp. 1025-1037.
Eynott, P. R., et. al. "Allergen-induced inflammation and airway epithelial and smooth muscle cell proliferation: role of Jun N-terminal kinase," *British Journal of Pharmacology*, 2003, vol. 140, pp. 1373-1380. Gaillard, P., et. al. "Design and Synthesis of the First Generation of Novel Potent, Selective, and in Vivo Active (Benzothiazol-2-yl) acetonitrile Inhibitors of the c-Jun N-Terminal," *Journal of Medicinal Chem.* 2005, vol. 48, pp. 4596-4607.
Han, Z., et. al. "Joint Damage and Inflammation in c-Jun N-Terminal Kinase 2 Knockout Mice with Passive Murine Collagen-Induced Arthritis," *Arthritis & Rheumatism*, 2002, vol. 46 (3), pp. 818-823.
Han, Z., et. al. "c-Jun N-terminal kinase is required for metalloproteinase expression and joint destruction in inflammatory arthritis," *J. Clinical Invest.*, 2001, vol. 108 (1), pp. 73-81.
Hess, P., et. al. "Survival signaling mediated by c-Jun $NH_2$-terminal kinase in transformed B lymphoblasts," *Nature Genetics* 2002, vol. 32, pp. 201-205.
Hirosumi, J., et. al. "A Central role for JNK in obesity and insulin resistance," *Nature* 2002, vol. 420, pp. 333-336.

(Continued)

*Primary Examiner* — Brian McDowell
(74) *Attorney, Agent, or Firm* — Brian L. Buckwalter

(57) ABSTRACT

This application discloses pyridine and pyrimidine compounds according to formula I wherein $R^1$,

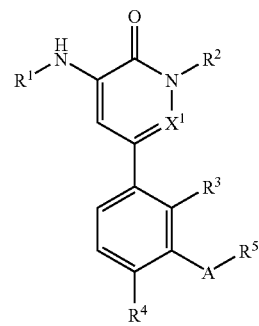

(I)

$R^2$, $R^3$, $R^4$, $R^5$, $X^1$ and A are as described herein which inhibit Btk. The compounds disclosed herein are useful to modulate the activity of Btk and treat diseases associated with excessive Btk activity. The compounds are further useful to treat inflammatory and auto immune diseases associated with aberrant B-cell proliferation such as rheumatoid arthritis. Also disclosed are compositions containing compounds of formula I and at least one carrier, diluent or excipient.

8 Claims, No Drawings

OTHER PUBLICATIONS

Ip, Y. T., et. al. "Signal transduction by the c-Jun N-terminal kinase (JNK) —from inflammation to development," *Current Opinion Cell. Biology* 1998, vol. 10, pp. 205-219.

Jaeschke, A., et. al. "Disruption of the Jnk2 (Mapk9) gene reduces destructive insulitis and diabetes in a mouse model of type I diabetes," *PNAS* 2005, vol. 102 (19), pp. 6931-6935.

Kaneto, H., et. al. "Possible novel therapy for diabetes with cell-permable JNK-inhibitory peptide," *Nature Medicine*, 2004, vol. 10 (10), pp. 1128-1132.

Kaneto, H., et. al. "The JNK pathway as a therapeutic target for diabetes," *Expert Opinion*, 2005, vol. 9 (3), pp. 581-592.

Kujime, K., et. al. "p38 Mitogen-Activated Protein Kinase and c-Jun-NH2-Terminal Kinase Regulate RANTES Production by Influenza Virus-Infected Human Bronchial Epithelial Cells[1]," *The Journal of Immunology* 2000, vol. 164, pp. 3222-3228.

Lee, Y.H., et. al. "c-Jun N-terminal Kinase (JNK) Mediates Feedback Inhibition of the Insulin Signaling Cascade*," *The Journal of Biological Chemistry* 2003, vol. 278 (5), pp. 2896-2902.

Manning, A.M., et. al. "Targeting JNK for Therapeutic Benefit: From Junk to Gold?" *Nature* 2003, vol. 2, pp. 554-565.

Nakatani, Y., et. al. "Modulation of the JNK Pathway in Liver Affects Insulin Resistance Status*," *The Journal of Biological Chemistry* 2004, vol. 279 (44), pp. 45803-45809.

Nath, P., et. al. "Potential role of c-Jun NH2-terminal kinase in allergic airway inflammation and remodeling: effects of SP600125," *European Journal of Pharmacology* 2005, vol. 506, pp. 273-283.

Pei, J., et. al. "Localization of active forms of C-jun kinase (JNK) and p38 kinase in Alzeheimer's disease brains at different stages of neurofibrillary degeneration," *Journal of Alzheimer's Disease* 2001, vol. 3, pp. 41-48.

Saporito, M., et. al. "MPTP Activates c-Jun NH2-Terminal Kinase (JNK) and Its Upstream Regulatory Kinase MKK4 in Nigrostriatal Neurons in Vivo," *Journal of Neurochemistry* 2000, vol. 75, pp. 1200-1208.

Schett, G., et. al. "Activation, Differential Localization, and Regulation of the Stress-Activated Protein Kinases, Extracellular Signal-Regulated Kinase, c-Jun N-Terminal Kinase, and p38 Mitogen-Activated Protein Kinase, in Synovial Tissue and Cells in Rheumatoid Arthritis, "*Arthritis & Rheumatism* 2000, vol. 43 (11), pp. 2501-2512.

Sundarrajan, M., et. al. "Expression of the MAPK Kinases MKK-4 and MKK-7 in Rheumatoid Arthritis and Their Role as Key Regulators of JNK," *Arthritis & Rheumatism* 2003, vol. 48 (9), pp. 2450-2460.

Xia, X., et. al. "Gene transfer of the JNK interacting protein-1 protects dopaminergic neurons in the MPTP model of Parkinson's disease," *PNAS* 2001, vol. 98 (18), pp. 10433-10438.

Yang, D.D., et. al. "Absence of excitotoxicity-induced apoptosis in the hippocampus of mice lacking the JNK3 gene," *Nature* 1997, vol. 389, pp. 865-870.

Yasuda, J., et. al "The JIP Group of Mitogen-Activated Protein Kinase Scaffold Proteins," *Molecular and Cellular Biology* 1999, vol. 19 (10), pp. 7245-7254.

BTK PROTEIN KINASE INHIBITORS

CROSS REFERENCE TO PRIOR APPLICATIONS

This application claims the benefit of priority to U.S. Ser. No. 61/000,139 filed Oct. 23, 2007 and 61/086,416 filed Aug. 5, 2008, both of which are hereby incorporated in their entirety by reference.

FIELD OF THE INVENTION

The present invention relates to the use of novel pyrimidine and pyridine derivatives which inhibit Btk and are useful for the treatment of auto-immune and inflammatory diseases caused by aberrant B-cell activation. The novel pyrimidine and pyridine derivatives described herein are useful for the treatment of arthritis.

BACKGROUND OF THE INVENTION

Protein kinases constitute one of the largest families of human enzymes and regulate many different signaling processes by adding phosphate groups to proteins (T. Hunter, Cell 1987 50:823-829). Specifically, tyrosine kinases phosphorylate proteins on the phenolic moiety of tyrosine residues. The tyrosine kinase family includes members that control cell growth, migration, and differentiation. Abnormal kinase activity has been implicated in a variety of human diseases including cancers, autoimmune and inflammatory diseases. Since protein kinases are among the key regulators of cell signaling they provide a target to modulate cellular function with small molecular kinase inhibitors and thus make good drug design targets. In addition to treatment of kinase-mediated disease processes, selective and efficacious inhibitors of kinase activity are also useful for investigation of cell signaling processes and identification of other cellular targets of therapeutic interest.

There is good evidence that B-cells play a key role in the pathogenesis of autoimmune and/or inflammatory disease. Protein-based therapeutics that deplete B cells such as Rituxan are effective against autoantibody-driven inflammatory diseases such as rheumatoid arthritis (Rastetter et al. Annu Rev Med 2004 55:477). Therefore inhibitors of the protein kinases that play a role in B-cell activation should be useful therapeutics for B-cell mediated disease pathology such as autoantibody production.

Signaling through the B-cell receptor (BCR) controls a range of B-cell responses including proliferation and differentiation into mature antibody producing cells. The BCR is a key regulatory point for B-cell activity and aberrant signaling can cause deregulated B-cell proliferation and formation of pathogenic autoantibodies that lead to multiple autoimmune and/or inflammatory diseases. Bruton's Tyrosine Kinase (Btk) is a non-BCR associated kinase that is membrane proximal and immediately downstream from BCR. Lack of Btk has been shown to block BCR signaling and therefore inhibition of Btk could be a useful therapeutic approach to block B-cell mediated disease processes.

Btk is a member of the Tec family of tyrosine kinases, and has been shown to be a critical regulator of early B-cell development and mature B-cell activation and survival (Khan et al. Immunity 1995 3:283; Ellmeier et al. J. Exp. Med. 2000 192:1611). Mutation of Btk in humans leads to the condition X-linked agammaglobulinemia (XLA) (reviewed in Rosen et al. New Eng. J. Med. 1995 333:431 and Lindvall et al. Immunol. Rev. 2005 203:200). These patients are immunocompromised and show impaired maturation of B-cells, decreased immunoglobulin and peripheral B-cell levels, diminished T-cell independent immune responses as well as attenuated calcium mobilization following BCR stimulation.

Evidence for a role for Btk in autoimmune and inflammatory diseases has also been provided by Btk-deficient mouse models. In preclinical murine models of systemic lupus erythematosus (SLE), Btk-deficient mice show marked amelioration of disease progression. In addition, Btk-deficient mice are resistant to collagen-induced arthritis (Jansson and Holmdahl Clin. Exp. Immunol. 1993 94:459). A selective Btk inhibitor has been demonstrated dose-dependent efficacy in a mouse arthritis model (Z. Pan et al., Chem. Med Chem. 2007 2:58-61).

Btk is also expressed by cells other than B-cells that may be involved in disease processes. For example, Btk is expressed by mast cells and Btk-deficient bone marrow derived mast cells demonstrate impaired antigen induced degranulation (Iwaki et al. J. Biol. Chem. 2005 280:40261). This shows Btk could be useful to treat pathological mast cells responses such as allergy and asthma. Also monocytes from XLA patients, in which Btk activity is absent, show decreased TNF alpha production following stimulation (Horwood et al. J Exp Med 2003 197:1603). Therefore TNF alpha mediated inflammation could be modulated by small molecular Btk inhibitors. Also, Btk has been reported to play a role in apoptosis (Islam and Smith Immunol. Rev. 2000 178:49,) and thus Btk inhibitors would be useful for the treatment of certain B-cell lymphomas and leukemias (Feldhahn et al. J. Exp. Med. 2005 201:1837).

SUMMARY OF THE INVENTION

The present invention relates to compounds of formula I wherein:

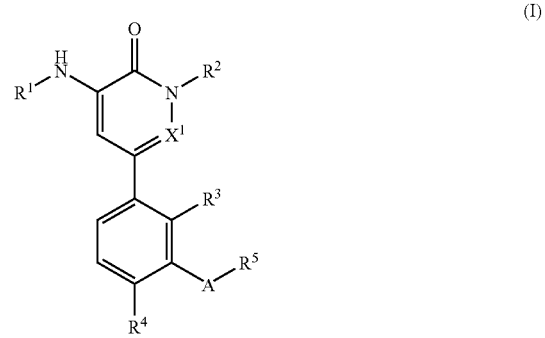

(I)

$X^1$ is CH or N;

$R^1$ is C(=O)NHR$^6$, phenyl or heteroaryl wherein said heteroaryl is selected from the group consisting of pyridinyl, pyridazinyl, pyrimidinyl, pyrazinyl; pyrrolyl, furanyl, thiophenyl, imidazolyl, pyrazolyl, oxazolyl, thiazolyl, isoxazolyl, isothiazolyl, 2-$C_{1-6}$alkyl-pyridazin-3-on-6-yl, 2-benzyl-pyridazin-3-on-6-yl, 1,4,5,6-tetrahydro-pyrimidin-2-yl and 4,5-dihydro-1H-imidazol-2-yl, with the proviso that when $X^1$ is CH, $R^1$ is C(=O)NHR$^6$ or $R^3$ is CH$_2$OH;

said phenyl and said heteroaryl optionally independently substituted with one to three groups selected from the group consisting of halogen, $C_{1-6}$alkyl, $C_{1-6}$alkoxy, $C_{1-6}$heteroalkyl, $C_{1-6}$heteroalkoxy, $C_{1-6}$alkylsulfanyl, $C_{1-6}$alkylsulfonyl, $C_{1-6}$heteroalkylsulfonyl and heterocyclyl-$C_{1-6}$alkoxy wherein said heterocyclyl is azetindinyl, pyrrolidinyl or piperidinyl, CONR$^a$R$^b$, CO$_2$R$^g$, SO$_2$NR$^a$R$^b$, NR$^a$R$^b$, NHSO$_2$R$^7$ or NHCOR$^7$;

$R^2$ and $R^g$ are independently hydrogen or $C_{1-6}$ alkyl;
$R^3$ and $R^4$ are independently hydrogen, halogen, amino, $C_{1-6}$ hydroxyalkyl, $C_{1-6}$ alkyl or cyclopropyl;
$R^5$ is (i) phenyl;
(ii) heteroaryl selected from the group consisting of pyridinyl, benzo[b]thiophen-2-yl, 4,5,6,7-tetrahydro-benzo[b]thiophen-2-yl, thiophenyl, 1',2',3',4',5',6'-hexahydro-[2,4']bipyridin-5-yl and $C_{1-3}$alkyl-indolyl optionally substituted with one or two $C_{1-6}$alkyl or halogen;
(iii) azetidin-1-yl, pyrrolidin-2-yl, piperidin-1-yl, azepan-1-yl or 2,3-dihydro-1H-isoindolin-2-yl, or 6,7-dihydro-5H-pyrrolo[3,4-b]pyridine;
(iv) $NR^cR^d$ wherein $R^c$ and $R^d$ together are $(CH_2)_oX^2(CH_2)_p$ wherein o and p are independently is 1 or 2, and $X^2$ is O, $S(O)_n$, $NR^8$ and n is 0 to 2, or $R^c$ and $R^d$ independently are hydrogen $C_{1-10}$ allyl or $C_{1-10}$ hydroxyalkyl;
(v)

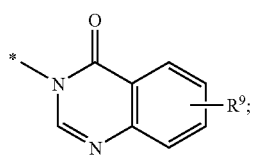

(vi)

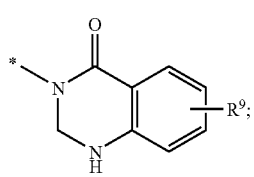

(vii)

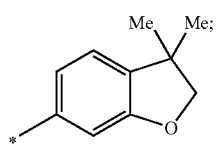

wherein said phenyl, heteroaryl, azetidin-1-yl, pyrrolidin-2-yl, piperidin-1-yl, azepan-1-yl or 2,3-dihydro-1H-isoindolin-2-yl ring is optionally substituted with one to three groups independently selected from the group consisting of (a) halogen, (b) $C_{1-6}$alkyl, (b) $C_{2-6}$alkenyl, (c) $C_{2-6}$alkynyl, (d) $C_{1-6}$haloalkyl, (e) $C_{1-6}$heteroalkyl, (f) $C_{3-7}$cycloalkyl optionally substituted with one to three groups selected from $C_{1-6}$alkyl, $C_{1-6}$haloalkyl or halogen, (g) $C_{1-6}$alkoxyalkyl, (h) hydroxy, (i) $NR^eR^f$, wherein $R^e$ and $R^f$ are (i) independently hydrogen, $C_{1-6}$alkyl or (ii) together are $(CH_2)_mX^3(CH_2)_2$ wherein m is 2 or 3 and $X^3$ is $CH_2$, O, $S(O)_n$ or $NR^8$ and n is zero to two and $R^8$ is as defined above; (j) $C_{1-6}$alkoxy, (k) trialkylsilyl, (l) $C_{1-6}$cyanoalkyl and (m) $SF_5$
$R^6$ is hydrogen, $C_{1-6}$ alkyl, $C_{1-6}$ haloalkyl, $C_{1-6}$ heteroalkyl, $C_{3-6}$ cycloalkyl, pyridinyl-$C_{1-3}$ alkyl, phenyl or phenyl-$C_{1-3}$ alkyl said phenyl optionally substituted with $C_{1-6}$ alkyl, $C_{1-6}$ alkoxy, $C_{1-6}$ heteroalkoxy, halogen, $CONR^aR^b$, $CO_2R^e$;
A is —NHC(=O)—, C(=O)NH—, NHC(=O)NH, $CH_2C(=O)$, $CH_2SO_2$ or if $R^5$ is (v) or (vi) A is absent;

$R^a$ and $R^b$ (i) selected independently are hydrogen, $C_{1-6}$ alkyl, $C_{1-6}$ heteroalkyl, $C_{1-3}$ alkoxy $C_{1-3}$ alkyl, carboxy $C_{1-3}$ alkyl, $C_{3-6}$ cycloalkyl or heterocyclyl (ii) together are $(CH_2)_mX^2(CH_2)_2$ wherein m is 2 or 3 and $X^2$ is O, $S(O)_n$, $NR^8$ and n is zero to two, or (iii) together with the nitrogen to which they are attached are piperidine or pyrrolidine said piperidine or said pyrrolidine optionally substituted with hydroxy, $C_{1-3}$ alkoxy, $C_{1-3}$ hydroxy alkyl;
$R^7$ is $C_{1-6}$ alkyl or $C_{1-6}$ heteroalkyl;
$R^8$ is hydrogen, $C_{1-6}$ alkyl, $C_{1-6}$ hydroxyalkyl or $C_{1-3}$ acyl;
$R^9$ is hydrogen, halogen or $C_{1-6}$ alkyl; or,
pharmaceutically acceptable salts thereof.

The compounds of formula I inhibit Bruton's tyrosine kinase (Btk). Activation of Btk by upstream kinases results in activation of phospholipase-Cγ which, in turn, stimulates release of pro-inflammatory mediators. Compounds of formula I are useful in the treatment of arthritis and other anti-inflammatory and auto-immune diseases. Compounds according to formula I are, according, useful for the treatment of arthritis. Compounds of formula I are useful for inhibiting Btk in cells and for modulating B-cell development. The present invention further comprises pharmaceutical compositions containing compounds of formula I admixed with pharmaceutically acceptable carrier, excipients or diluents.

DETAILED DESCRIPTION OF THE INVENTION

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined herein above" refers to the broadest definition for each group as provided in the Summary of the Invention or the broadest claim. In all other embodiments provided below, substituents which can be present in each embodiment and which are not explicitly defined retain the broadest definition provided in the Summary of the Invention.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

As used herein, unless specifically indicated otherwise, the word "or" is used in the "inclusive" sense of "and/or" and not the "exclusive" sense of "either/or".

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

When any variable (e.g., $R^1$, $R^{4a}$, Ar, $X^1$ or Het) occurs more than one time in any moiety or formula depicting and describing compounds employed or claimed in the present invention, its definition on each occurrence is independent of its definition at every other occurrence. Also, combinations of substituents and/or variables are permissible only if such compounds result in stable compounds.

The symbols "*" at the end of a bond or "-----" drawn through a bond each refer to the point of attachment of a functional group or other chemical moiety to the rest of the molecule of which it is a part. Thus, for example:

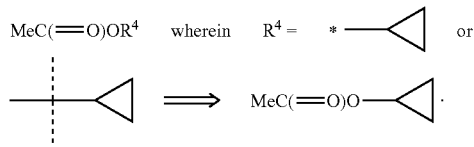

A bond drawn into ring system (as opposed to connected at a distinct vertex) indicates that the bond may be attached to any of the suitable ring atoms.

The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen or a substituent.

The phrase "optional bond" means that the bond may or may not be present, and that the description includes single, double, or triple bonds. If a substituent is designated to be a "bond" or "absent", the atoms linked to the substituents are then directly connected.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

The definitions described herein may be appended to form chemically-relevant combinations, such as "heteroalkylaryl," "haloalkylheteroaryl," "arylalkylheterocyclyl," "alkylcarbonyl," "alkoxyalkyl," and the like. When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" refers to an alkyl group having one to two phenyl substituents, and thus includes benzyl, phenylethyl, and biphenyl. An "alkylaminoalkyl" is an alkyl group having one to two alkylamino substituents. "Hydroxyalkyl" includes 2-hydroxyethyl, 2-hydroxypropyl, 1-(hydroxymethyl)-2-methylpropyl, 2-hydroxybutyl, 2,3-dihydroxybutyl, 2-(hydroxymethyl), 3-hydroxypropyl, and so forth. Accordingly, as used herein, the term "hydroxyalkyl" is used to define a subset of heteroalkyl groups defined below. The term -(ar)alkyl refers to either an unsubstituted alkyl or an aralkyl group. The term (hetero)aryl or (het)aryl refers to either an aryl or a heteroaryl group.

Compounds of formula I exhibit tautomerism. Tautomeric compounds can exist as two or more interconvertible species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol ($-C(=O)-CH- \leftrightarrows -C(-OH)=CH-$), amide/imidic acid ($-C(=O)-NH- \leftrightarrows -C(-OH)=N-$) and amidine ($-C(=NR)-NH- \leftrightarrows -C(-NHR)=N-$) tautomers. The latter two are particularly common in heteroaryl and heterocyclic rings and the present invention encompasses all tautomeric forms of the compounds.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of Therapeutics,* 10$^{th}$ Ed., McGraw Hill Companies Inc., New York (2001). Any suitable materials and/or methods known to those of skill can be utilized in carrying out the present invention. However, preferred materials and methods are described. Materials, reagents and the like to which reference are made in the following description and examples are obtainable from commercial sources, unless otherwise noted.

In one embodiment of the present invention there is provided a compound according to formula I wherein $R^1$, $R^2$, $R^3$, $R^4$ $R^5$, $X^1$ and A are as defined herein above.

In a second embodiment of the present invention there is provided a compound according to formula I wherein $X^1$ is N and $R^1$, $R^2$, $R^3$, $R^4$ $R^5$ and A are as defined herein above.

In a third embodiment of the present invention there is provided a compound according to formula I wherein $X^1$ is N; $R^1$ is phenyl, pyridine-2-yl or pyrimidin-4-yl; $R^2$ is $C_{1-3}$ alkyl; $R^3$ is hydrogen or $C_{1-3}$ alkyl; A is NHC(=O); and $R^4$ and $R^5$ are as defined herein above.

I another embodiment of the present invention there is provided a compound according to formula I wherein $X^1$ is N; $R^1$ is phenyl, pyridine-2-yl or pyrimidin-4-yl; $R^2$ is $C_{1-3}$ alkyl; $R^3$ is $C_{1-6}$ hydroxyalkyl; A is NHC(=O); and $R^4$ and $R^5$ are as defined herein above.

In a fourth embodiment of the present invention there is provided a compound according to formula I wherein $X^1$ is N; $R^1$ is phenyl, pyridine-2-yl or pyrimidin-4-yl; $R^2$ is $C_{1-3}$ alkyl; $R^3$ is hydroxymethyl; A is NHC(=O); and $R^4$ and $R^5$ are as defined herein above.

In a fifth embodiment of the present invention there is provided a compound according to formula I wherein $X^1$ is N; $R^1$ is phenyl, pyridine-2-yl or pyrimidin-4-yl; $R^2$ is $C_{1-3}$ alkyl; $R^3$ is hydroxymethyl; A is NHC(=O); $R^5$ is optionally substituted phenyl, optionally substituted pyridinyl, benzo[b]thiophen-2-yl or 4,5,6,7-tetrahydro-benzo[b]thiophen-2-yl; and $R^4$ is as defined herein above.

In a sixth embodiment of the present invention there is provided a compound according to formula I wherein $X^1$ is N; $R^1$ is pyridin-2-yl optionally substituted with $CONR^aR^b$, $NR^aR^b$, $C_{1-6}$ alkoxy, $C_{1-6}$ heteroalkoxy, $C_{1-6}$ alkylsulfanyl or $C_{1-6}$ alkylsulfonyl; $R^2$ is $C_{1-3}$ alkyl; $R^3$ is hydroxymethyl; A is NHC(=O); $R^5$ is optionally substituted phenyl, optionally substituted pyridinyl, benzo[b]thiophen-2-yl or 4,5,6,7-tetrahydro-benzo[b]thiophen-2-yl; and $R^4$ is as defined herein above.

In another embodiment of the present invention there is provided a compound according to formula I wherein $X^1$ is N; $R^1$ is pyridin-2-yl optionally substituted with $CONR^aR^b$, $NR^aR^b$, $C_{1-6}$ alkoxy, $C_{1-6}$ heteroalkoxy, $C_{1-6}$ alkylsulfanyl or $C_{1-6}$ alkylsulfonyl; $R^2$ is $C_{1-3}$ alkyl; $R^3$ is hydrogen or $C_{1-3}$ alkyl; A is NHC(=O); $R^5$ is optionally substituted phenyl, optionally substituted pyridinyl, benzo[b]thiophen-2-yl or 4,5,6,7-tetrahydro-benzo[b]thiophen-2-yl; and $R^4$ is as defined herein above.

In a seventh embodiment of the present invention there is provided a compound according to formula I wherein $X^1$ is N; $R^1$ is pyrimidin-4-yl optionally substituted with $CONR^aR^b$, $NR^aR^b$, $C_{1-6}$ alkoxy, $C_{1-6}$ heteroalkoxy, $C_{1-6}$ alkylsulfanyl or $C_{1-6}$ alkylsulfonyl; $R^2$ is $C_{1-3}$ alkyl; $R^3$ is hydroxymethyl; A is NHC(=O); $R^5$ is optionally substituted phenyl, optionally substituted pyridinyl, benzo[b]thiophen-2-yl or 4,5,6,7-tetrahydro-benzo[b]thiophen-2-yl; and $R^4$ is as defined herein above.

In another embodiment of the present invention there is provided a compound according to formula I wherein $X^1$ is N; $R^1$ is pyrimidin-4-yl optionally substituted with $CONR^aR^b$, $NR^aR^b$, $C_{1-6}$ alkoxy, $C_{1-6}$ heteroalkoxy, $C_{1-6}$ alkylsulfanyl or $C_{1-6}$ alkylsulfonyl; $R^2$ is $C_{1-3}$ alkyl; $R^3$ is hydrogen or $C_{1-3}$ alkyl; A is NHC(=O); $R^5$ is optionally substituted phenyl, optionally substituted pyridinyl, benzo[b]thiophen-2-yl or 4,5,6,7-tetrahydro-benzo[b]thiophen-2-yl; and $R^4$ is as defined herein above.

In a eighth embodiment of the present invention there is provided a compound according to formula I wherein $X^1$ is N; $R^1$ is phenyl optionally substituted with $CONR^aR^b$, $NR^aR^b$, $C_{1-6}$ alkoxy, $C_{1-6}$ heteroalkoxy, $C_{1-6}$ alkylsulfanyl or $C_{1-6}$ alkylsulfonyl; $R^2$ is $C_{1-3}$ alkyl; $R^3$ is hydroxymethyl; A is NHC(=O); $R^5$ is optionally substituted phenyl, optionally substituted pyridinyl, benzo[b]thiophen-2-yl or 4,5,6,7-tetrahydro-benzo[b]thiophen-2-yl; and $R^4$ is as defined herein above.

In a another embodiment of the present invention there is provided a compound according to formula I wherein $X^1$ is N; $R^1$ is phenyl optionally substituted with $CONR^aR^b$, $NR^aR^b$, $C_{1-6}$ alkoxy, $C_{1-6}$ heteroalkoxy, $C_{1-6}$ alkylsulfanyl or $C_{1-6}$ alkylsulfonyl; $R^2$ is $C_{1-3}$ alkyl; $R^3$ is hydrogen or $C_{1-3}$ alkyl; A is NHC(=O); $R^5$ is optionally substituted phenyl, optionally substituted pyridinyl, benzo[b]thiophen-2-yl or 4,5,6,7-tetrahydro-benzo[b]thiophen-2-yl; and $R^4$ is as defined herein above.

In a ninth embodiment of the present invention there is provided a compound according to formula I wherein $X^1$ is N; $R^1$ is C(=O)NHR$^6$; $R^6$ is $C_{1-6}$ alkyl; $R^3$ is hydrogen, $C_{1-3}$ alkyl or $C_{1-6}$ heteroalkyl; A is NHC(=O) $R^2$, $R^4$ and $R^5$ are as defined herein above.

In another embodiment of the present invention there is provided a compound according to formula I wherein $X^1$ is N; $R^1$ is C(=O)NHR$^6$; $R^6$ is $C_{1-6}$ heteroalkyl; $R^3$ is hydrogen, $C_{1-3}$ alkyl or $C_{1-6}$ heteroalkyl; A is NHC(=O) $R^2$, $R^4$ and $R^5$ are as defined herein above.

In a tenth embodiment of the present invention there is provided a compound according to formula I wherein $X^1$ is CH and $R^1$, $R^2$, $R^3$, $R^4$ $R^5$ and A are as defined herein above.

In a eleventh embodiment of the present invention there is provided a compound according to formula I wherein $X^1$ is CH; $R^1$ is pyridin-2-yl or pyrimidin-4-yl; $R^2$ is $C_{1-3}$ alkyl; $R^3$ is hydroxymethyl; A is NHC(=O); and $R^4$ and $R^5$ are as defined herein above.

In a twelfth embodiment of the present invention there is provided a compound according to formula I wherein $X^1$ is CH; $R^1$ is pyridin-2-yl or pyrimidin-4-yl; $R^2$ is $C_{1-3}$ alkyl; $R^3$ is hydroxymethyl; $R^5$ is optionally substituted phenyl, optionally substituted pyridinyl, benzo[b]thiophen-2-yl or 4,5,6,7-tetrahydro-benzo[b]thiophen-2-yl; A is NHC(=O); and $R^4$ is as defined herein above.

In a thirteenth embodiment of the present invention there is provided a compound according to formula I wherein $X^1$ is CH; $R^1$ is pyridin-2-yl optionally substituted with $CONR^aR^b$, $NR^aR^b$, $C_{1-6}$ alkoxy, $C_{1-6}$ heteroalkoxy, $C_{1-6}$ alkylsulfanyl or $C_{1-6}$ alkylsulfonyl; $R^3$ is hydroxymethyl; $R^5$ is optionally substituted phenyl, optionally substituted pyridinyl, benzo[b]thiophen-2-yl or 4,5,6,7-tetrahydro-benzo[b]thiophen-2-yl; A is NHC(=O); and $R^4$ is as defined herein above.

In a fourteenth embodiment of the present invention there is provided a compound according to formula I wherein $X^1$ is CH; $R^1$ is pyrimidin-4-yl optionally substituted $CONR^aR^b$, $NR^aR^b$, $C_{1-6}$ alkoxy, $C_{1-6}$ heteroalkoxy, $C_{1-6}$ alkylsulfanyl or $C_{1-6}$ alkylsulfonyl.; $R^3$ is hydroxymethyl; $R^5$ is optionally substituted phenyl, optionally substituted pyridinyl, benzo[b]thiophen-2-yl or 4,5,6,7-tetrahydro-benzo[b]thiophen-2-yl; A is NHC(=O); and $R^4$ is as defined herein above.

In a fifteenth embodiment of the present invention there is provided a compound according to formula I wherein $X^1$ is CH and $R^1$ is C(=O)NHR$^6$, $R^6$ is $C_{1-6}$ alkyl, $R^3$ is hydrogen, $C_{1-3}$ alkyl or $C_{1-6}$ heteroalkyl; A is NHC(=O), $R^2$, $R^4$ $R^5$ are as defined herein above.

In a sixteenth embodiment of the present invention there is provided a compound according to formula I wherein $X^1$ is CH and $R^1$ is C(=O)NHR$^6$, $R^6$ is $C_{1-6}$ alkyl, $R^3$ is hydroxymethyl; A is NHC(=O), $R^2$, $R^4$ $R^5$ are as defined herein above.

In a seventeenth embodiment of the present invention there is provided a compound according to formula I wherein $R^5$ is (v) or (vi); A is absent; and $R^1$, $R^2$, $R^3$, $R^4$ and $X^1$ are as defined herein above.

In a eighteenth embodiment of the present invention there is provided a compound according to formula I wherein A is $CH_2C$(=O) and $R^5$ is (i), (ii), (iii) or (iv); and $R^1$, $R^2$, $R^3$, $R^4$ and $X^1$ are as defined herein above.

In a nineteenth embodiment of the present invention there is provided a compound selected from compounds I-1 to I-46 of TABLE I or from II-4 to II-19, II-21 to II-23, II-27 to II-31, II-45 to II-47 and II-49 to II-87 of TABLE II.

In a twentieth embodiment of the present invention there is provided a method for treating an inflammatory and/or autoimmune condition comprising administering to a patient in need thereof a compound according of formula I wherein $R^1$, $R^2$, $R^3$, $R^4$ $R^5$, $X^1$ and A are as defined herein above.

In a twenty-first embodiment of the present invention there is provided a method for treating rheumatoid arthritis comprising administering to a patient in need thereof a compound according to formula I wherein $R^1$, $R^2$, $R^3$, $R^4$ $R^5$, $X^1$ and A are as defined herein above.

In a twenty-second embodiment of the present invention there is provided a method of inhibiting B-cell proliferation comprising administering to a patient in need thereof a compound according to formula I wherein $R^1$, $R^2$, $R^3$, $R^4$ $R^5$, $X^1$ and A are as defined herein above.

In a twenty-third embodiment of the present invention there is provided a method for inhibiting Btk activity comprising administering to a patient in need thereof a compound according to formula I wherein $R^1$, $R^2$, $R^3$, $R^4$ $R^5$, $X^1$ and A are as defined herein above wherein the compound exhibits an $IC_{50}$ of 1 micromolar or less in an in vitro biochemical assay of Btk activity.

In a twenty-fourth embodiment of the present invention there is provided a method for inhibiting Btk activity comprising administering to a patient in need thereof a compound according to formula I wherein $R^1$, $R^2$, $R^3$, $R^4$ $R^5$, $X^1$ and A are as defined herein above wherein the compound exhibits an $IC_{50}$ of 100 nanomolar or less in an in vitro biochemical assay of Btk activity.

In a twenty-fifth embodiment of the present invention there is provided a method for treating an inflammatory condition comprising co-administering to a patient in need thereof a therapeutically effective amount of an anti-inflammatory compound along with a compound according to formula I wherein $R^1$, $R^2$, $R^3$, $R^4$ $R^5$, $X^1$ and A are as defined herein above.

In a twenty-sixth embodiment of the present invention there is provided a method for treating rheumatoid arthritis comprising co-administering to a patient in need thereof a therapeutically effective amount of an anti-inflammatory compound along with a compound according to formula I wherein $R^1$, $R^2$, $R^3$, $R^4$ $R^5$, $X^1$ and A are as defined herein above.

In a twenty-seventh embodiment of the present invention there is provided a pharmaceutical composition comprising a compound according to formula I wherein $R^1$, $R^2$, $R^3$, $R^4$ $R^5$, $X^1$ and A are as defined herein above admixed with at least one pharmaceutically acceptable carrier, excipient or diluent.

The term "acyl" as used herein denotes a group of formula —C(=O)R wherein R is hydrogen or lower alkyl as defined herein. The term "alkylcarbonyl" as used herein denotes a group of formula C(=O)R wherein R is alkyl as defined herein. The term $C_{1-6}$ acyl refers to a group —C(=O)R containing 6 carbon atoms; the formyl group is encompassed in this group (C1 wherein R=H). The term "arylcarbonyl" as used herein means a group of formula C(=O)R wherein R is an aryl group; the term "benzoyl" as used herein an "arylcarbonyl" group wherein R is phenyl.

The term "alkyl" as used herein denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "$C_{1-10}$ alkyl" as used herein refers to an alkyl composed of 1 to 10 carbons. Examples of alkyl groups include, but are not limited to, methyl, ethyl, propyl, i-propyl, n-butyl, i-butyl, t-butyl or pentyl, isopentyl, neopentyl, hexyl, heptyl, and octyl.

When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" denotes the radical R'R"—, wherein R' is a phenyl radical, and R" is an alkylene radical as defined herein with the understanding that the attachment point of the phenylalkyl moiety will be on the alkylene radical. Examples of arylalkyl radicals include, but are not limited to, benzyl, phenylethyl, 3-phenylpropyl. The terms "arylalkyl" or "aralkyl" are interpreted similarly except R' is an aryl radical. The terms "(het)arylalkyl" or "(het)aralkyl" are interpreted similarly except R' is optionally an aryl or a heteroaryl radical.

The term "haloalkyl" as used herein denotes a unbranched or branched chain alkyl group as defined above wherein 1, 2, 3 or more hydrogen atoms are substituted by a halogen. Examples are 1-fluoromethyl, 1-chloromethyl, 1-bromomethyl, 1-iodomethyl, difluoromethyl, trifluoromethyl, trichloromethyl, tribromomethyl, triiodomethyl, 1-fluoroethyl, 1 -chloroethyl, 1-bromoethyl, 1-iodoethyl, 2-fluoroethyl, 2-chloroethyl, 2 -bromoethyl, 2-iodoethyl, 2,2 -dichloroethyl, 3-bromopropyl or 2,2,2-trifluoroethyl.

The term "alkylene" as used herein denotes a divalent saturated linear hydrocarbon radical of 1 to 10 carbon atoms (e.g., $(CH_2)_n$) or a branched saturated divalent hydrocarbon radical of 2 to 10 carbon atoms (e.g., —CHMe- or —$CH_2CH$(i-Pr)$CH_2$—), unless otherwise indicated. Except in the case of methylene, the open valences of an alkylene group are not attached to the same atom. Examples of alkylene radicals include, but are not limited to, methylene, ethylene, propylene, 2-methyl-propylene, 1,1-dimethyl-ethylene, butylene, 2 - ethylbutylene.

The term "alkoxy" as used herein means an —O-alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers. "Lower alkoxy" as used herein denotes an —O-alkyl group wherein alkyl is "lower alkyl" as previously defined. "$C_{1-10}$ alkoxy" as used herein refers to an-O-alkyl wherein alkyl is $C_{1-10}$ alkyl.

The term "alkoxyalkyl" as used herein refers to the radical R'R"—, wherein R' is an alkoxy radical as defined herein, and R" is an alkylene radical as defined herein with the understanding that the attachment point of the alkoxyalkyl moiety will be on the alkylene radical. $C_{1-6}$ alkoxyalkyl denotes a group wherein the alkyl portion is comprised of 1-6 carbon atoms exclusive of carbon atoms in the alkoxy portion of the group. $C_{1-3}$ alkoxy-$C_{1-6}$ alkyl denotes a group wherein the alkyl portion is comprised of 1-6 carbon atoms and the alkoxy group is 1-3 carbons. Examples are methoxymethyl, methoxyethyl, methoxypropyl, ethoxymethyl, ethoxyethyl, ethoxypropyl, propyloxypropyl, methoxybutyl, ethoxybutyl, propyloxybutyl, butyloxybutyl, t-butyloxybutyl, methoxypentyl, ethoxypentyl, propyloxypentyl including their isomers.

The term "heteroalkoxy" as used herein means an —O-(heteroalkyl) group wherein heteroalkyl is as defined herein. $C_{1-10}$ heteroalkoxy" as used herein refers to anO—($C_{1-10}$ heteroalkyl) wherein $C_{1-10}$ heteroalkyl is as defined herein. Representative examples include, but are not limited to, 2-dimethylaminoethoxy and 3-sulfonamido-1-propoxy.

The term "heteroalkyl" as used herein refers to an alkyl radical as defined herein wherein one, two or three hydrogen atoms have been replaced with a substituent independently selected from the group consisting of —$OR^a$, —$NR^bR^c$, and —$S(O)_nR^d$ (where n is an integer from 0 to 2), with the understanding that the point of attachment of the heteroalkyl radical is through a carbon atom, and wherein $R^a$ is hydrogen, acyl, alkyl, cycloalkyl, or cycloalkylalkyl; $R^b$ and $R^c$ are independently of each other hydrogen, acyl, alkyl, cycloalkyl, or cycloalkylalkyl; and when n is 0, $R^d$ is hydrogen, alkyl, cycloalkyl, or cycloalkylalkyl, and when n is 1 or 2, $R^d$ is alkyl, cycloalkyl, cycloalkylalkyl, amino, alkylamino, dialkylamino or phenyl. Representative examples include, but are not limited to, 2-hydroxyethyl, 3-hydroxypropyl, 2 -hydroxy-1-hydroxymethylethyl, 2,3-dihydroxypropyl, 1-hydroxymethylethyl, 3-hydroxybutyl, 2, 3-dihydroxybutyl, 2-hydroxy-1-methylpropyl, 2-aminoethyl, 3-aminopropyl, 2 - methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like. The term "cyanoalkyl" as used herein refers to an alkyl radical as defined herein wherein one hydrogen atom has been replaced with a cyano substituent.

The term "hydroxyalkyl" as used herein denotes an alkyl radical as herein defined wherein one to three hydrogen atoms on different carbon atoms is/are replaced by hydroxyl groups.

The term "alkylthio" or "alkylsulfanyl" refers to an —S-alkyl group, wherein alkyl is as defined above such as meththio, ethylthio, n-propylthio, i-propylthio, n-butylthio, hexylthio, including their isomers. "Lower alkylthio" as used herein denotes an alkylthio group with a "lower alkyl" group as previously defined. "$C_{1-10}$ alkylthio" as used herein refers to an-S-alkyl wherein alkyl is $C_{1-10}$. "Phenylthio" is an "arylthio" moiety wherein aryl is phenyl.

The terms "alkylcarbonylamino" and "arylcarbonylamino" as used herein refers to a group of formula —NC(=O)R wherein R is alkyl or aryl respectively and alkyl and aryl are as defined herein.

The terms "alkylsulfinyl" and "arylsulfinyl" as used herein refers to a group of formula —S(=O)R wherein R is alkyl or aryl respectively and alkyl and aryl are as defined herein The terms "alkylsulfonyl" and "arylsulfonyl" as used herein refers to a group of formula —S(=O)₂R wherein R is alkyl or aryl respectively and alkyl and aryl are as defined herein. The term "heteroalkylsulfonyl" as used herein refers herein denotes a group of formula —S(=O)₂R wherein R is "heteroalkyl" as defined herein.

The terms "alkylsulfonylamino" and "arylsulfonylamino" as used herein refers to a group of formula —NR'S(=O)₂R wherein R is alkyl or aryl respectively, R' is hydrogen or $C_{1-3}$ alkyl, and alkyl and aryl are as defined herein.

The term "cycloalkyl" as used herein refers to a saturated carbocyclic ring containing 3 to 8 carbon atoms, i.e. cyclopropyl, cyclobutyl, cyclopentyl, cyclohexyl, cycloheptyl or cyclooctyl. "$C_{3-7}$ cycloalkyl" as used herein refers to an cycloalkyl composed of 3 to 7 carbons in the carbocyclic ring.

The term carboxy-alkyl as used herein refers to an alkyl moiety wherein one, hydrogen atom has been replaced with a carboxyl with the understanding that the point of attachment of the heteroalkyl radical is through a carbon atom. The term carboxyl refers to a —CO₂H moiety.

The term "halogen" or "halo" as used herein means fluorine, chlorine, bromine, or iodine.

The terms azetidine, pyrrolidine, piperidine and azepine refer to a four, five, six and seven membered saturated ring containing one nitrogen atom in the ring. The "1"-position refers to the nitrogen atom.

The terms benzo[b]thiophen-2-yl, 4,5,6,7-tetrahydro-benzo[b]thiophen-2-yl, thiophenyl 2,3-dihydro-1H-isoindolin-2-yl, 1',2',3',4',5',6'-hexahydro-[2,4']bipyridin-5-yl, and 6,7-dihydro-5H-pyrrolo[3,4-b]pyridine refer to moieties (i) to (vi) respectively.

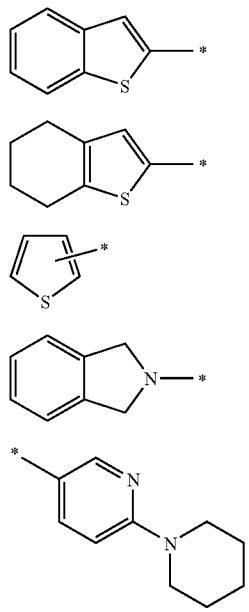

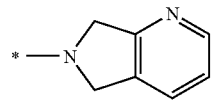

The terms "1,4,5,6-tetrahydro-pyrimidin-2-ylamine" and "4,5-dihydro-1H-imidazol-2-ylamine" refer to the moieties (vii) and (viii) respectively.

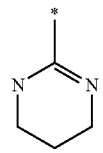

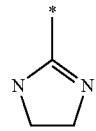

The term "heteroaryl" or "heteroaromatic" as used herein means a monocyclic or bicyclic radical of 5 to 12 ring atoms having at least one aromatic ring containing four to eight atoms per ring, incorporating one or more N, O, or S heteroatoms, the remaining ring atoms being carbon, with the understanding that the attachment point of the heteroaryl radical will be on an aromatic ring. As well known to those skilled in the art, heteroaryl rings have less aromatic character than their all-carbon counter parts. Thus, for the purposes of the invention, a heteroaryl group need only have some degree of aromatic character. Examples of heteroaryl moieties include monocyclic aromatic heterocycles having 5 to 6 ring atoms and 1 to 3 heteroatoms include, but is not limited to, pyridinyl, pyrimidinyl, pyrazinyl, pyrrolyl, pyrazolyl, imidazolyl, oxazolyl, isoxazolyl, thiazolyl, isothiazolyl, triazolinyl, thiadiazolyl and oxadiaxolinyl which can optionally be substituted with one or more, preferably one or two, substituents selected from hydroxy, cyano, alkyl, alkoxy, thio, lower haloalkoxy, alkylthio, halo, haloalkyl, alkylsulfinyl, alkylsulfonyl, halogen, amino, alkylamino, dialkylamino, aminoalkyl, alkylaminoalkyl, and dialkylaminoalkyl, nitro, alkoxycarbonyl and carbamoyl, alkylcarbamoyl, dialkylcarbamoyl, arylcarbamoyl, alkylcarbonylamino and arylcarbonylamino. Examples of bicyclic moieties include, but are not limited to, quinolinyl, isoquinolinyl, benzofuryl, benzothiophenyl, benzoxazolyl, benzisoxazolyl, benzothiazolyl and benzisothazolyl. Bicyclic moieties can be optionally substituted on either ring; however the point of attachment is on a ring containing a heteroatom.

The term (hetero)aryl as used herein refers to an aryl or a heteroaryl moiety as each is defined herein.

The term "heterocyclyl" or "heterocycle" as used herein denotes a monovalent saturated cyclic radical, consisting of one or more rings, preferably one to two rings, of three to eight atoms per ring, incorporating one or more ring heteroatoms (chosen from N, O or S(O)0-2), and which can optionally be independently substituted with one or more, preferably one or two substituents selected from hydroxy, oxo, cyano, lower alkyl, lower alkoxy, lower haloalkoxy, alkylthio, halo, haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonylamino, arylcarbonylamino, unless otherwise indicated. Examples of heterocyclic radicals include, but are not limited to, azetidinyl, pyrrolidinyl, hexahydroazepinyl, oxetanyl, tetrahydrofuranyl, tetrahydrothiophenyl, oxazolidinyl, thiazolidinyl, isoxazolidinyl, morpholinyl, piperazinyl, piperidinyl, tetrahydropyranyl, thiomorpholinyl, quinuclidinyl and imidazolinyl.

The term "heterocyclyl-$C_{1-6}$ alkoxy" as used herein refers to the radical R'R"—, wherein R' is an alkoxy radical as defined herein, wherein one, two of the hydrogen atoms attached to a carbone has been replaced with a heterocyclic substituent and heterocyclyl-$C_{1-6}$ alkoxy moiety is attached at the oxygen atom of the alkoxy group.

The term "N-alkyl-ureido" as used herein refers to a group RNHC(=O)NH— wherein R is an alkl group as defined herein.

Commonly used abbreviations include: acetyl (Ac), azo-bis-isobutyrylnitrile (AIBN), atmospheres (Atm), 9-borabicyclo[3.3.1]nonane (9-BBN or BBN), tert-butoxycarbonyl (Boc), di-tert-butyl pyrocarbonate or boc anhydride (BOC$_2$O), benzyl (Bn), butyl (Bu), Chemical Abstracts Registration Number (CASRN), benzyloxycarbonyl (CBZ or Z), carbonyl diimidazole (CDI), 1,4-diazabicyclo[2.2.2]octane (DABCO), diethylaminosulfur trifluoride (DAST), dibenzylideneacetone (dba), 1,5-diazabicyclo[4.3.0]non-5-ene (DBN), 1,8-diazabicyclo[5.4.0]undec-7-ene (DBU), N,N'-dicyclohexylcarbodiimide (DCC), 1,2-dichloroethane (DCE), dichloromethane (DCM), diethyl azodicarboxylate (DEAD), di-iso-propylazodicarboxylate (DIAD), di-iso-butylaluminumhydride (DIBAL or DIBAL-H), di-iso-propylethylamine (DIPEA), N,N-dimethyl acetamide (DMA), 4-N,N-dimethylaminopyridine (DMAP), N,N-dimethylformamide (DMF), dimethyl sulfoxide (DMSO), 1,1'-bis-(diphenylphosphino)ethane (dppe), 1,1'-bis-(diphenylphosphino)ferrocene (dppf), 1-(3-dimethylaminopropyl)-3-ethylcarbodiimide hydrochloride (EDCI), ethyl (Et), ethyl acetate (EtOAc), ethanol (EtOH), 2-ethoxy-2H-quinoline-1-carboxylic acid ethyl ester (EEDQ), diethyl ether (Et$_2$O), O-(7-azabenzotriazole-1-yl)-N,N,N'N'-tetramethyluronium hexafluorophosphate acetic acid (HATU), acetic acid (HOAc), 1-N-hydroxybenzotriazole (HOBt), high pressure liquid chromatography (HPLC), iso-propanol (IPA), lithium hexamethyl disilazane (LiHMDS), methanol (MeOH), melting point (mp), MeSO$_2$— (mesyl or Ms), methyl (Me), acetonitrile (MeCN), m-chloroperbenzoic acid (MCPBA), mass spectrum (ms), methyl t-butyl ether (MTBE), N-bromosuccinimide (NBS), N-carboxyanhydride (NCA), N-chlorosuccinimide (NCS), N-methylmorpholine (NMM), N-methylpyrrolidone (NMP), pyridinium chlorochromate (PCC), pyridinium dichromate (PDC), phenyl (Ph), propyl (Pr), iso-propyl (i-Pr), pounds per square inch (psi), pyridine (pyr), room temperature (rt or RT), tert-butyldimethylsilyl or t-BuMe$_2$Si (TBDMS), triethylamine (TEA or Et$_3$N), 2,2,6,6-tetramethylpiperidine 1-oxyl (TEMPO), triflate or CF$_3$SO$_2$— (Tf), trifluoroacetic acid (TFA), 1,1'-bis-2,2,6,6-tetramethyl-heptane-2,6-dione (TMHD), O-benzotriazol-1-yl-N,N,N',N'-tetramethyluronium tetrafluoroborate (TBTU), thin layer chromatography (TLC), tetrahydrofuran (THF), trimethylsilyl or Me$_3$Si (TMS), p-toluenesulfonic acid monohydrate (TsOH or pTsOH), 4-Me-C$_6$H$_4$SO$_2$— or tosyl (Ts), N-urethane-N-carboxyanhydride (UNCA), Conventional nomenclature including the prefixes normal (n), iso (i-), secondary (sec-), tertiary (tert-) and neo have their customary meaning when used with an alkyl moiety. (J. Rigaudy and D. P. Klesney, *Nomenclature in Organic Chemistry, IUPAC* 1979 Pergamon Press, Oxford.).

Compounds and Preparation

Examples of representative compounds encompassed by the present invention and within the scope of the invention are provided in the following Table. These examples and preparations which follow are provided to enable those skilled in the art to more clearly understand and to practice the present invention. They should not be considered as limiting the scope of the invention, but merely as being illustrative and representative thereof.

In general, the nomenclature used in this Application is based on AUTONOM™ v.4.0, a Beilstein Institute computerized system for the generation of IUPAC systematic nomenclature. If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

TABLE I depicts examples of pyridazinone compounds according to formula I wherein $X^1$ is N.

TABLE I

| Cpd. # | Structure | mw | ms | mp | $IC_{50}$[1] (μM) |
|---|---|---|---|---|---|
| I-1 | 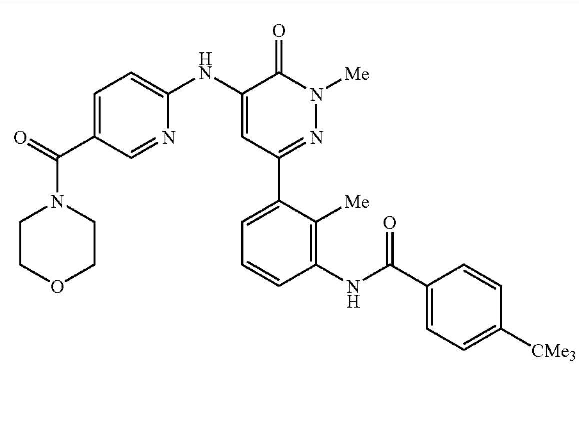 | 580 | 581 | 148.0-150.0 | <0.01 |

TABLE I-continued

| Cpd. # | Structure | mw | ms | mp | IC$_{50}$$^1$ (μM) |
|---|---|---|---|---|---|
| I-2 | 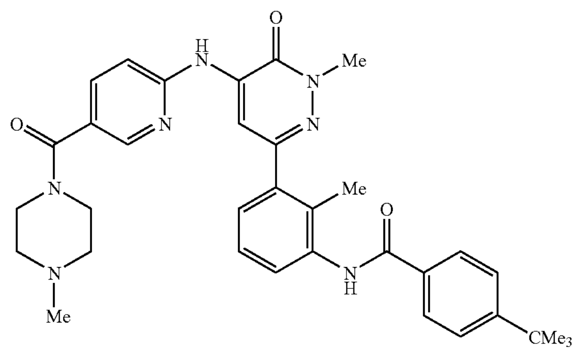 | 593 | 594 | 158.0-160.0 | 0.014 |
| I-3 | 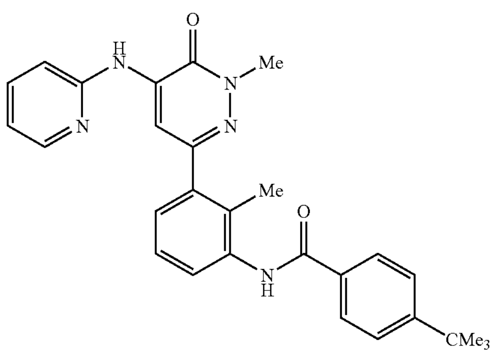 | 467 | 468 | 248.5-249.3 | 0.094 |
| I-4 | 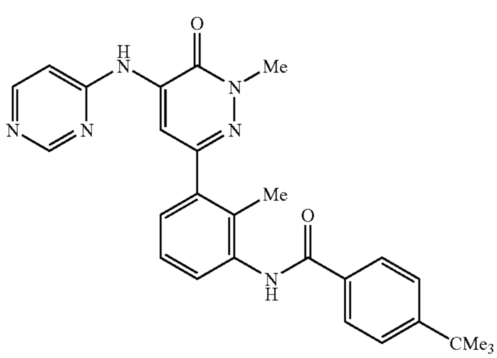 | 468 | 469 | 249.0-250.0 | 0.208 |
| I-5 | 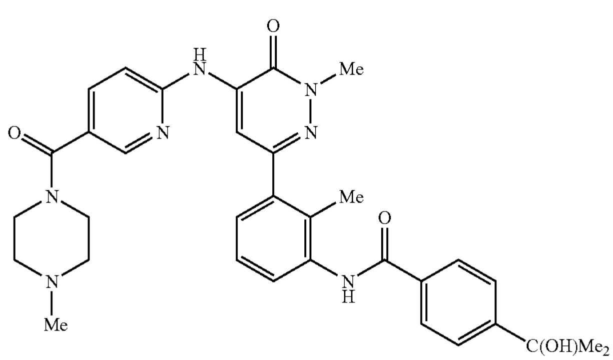 | 595 | 596 | 167.5-168.5 | 0.122 |

TABLE I-continued

| Cpd. # | Structure | mw | ms | mp | IC$_{50}$$^1$ (μM) |
|---|---|---|---|---|---|
| I-6 | 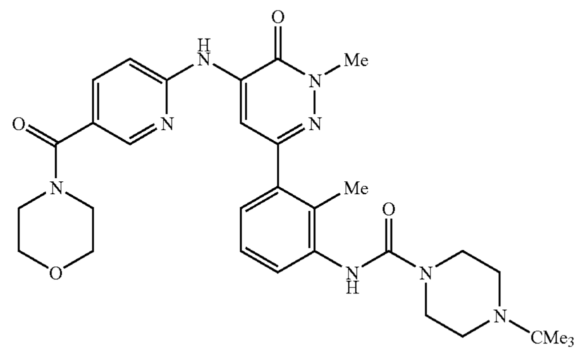 | 588 | 589 | 166.0-169.0 | 15.5 |
| I-7 | 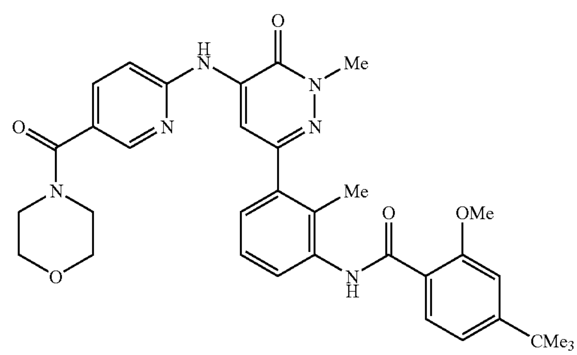 | 610 | 611 | 156.5-157.0 | 0.272 |
| I-8 | 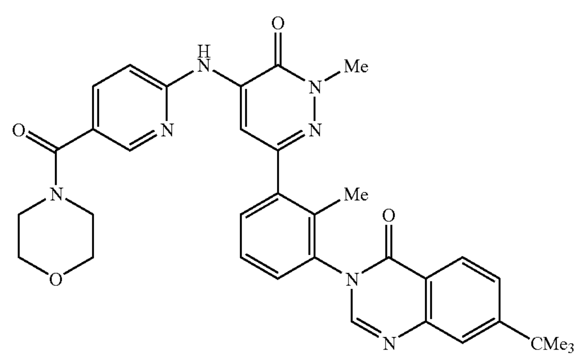 | 605 | 606 | 188.5-191.0 | 0.116 |
| I-9 | 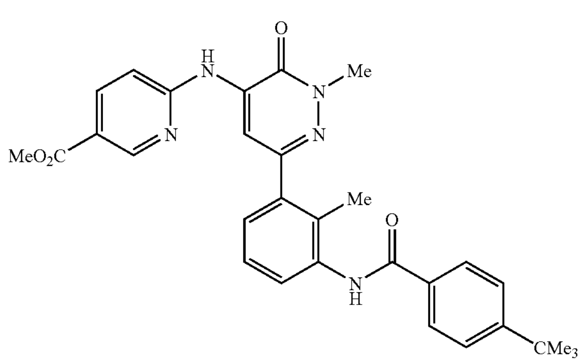 | 525 | 526 | | 0.16 |

TABLE I-continued

| Cpd. # | Structure | mw | ms | mp | IC$_{50}$[1] (μM) |
|---|---|---|---|---|---|
| I-10 | 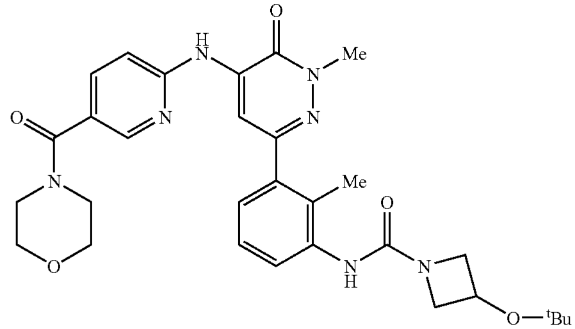 | 575 | 576 | 171.0-172.0 | 0.228 |
| I-11 | 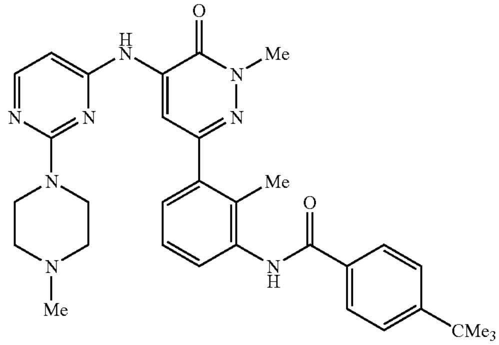 | 566 | 567 | 220.0-222.0 | 0.078 |
| I-12 | 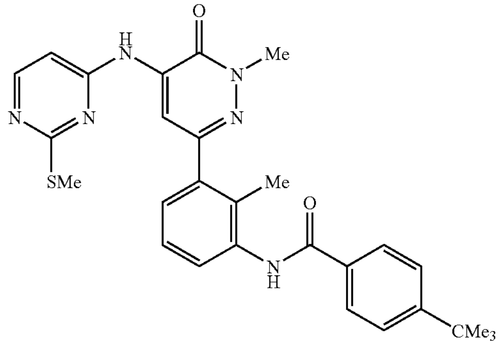 | 514 | 515 | 224.0-225.0 | 0.051 |
| I-13 | 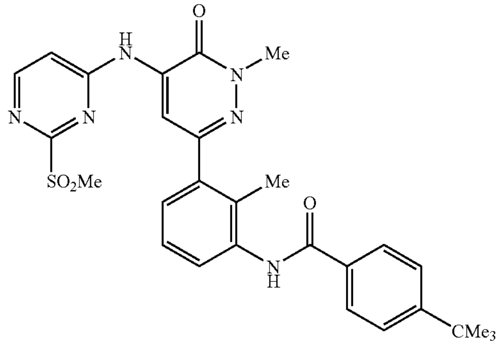 | 546 | 547 | | 1.064 |

TABLE I-continued

| Cpd. # | Structure | mw | ms | mp | IC$_{50}$[1] (μM) |
|---|---|---|---|---|---|
| I-14 | 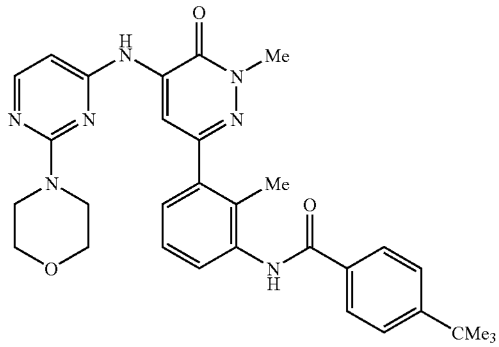 | 553 | 554 | 211.0-213.0 | 0.249 |
| I-15 | 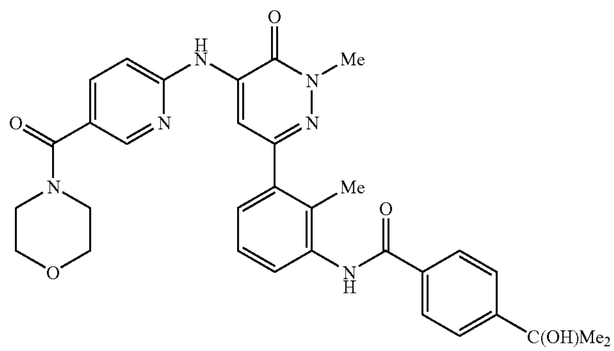 | 582 | 583 | | 0.374 |
| I-16 | 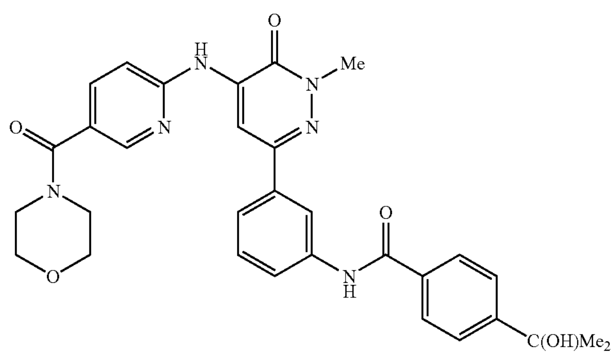 | 568 | 569 | 172.0-173.0 | 0.12 |
| I-17 | 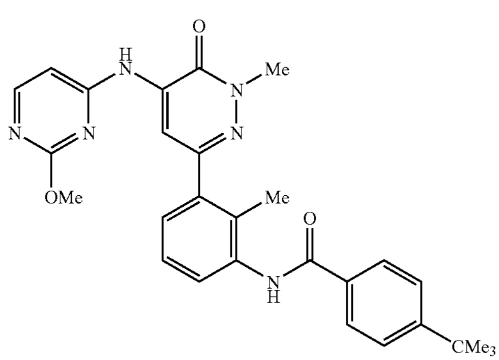 | 498 | 499 | 262.0-264.0 | 0.104 |

TABLE I-continued

| Cpd. # | Structure | mw | ms | mp | IC$_{50}$$^1$ (μM) |
|---|---|---|---|---|---|
| I-18 | 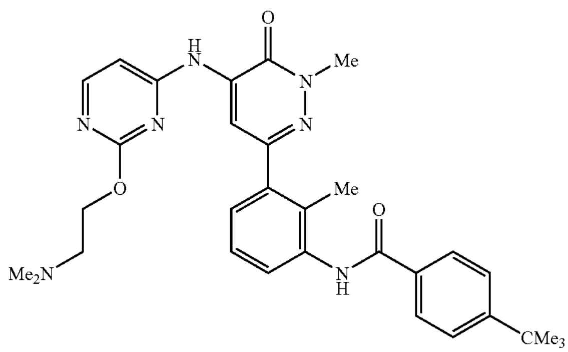 | 555 | 556 | 188.0-189.0 | 0.326 |
| I-19 | 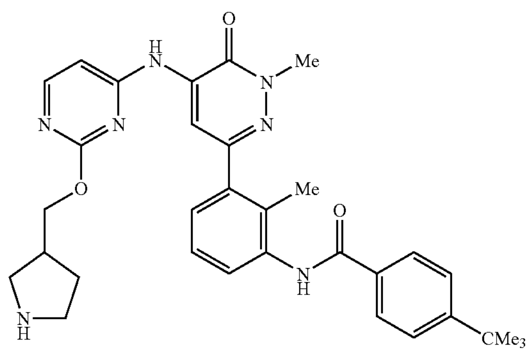 | 567 | 568 | | 0.143 |
| I-20 | 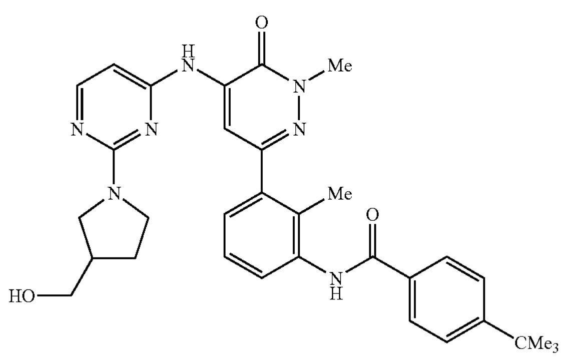 | 567 | 568 | 210.0-211.0 | 0.125 |
| I-21 | 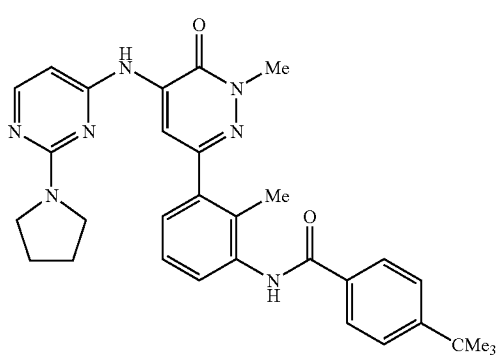 | 537 | 538 | 193.0-195.0 | 0.354 |

TABLE I-continued

| Cpd. # | Structure | mw | ms | mp | IC$_{50}$¹ (μM) |
|---|---|---|---|---|---|
| I-22 | 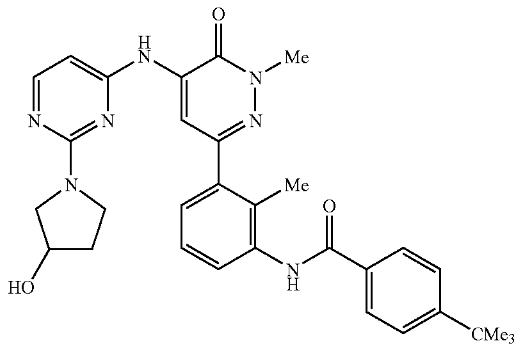 | 553 | 554 | | 0.052 |
| I-23 | 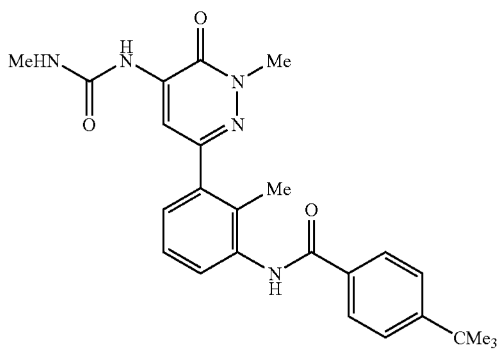 | 447 | 448 | 287.0-288.0 | 0.101 |
| I-24 | 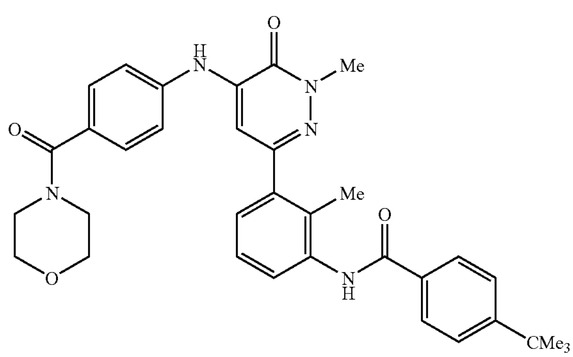 | 579 | 580 | 157.0-158.0 | 0.11 |
| I-25 | 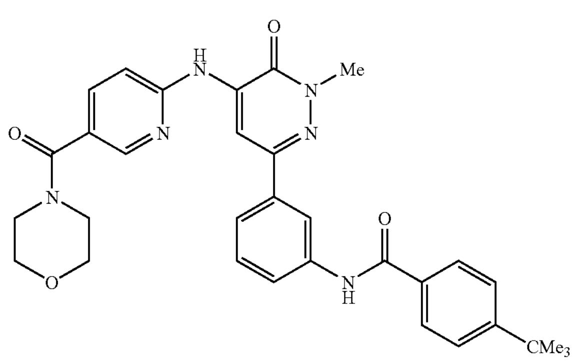 | 566 | 567 | 229.0-230.0 | 0.12 |

TABLE I-continued

| Cpd. # | Structure | mw | ms | mp | IC$_{50}$$^1$ (μM) |
|---|---|---|---|---|---|
| I-26 | 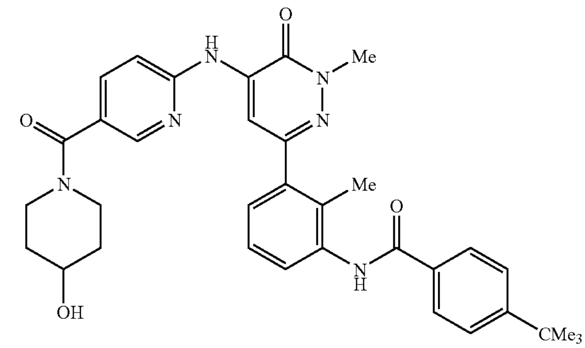 | 593 | 594 | | 0.045 |
| I-27 | 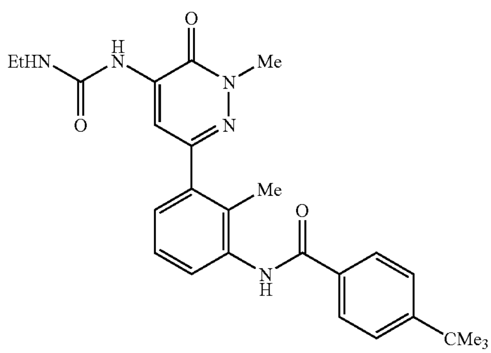 | 461 | 462 | 278.0-279.0 | 0.122 |
| I-28 | 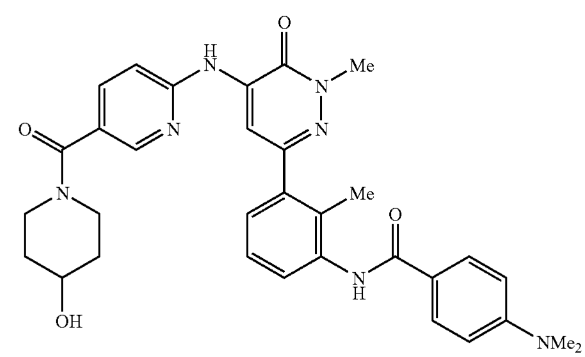 | 581 | 582 | | 0.034 |
| I-29 | 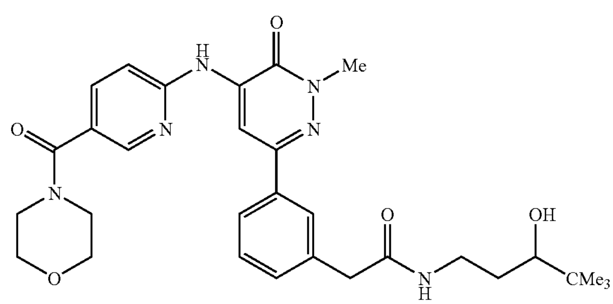 | 562 | 563 | | 1.715 |

TABLE I-continued

| Cpd. # | Structure | mw | ms | mp | IC$_{50}$$^1$ (μM) |
|---|---|---|---|---|---|
| I-30 | 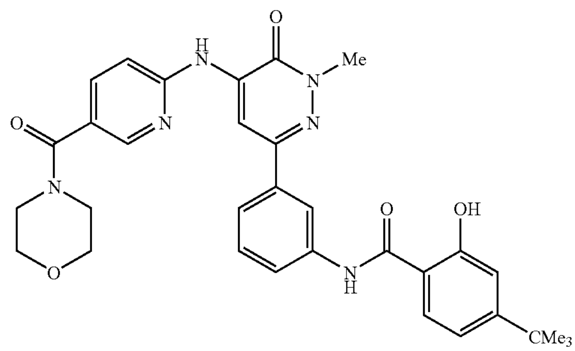 | 596 | 597 | 216.0-217.0 | 0.059 |
| I-31 | 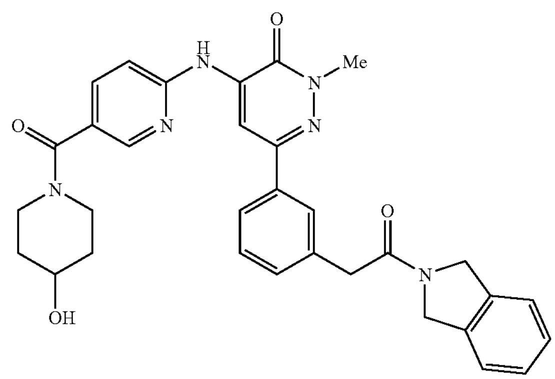 | 564 | 565 | | 0.155 |
| I-32 | 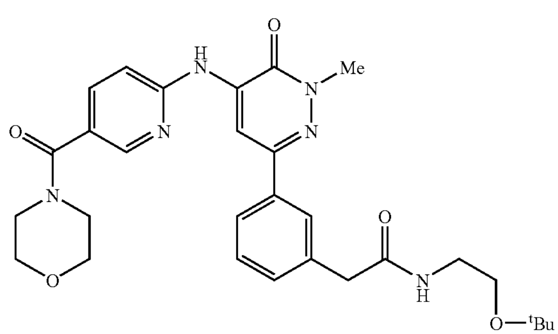 | 548 | 549 | 220.0-221.0 | 0.82 |
| I-33 | 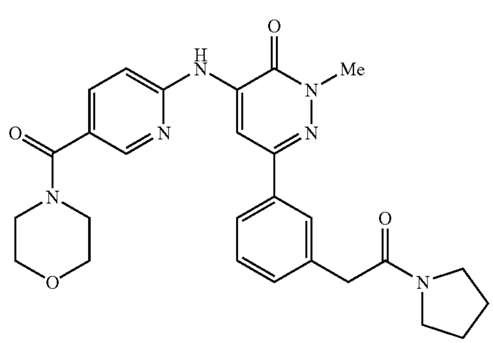 | 502 | 503 | 117.0-118.0 | 16.35 |

TABLE I-continued

| Cpd. # | Structure | mw | ms | mp | IC$_{50}$$^1$ (μM) |
|---|---|---|---|---|---|
| I-34 | 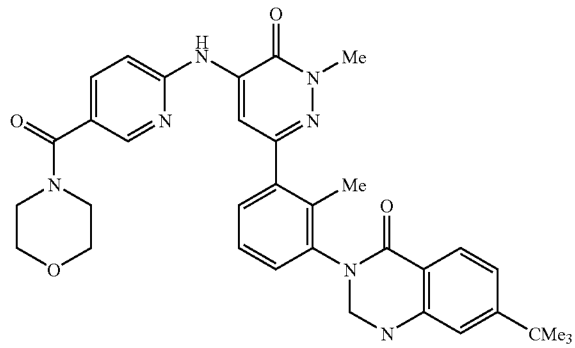 | 607 | 608 | | |
| I-35 | 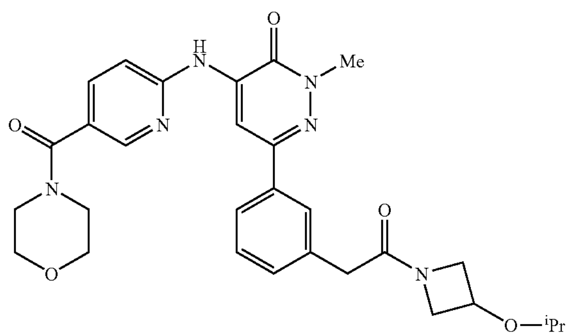 | 546 | 547 | 92.0-93.0 | 0.418 |
| I-36 | 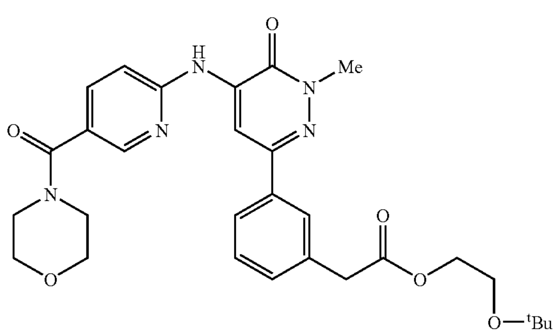 | 549 | 550 | 80.0-81.0 | 2.2 |
| I-37 | 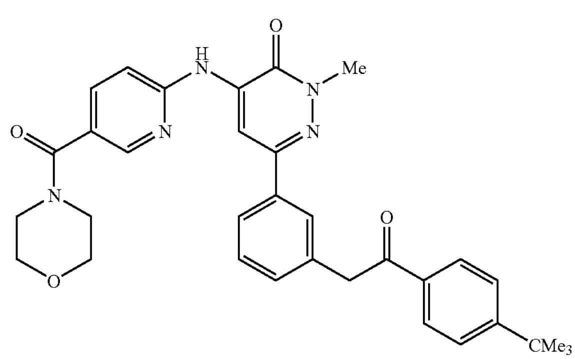 | 565 | 566 | | 0.206 |

TABLE I-continued

| Cpd. # | Structure | mw | ms | mp | IC$_{50}$$^1$ (μM) |
|---|---|---|---|---|---|
| I-38 | 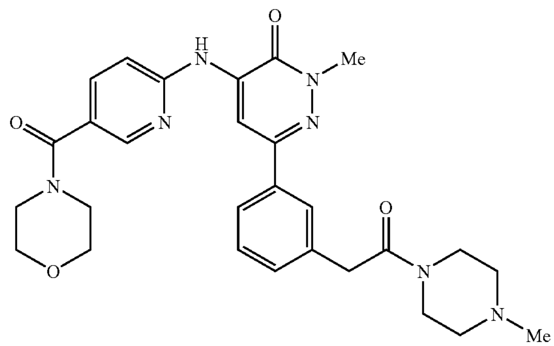 | 573 | 574 | 234.0-236.0 | 33.5 |
| I-39 | 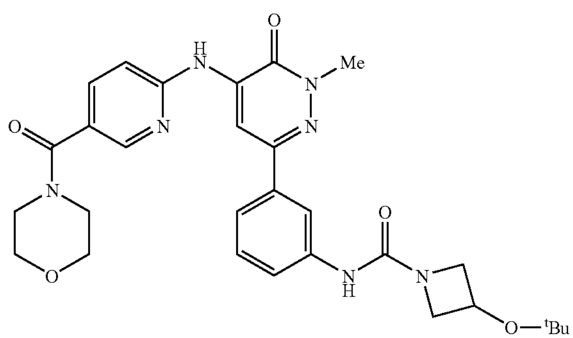 | 560 | 561 | 134.0-135.0 | 0.138 |
| I-40 | 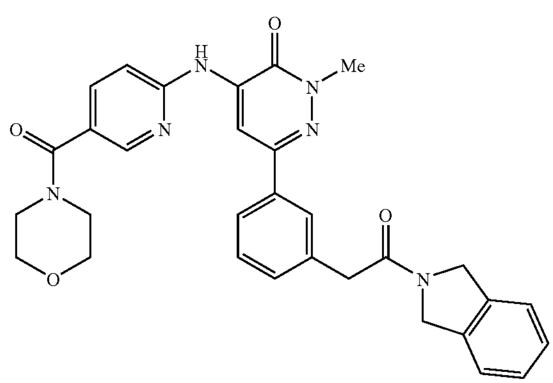 | 550 | 551 | 179.0-180.0 | 0.68 |
| I-41 | 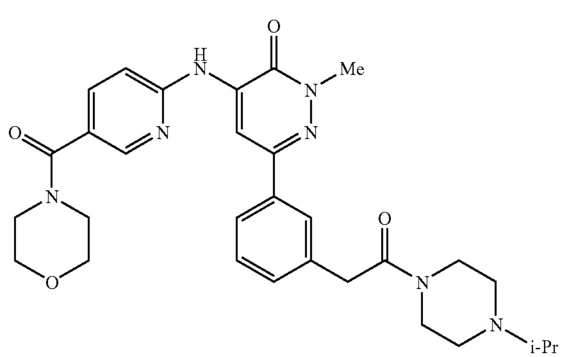 | 559 | 560 | 209.0-210.0 | 6.245 |

TABLE I-continued

| Cpd. # | Structure | mw | ms | mp | IC$_{50}$[1] (μM) |
|---|---|---|---|---|---|
| I-42 | 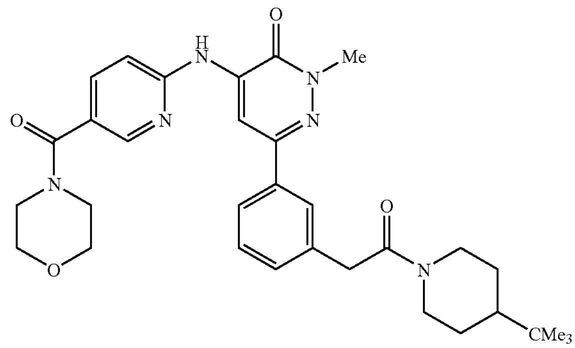 | 572 | 573 | 231.0-232.0 | 2.345 |
| I-43 | 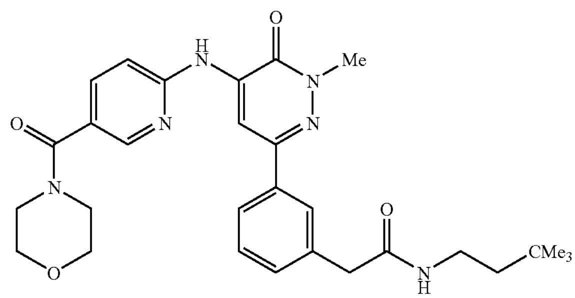 | 532 | 533 | 138.0-139.0 | 6.29 |
| I-44 | 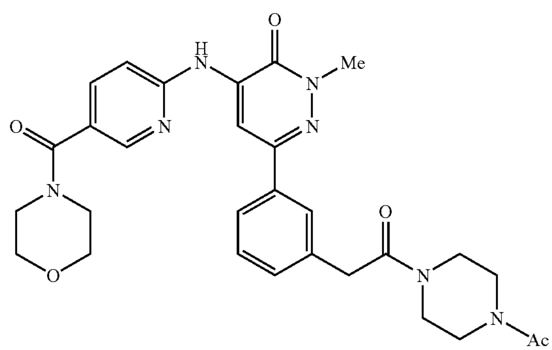 | 559 | 560 | | 61.6 |
| I-45 | 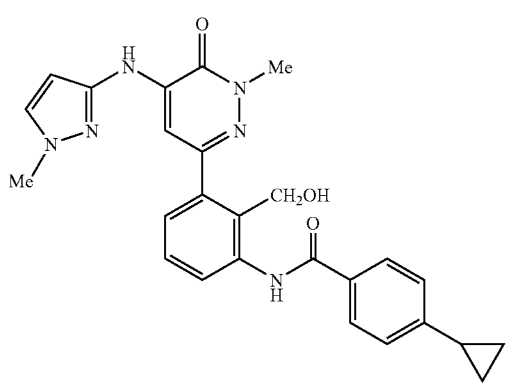 | 470 | 471 | | |

TABLE I-continued

| Cpd. # | Structure | mw | ms | mp | IC$_{50}$$^1$ (μM) |
|---|---|---|---|---|---|
| I-46 | 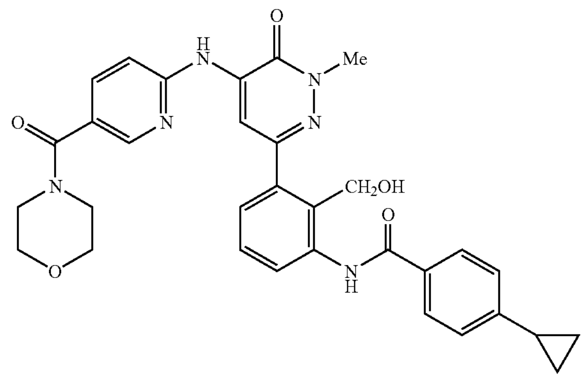 | 580 | 581 | | <0.01 |

$^1$. Bruton's tyrosine kinase Assay (Example 34)

TABLE II depicts examples of pyridinone compounds according to formula I wherein $X^1$ is CH.

TABLE II

| Cpd. # | Structure | mw | ms | mp | IC$_{50}$$^1$ (μM) |
|---|---|---|---|---|---|
| II-4 | 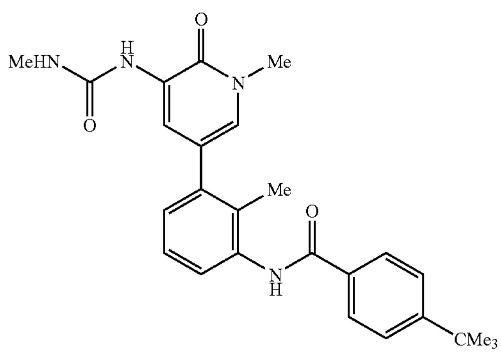 | 446 | 447 | 262.0-264.0 | |
| II-5 | 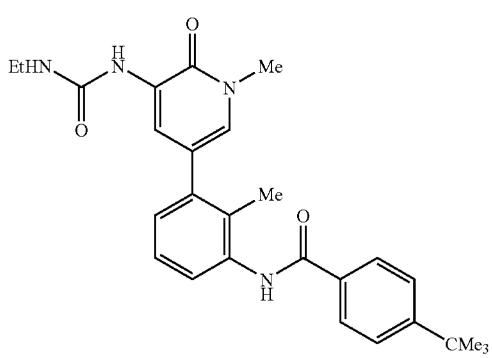 | 460 | 461 | 215.0-216.0 | 0.013 |

TABLE II-continued

| Cpd. # | Structure | mw | ms | mp | IC$_{50}$[1] ($\mu$M) |
|---|---|---|---|---|---|
| II-6 | i-PrHN-C(O)NH-[1-methyl-2-oxo-pyridin-3-yl]-[2-methyl-phenyl]-NH-C(O)-[4-CMe$_3$-phenyl] | 474 | 475 | 185.0-186.0 | 0.308 |
| II-7 | F$_3$C-CH$_2$-NH-C(O)NH-[1-methyl-2-oxo-pyridin-3-yl]-[2-methyl-phenyl]-NH-C(O)-[4-CMe$_3$-phenyl] | 514 | 515 | 258.0-259.0 | 0.867 |
| II-8 | PhHN-C(O)NH-[1-methyl-2-oxo-pyridin-3-yl]-[2-methyl-phenyl]-NH-C(O)-[4-CMe$_3$-phenyl] | 508 | 509 | 219.0-220.0 | 7.325 |
| II-9 | PhCH$_2$NH-C(O)NH-[1-methyl-2-oxo-pyridin-3-yl]-[2-methyl-phenyl]-NH-C(O)-[4-CMe$_3$-phenyl] | 522 | 523 | 169.0-170.0 | 1.24 |

TABLE II-continued

| Cpd. # | Structure | mw | ms | mp | IC$_{50}$[1] (μM) |
|---|---|---|---|---|---|
| II-10 | 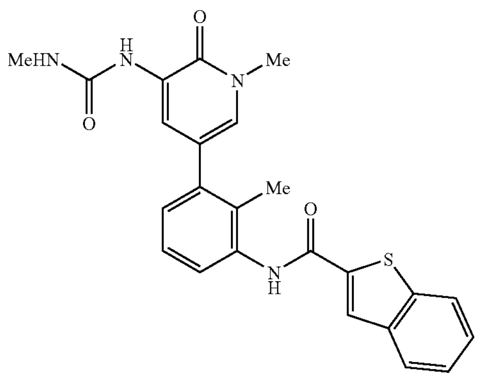 | 446 | 447 | 286.0-287.0 | 0.131 |
| II-11 | 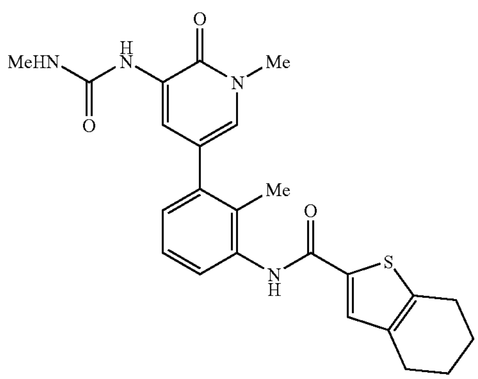 | 450 | 451 | 254.0-255.0 | 0.04 |
| II-12 | 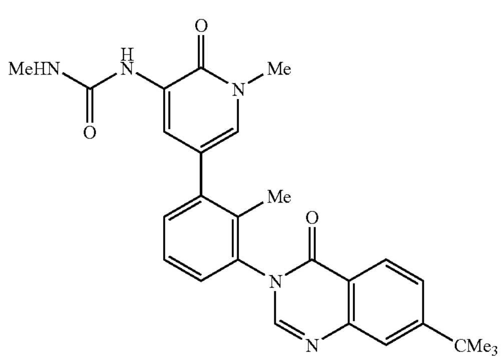 | 471 | 472 | | 0.112 |

TABLE II-continued

| Cpd. # | Structure | mw | ms | mp | IC$_{50}$[1] (μM) |
|---|---|---|---|---|---|
| II-13 | 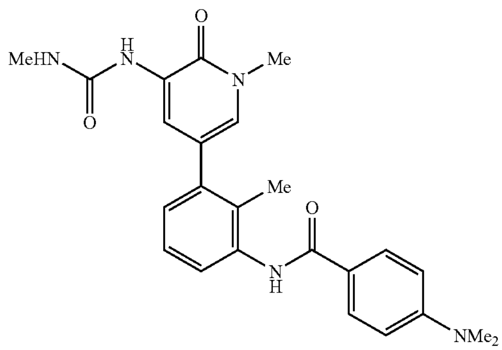 | 433 | 434 | 291.0-292.0 | 0.096 |
| II-14 | 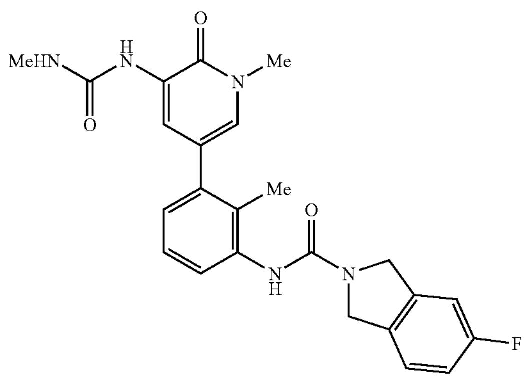 | 449 | 450 | 262.0-263.0 | 1.95 |
| II-15 | 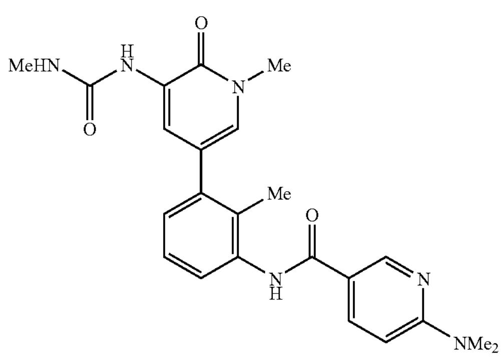 | 434 | 435 | | 2.31 |
| II-16 | 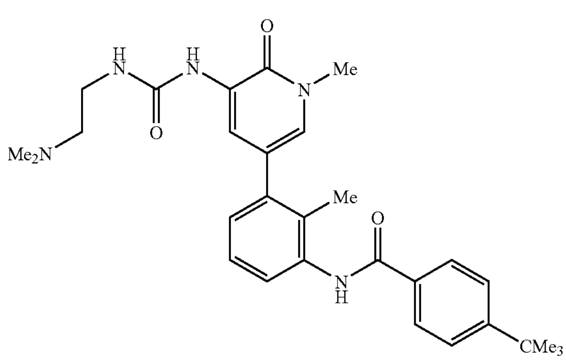 | 503 | 504 | 164.0-165.0 | 0.129 |

TABLE II-continued

| Cpd. # | Structure | mw | ms | mp | IC$_{50}$[1] (μM) |
|---|---|---|---|---|---|
| II-17 | 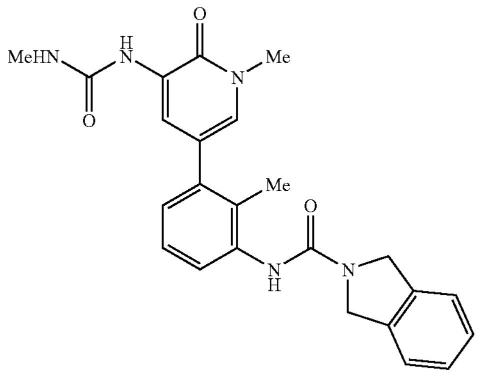 | 431 | 432 | 264.0-265.0 | 0.666 |
| II-18 | 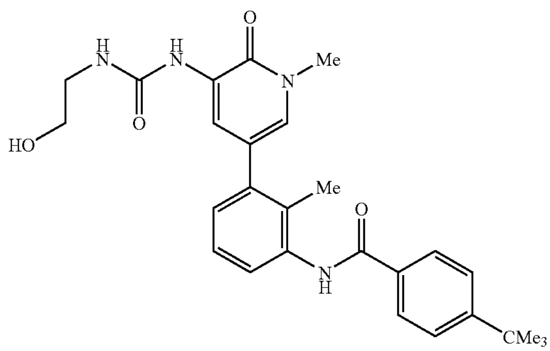 | 476 | 477 | 220.0-221.0 | 0.038 |
| II-19 | 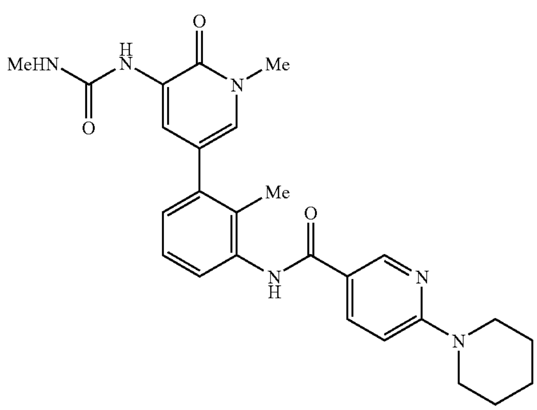 | 474 | 475 | | 0.31 |
| II-21 | 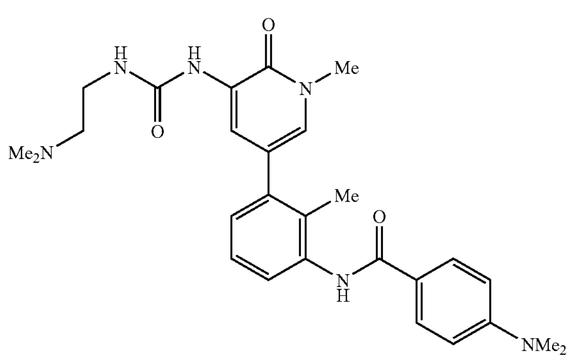 | 567 | 568 | | 0.039 |

TABLE II-continued

| Cpd. # | Structure | mw | ms | mp | IC$_{50}$[1] (μM) |
|---|---|---|---|---|---|
| II-22 | 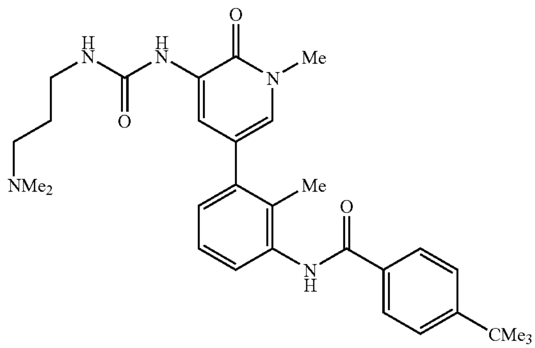 | 517 | 518 | 194.0–195.0 | 0.029 |
| II-23 | 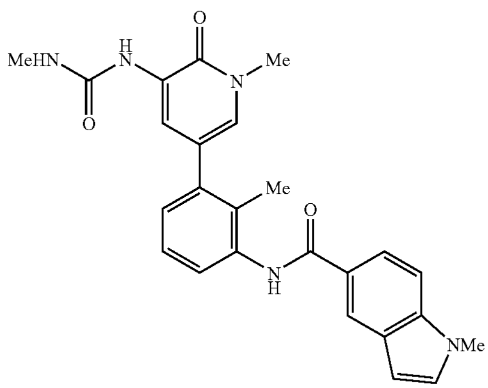 | 443 | 444 | | 9.93 |
| II-27 | 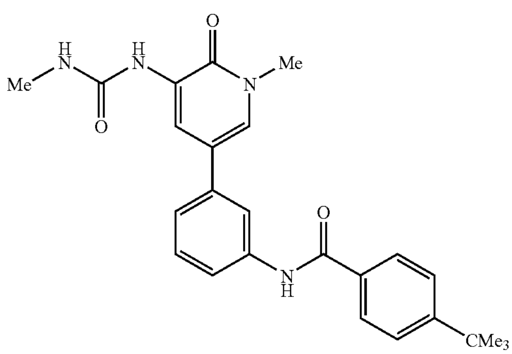 | 432 | 433 | | 0.131 |
| II-28 | 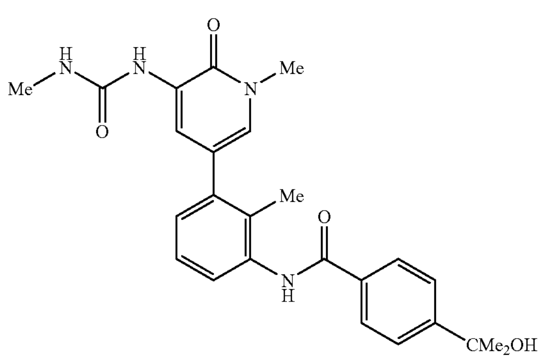 | 448 | 449 | | 0.23 |

TABLE II-continued

| Cpd. # | Structure | mw | ms | mp | IC$_{50}$$^{1}$ (μM) |
|---|---|---|---|---|---|
| II-29 | 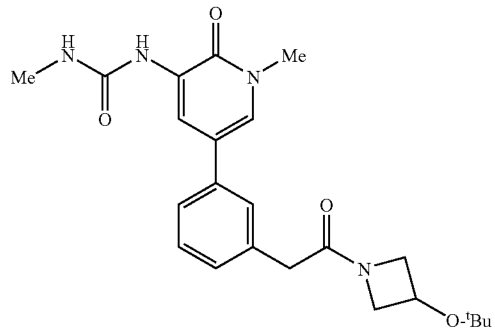 | 426 | 427 | 125.0-126.0 | 1.405 |
| II-30 | 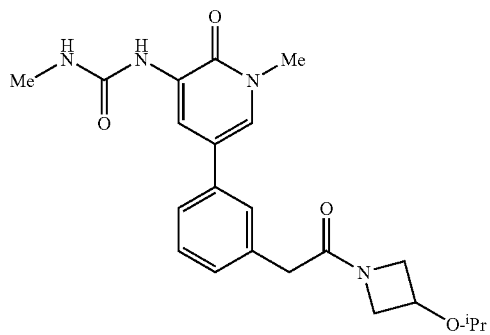 | 412 | 413 | 118.0-119.0 | 4.37 |
| II-31 | 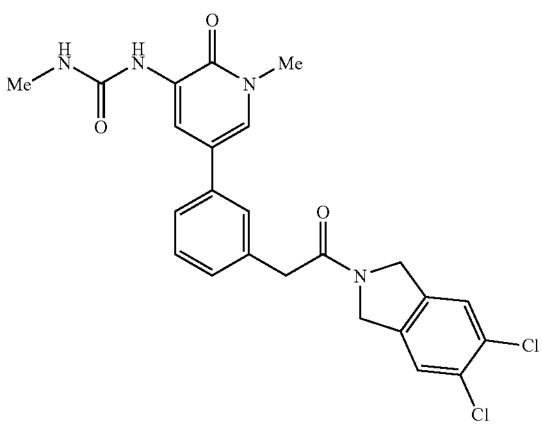 | 485 | 486 | | 14.85 |
| II-42 | 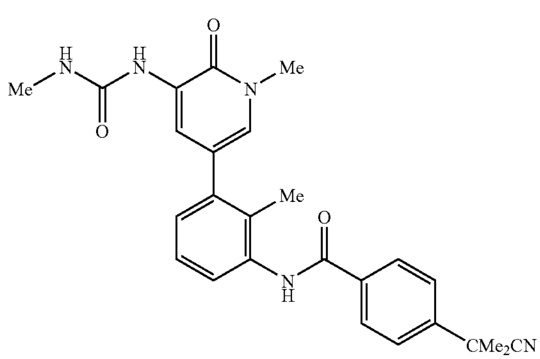 | 457 | 458 | | 0.681 |

TABLE II-continued

| Cpd. # | Structure | mw | ms | mp | IC$_{50}$[1] (μM) |
|---|---|---|---|---|---|
| II-45 | 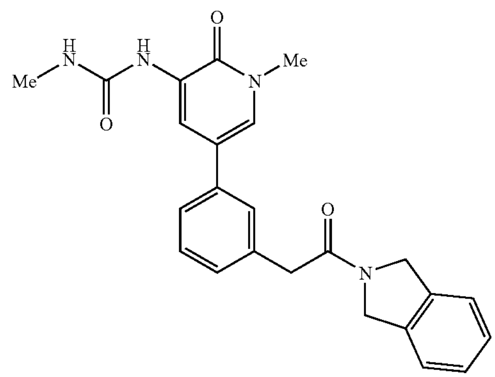 | 416 | 417 | 251.0-252.0 | 1.563 |
| II-46 | 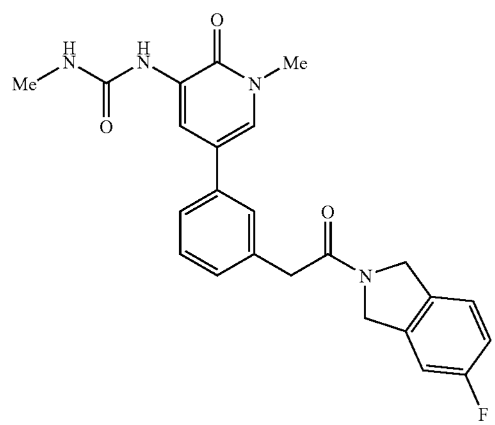 | 434 | 435 | | 3.44 |
| II-47 | 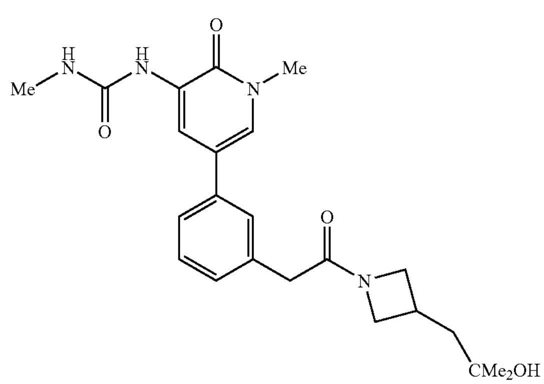 | 426 | 427 | 113.0-114.0 | 54.65 |
| II-49 | 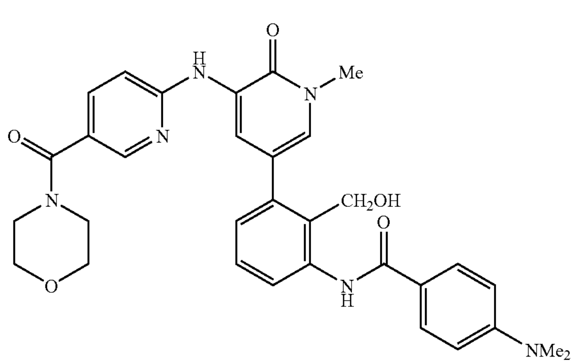 | 582 | 583 | | <0.01 |

TABLE II-continued

| Cpd. # | Structure | mw | ms | mp | IC$_{50}$[1] (μM) |
|---|---|---|---|---|---|
| II-50 | 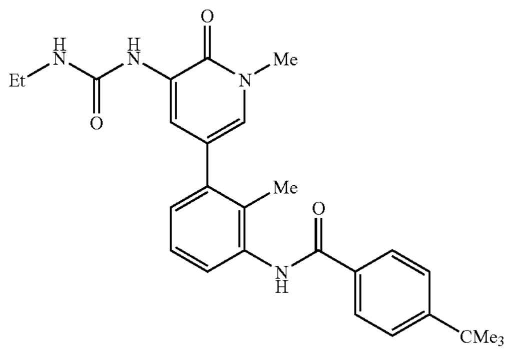 | 446 | 447 | | <0.01 |
| II-51 | 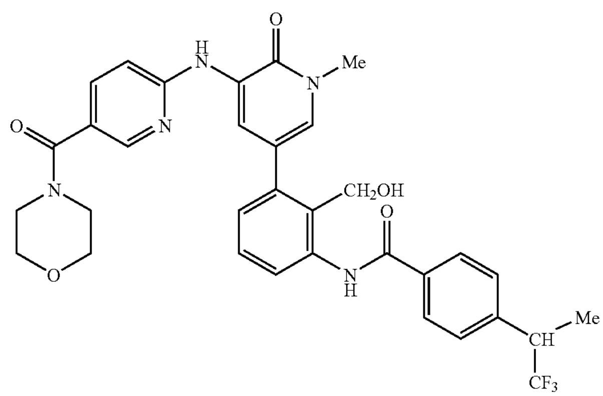 | 635 | 636 | | |
| II-52 | 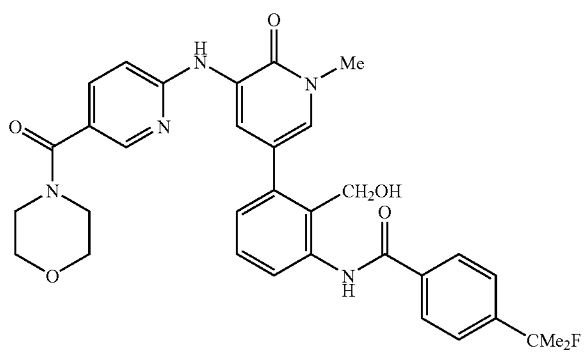 | 599 | 600 | | <0.01 |
| II-53 | 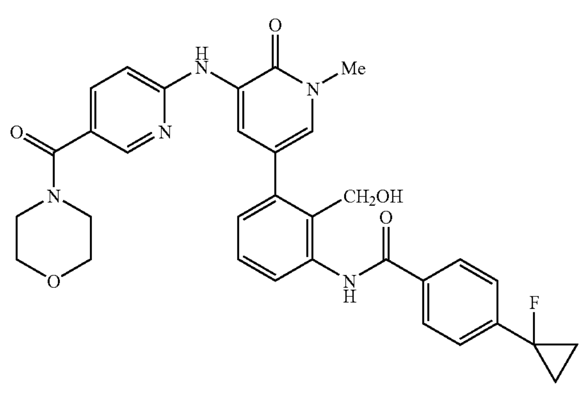 | 597 | 598 | | |

TABLE II-continued

| Cpd. # | Structure | mw | ms | mp | IC$_{50}$[1] (μM) |
|---|---|---|---|---|---|
| II-54 | 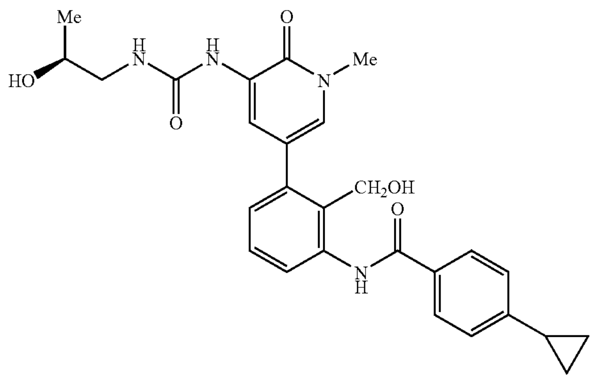 | 490 | 491 | | 0.068 |
| II-55 | 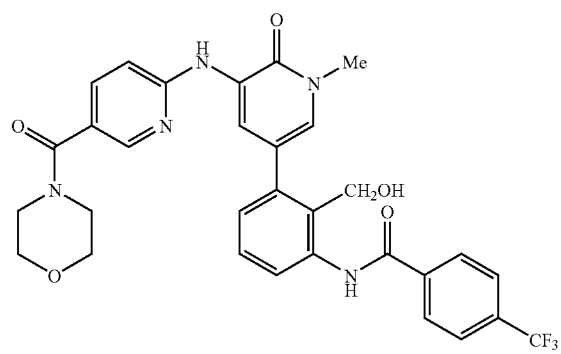 | 607 | 608 | | 0.085 |
| II-56 | 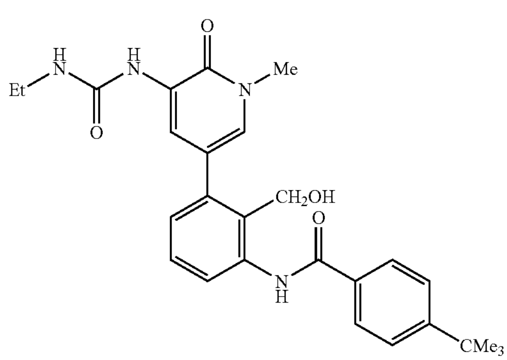 | 476 | 477 | | <0.01 |
| II-57 | 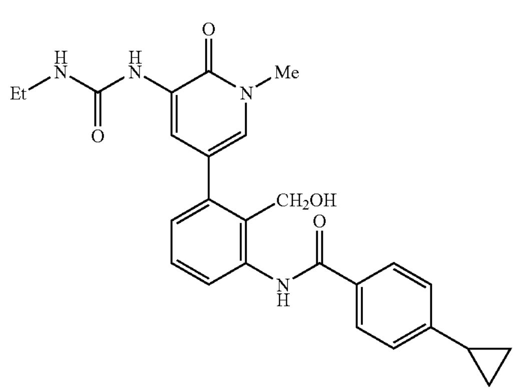 | 474 | 475 | 201.0-203.0 | <0.01 |

TABLE II-continued

| Cpd. # | Structure | mw | ms | mp | IC$_{50}$[1] (μM) |
|---|---|---|---|---|---|
| II-58 | 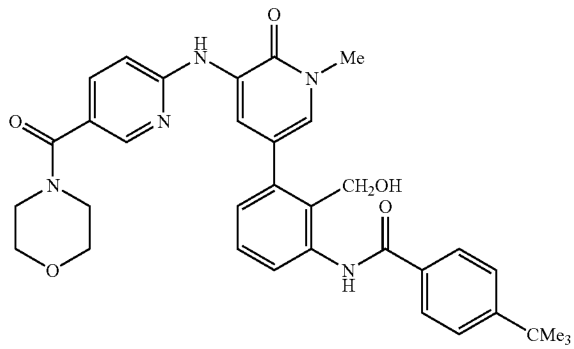 | 595 | 596 | | <0.01 |
| II-59 | 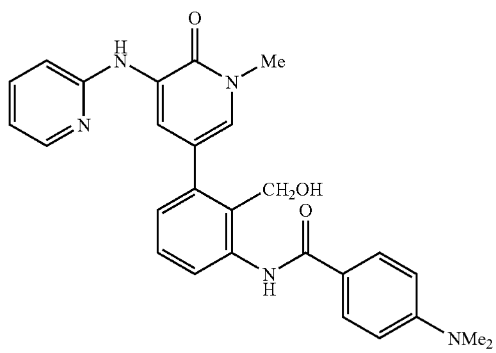 | 469 | 470 | | 0.02 |
| II-60 | 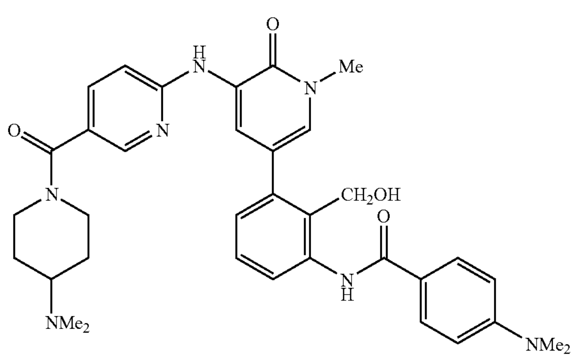 | 623 | 624 | | <0.01 |
| II-61 | 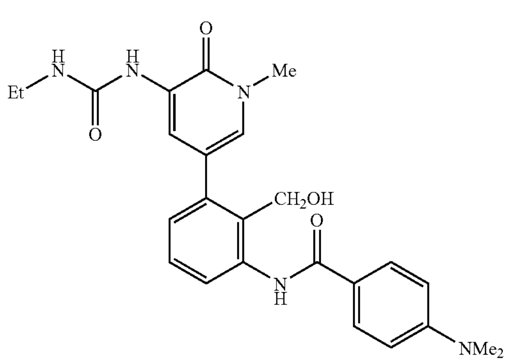 | 463 | 464 | | — |

TABLE II-continued

| Cpd. # | Structure | mw | ms | mp | IC$_{50}$[1] (μM) |
|---|---|---|---|---|---|
| II-62 | 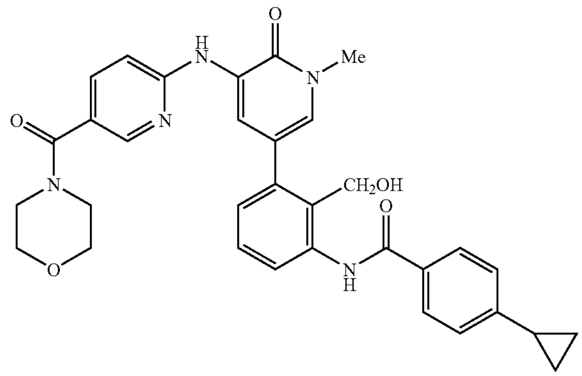 | 579 | 580 | | — |
| II-63 | 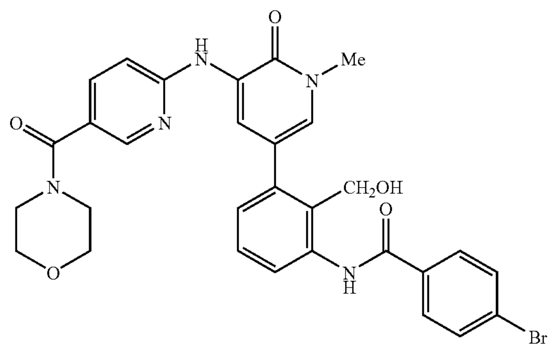 | 618 | 618, 620 | | 0.031 |
| II-64 | 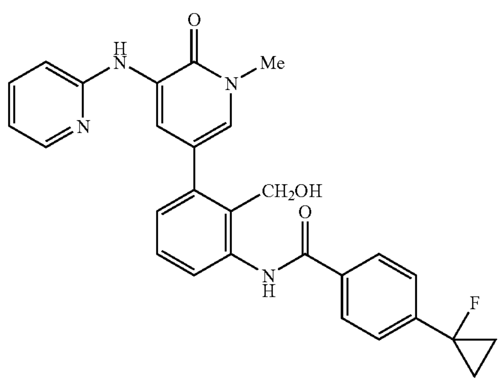 | 484 | 485 | | 0.05 |
| II-65 | 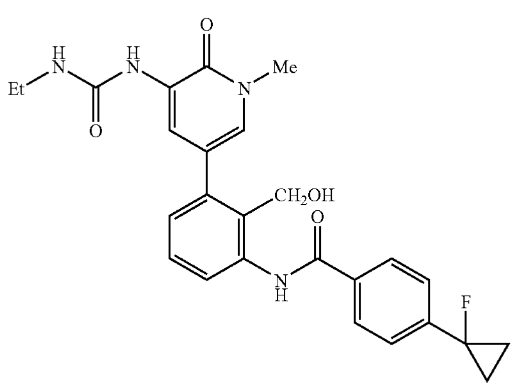 | 478 | 479 | | 0.015 |

TABLE II-continued

| Cpd. # | Structure | mw | ms | mp | IC$_{50}$[1] (μM) |
|---|---|---|---|---|---|
| II-66 | 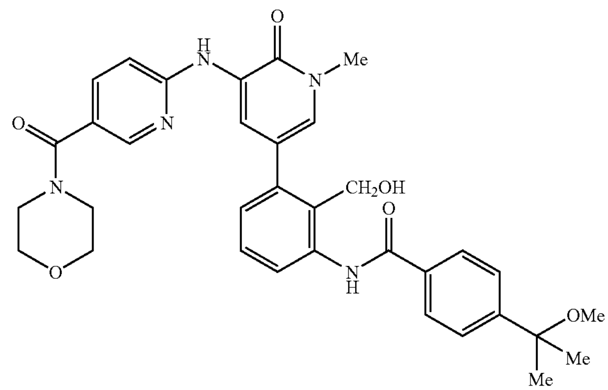 | 611 | 612 | | 0.024 |
| II-67 | 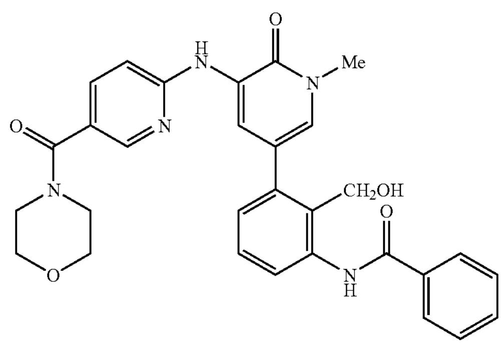 | 539 | 540 | | 0.77 |
| II-68 | 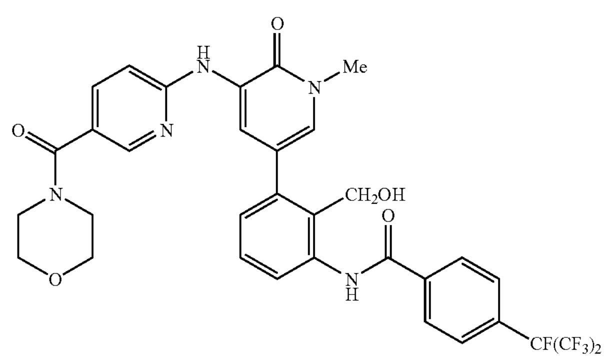 | 707 | 708 | | 0.071 |
| II-69 | 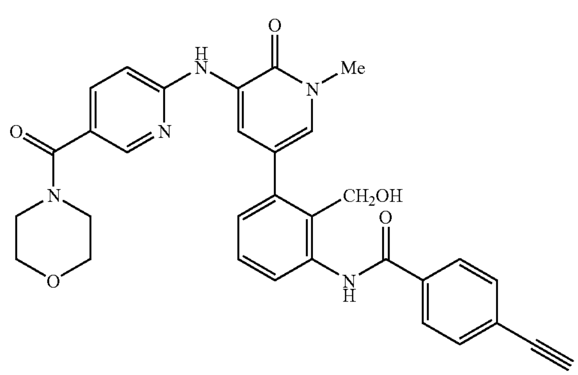 | 563 | 564 | | 0.076 |

TABLE II-continued

| Cpd. # | Structure | mw | ms | mp | IC$_{50}$[1] (μM) |
|---|---|---|---|---|---|
| II-70 | 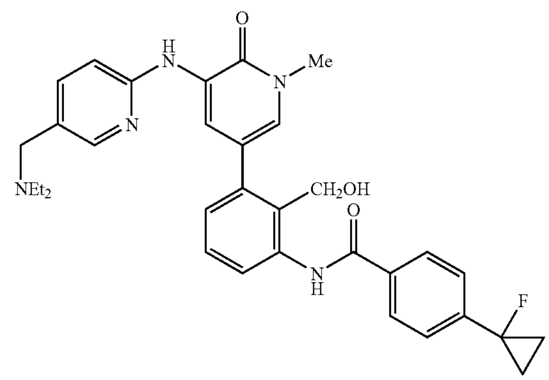 | 569 | 570 | 203.0-204.0 | <0.01 |
| II-71 | 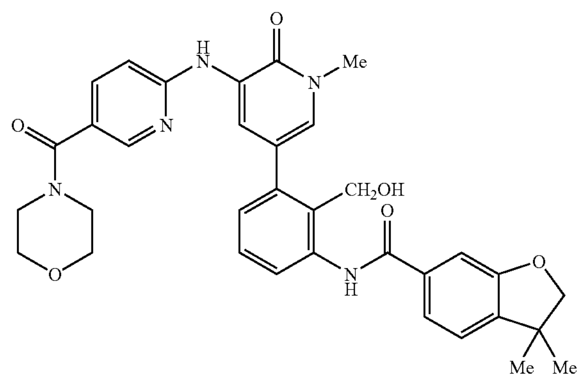 | 609 | 610 | | <0.01 |
| II-72 | 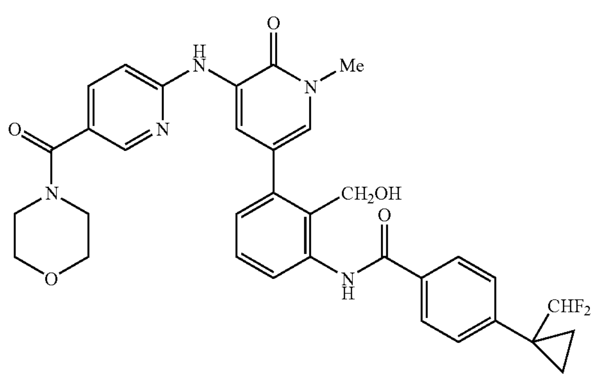 | 629 | 630 | | <0.01 |
| II-73 | 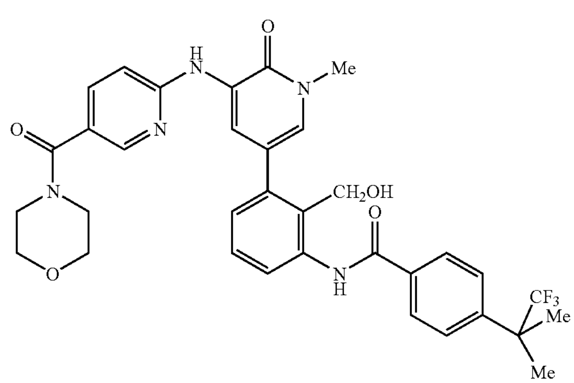 | 649 | 650 | | |

TABLE II-continued
| Cpd. # | Structure | mw | ms | mp | IC$_{50}$[1] (μM) |
|---|---|---|---|---|---|
| II-74 | 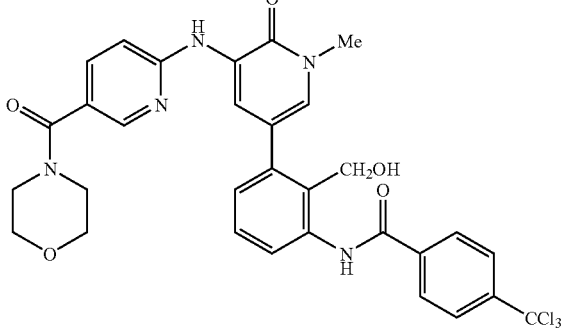 | 656 | 656, 658 | | 0.05 |
| II-75 | 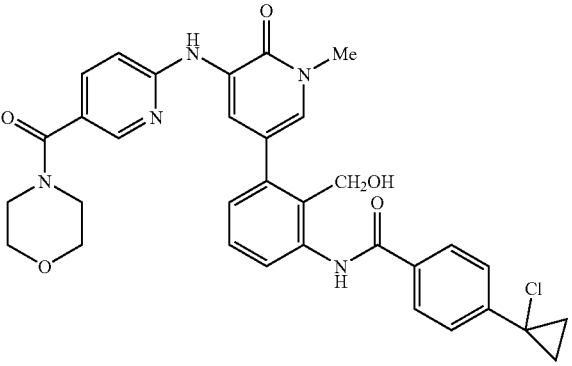 | 614 | 615 | | <0.01 |
| II-76 | 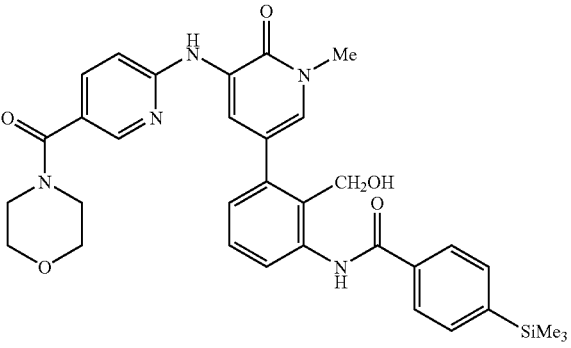 | 611 | 612 | | 0.04 |
| II-77 | 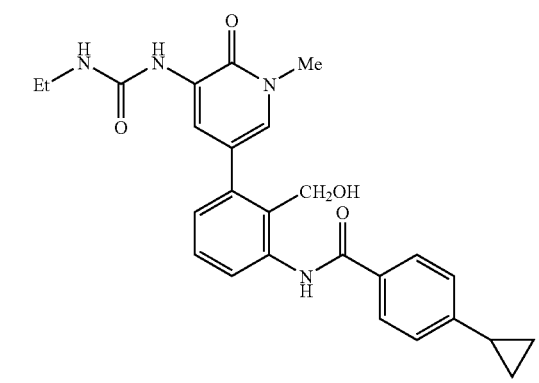 | 460 | 461 | | 0.04 |

TABLE II-continued
| Cpd. # | Structure | mw | ms | mp | IC$_{50}$$^1$ (μM) |
|---|---|---|---|---|---|
| II-78 | 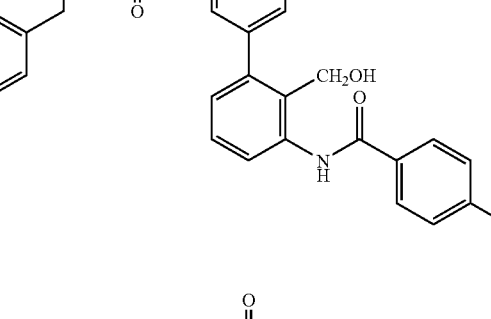 | 537 | 538 | | 0.214 |
| II-79 | 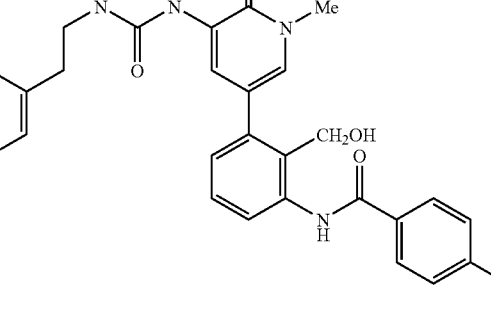 | 537 | 538 | | 0.16 |
| II-80 | 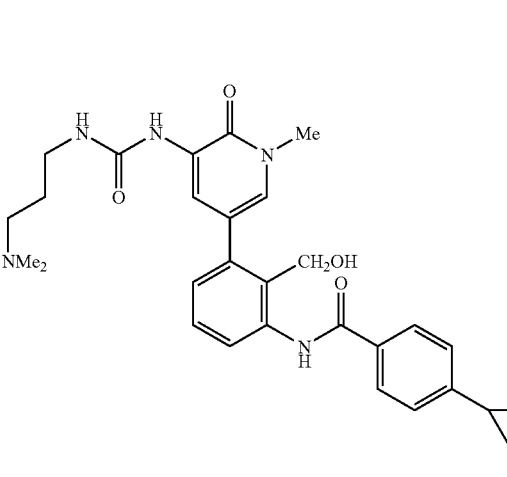 | 517 | 518 | | 0.043 |
| II-81 | 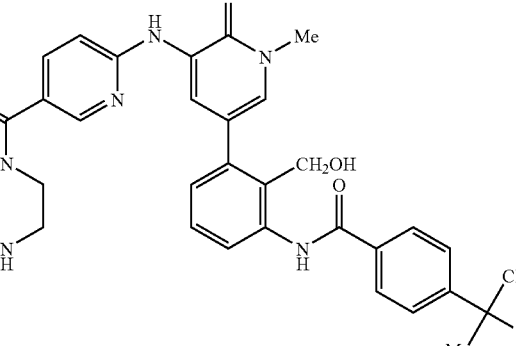 | 648 | 649 | | <0.01 |

TABLE II-continued

| Cpd. # | Structure | mw | ms | mp | IC$_{50}$[1] (μM) |
|---|---|---|---|---|---|
| II-82 | 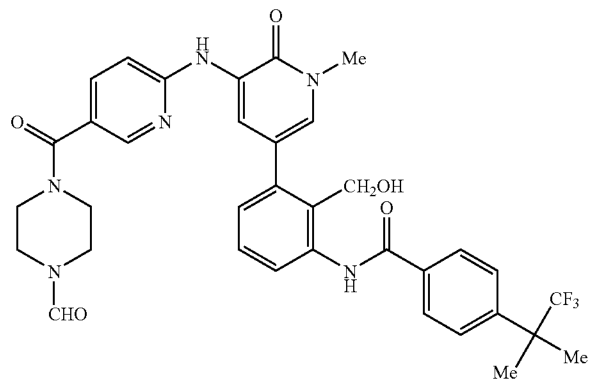 | 676 | 677 | | |
| II-83 | 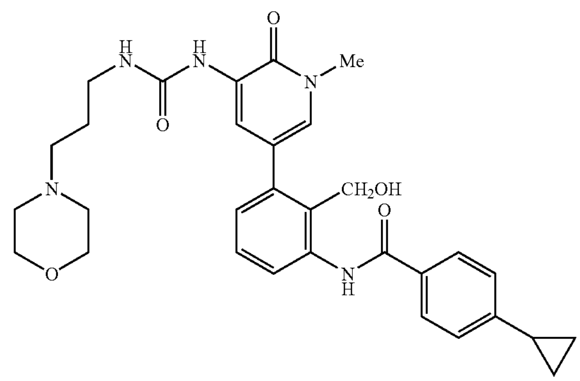 | 559 | 560 | | 0.054 |
| II-84 | 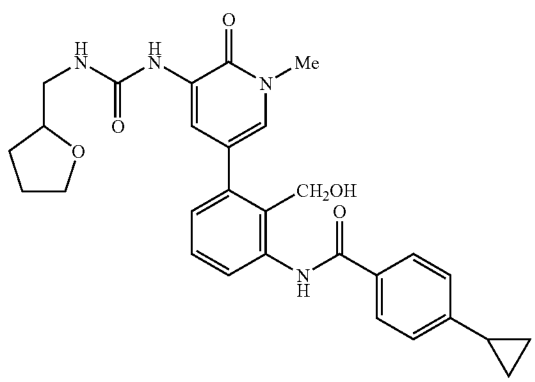 | 516 | 517 | | 0.06 |
| II-85 | 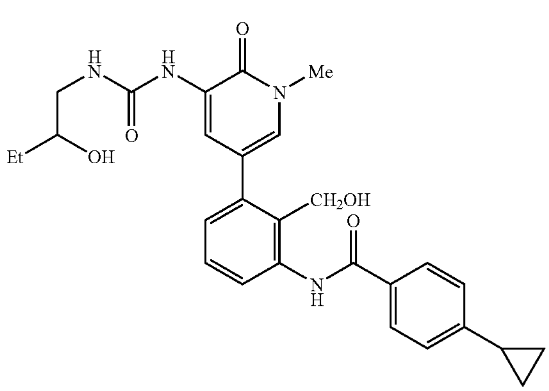 | 504 | 505 | | 0.046 |

TABLE II-continued

| Cpd. # | Structure | mw | ms | mp | IC$_{50}$$^1$ (μM) |
|---|---|---|---|---|---|
| II-86 | 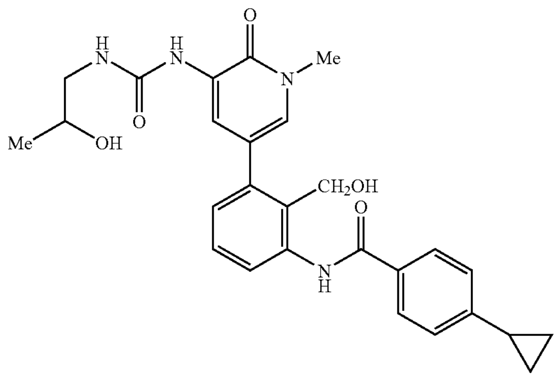 | 490 | 491 | | 0.068 |
| II-87 | 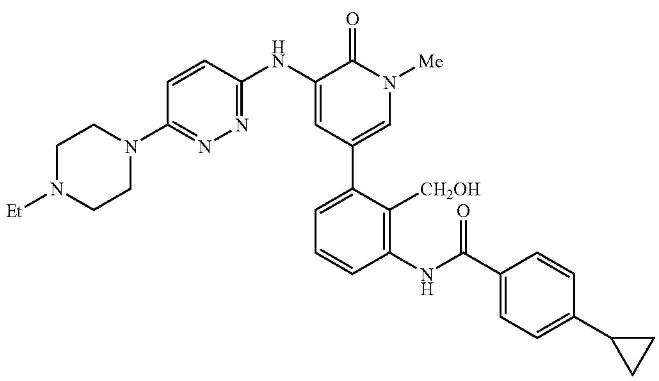 | 579 | 580 | | |
| II-88 | 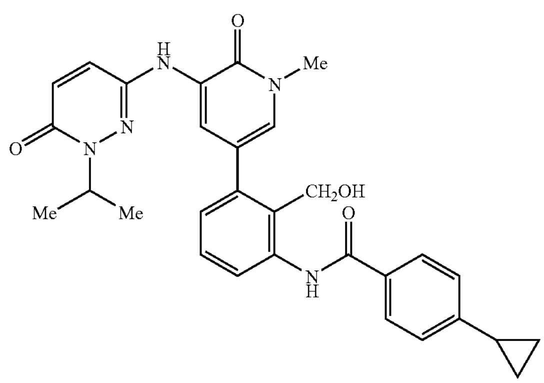 | 525 | 526 | | 0.14 |
| II-89 | 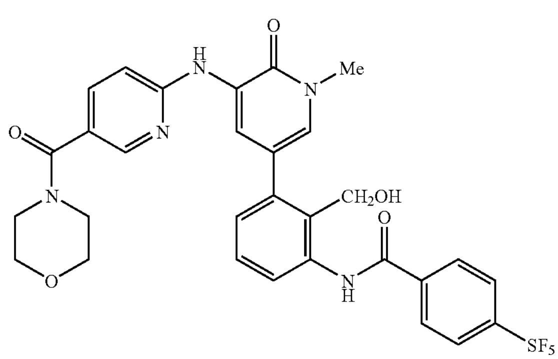 | 665 | 666 | | <0.01 |

TABLE II-continued
| Cpd. # | Structure | mw | ms | mp | IC$_{50}$[1] (µM) |
|---|---|---|---|---|---|
| II-90 | 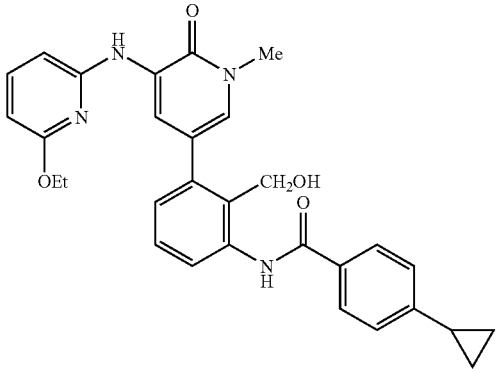 | 510 | 511 | | 0.081 |
| II-91 | 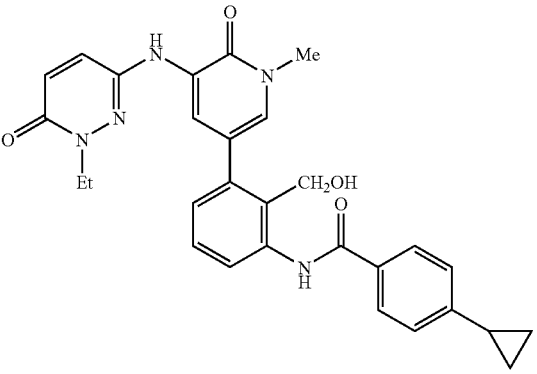 | 511 | 512 | | 0.066 |
| II-92 | 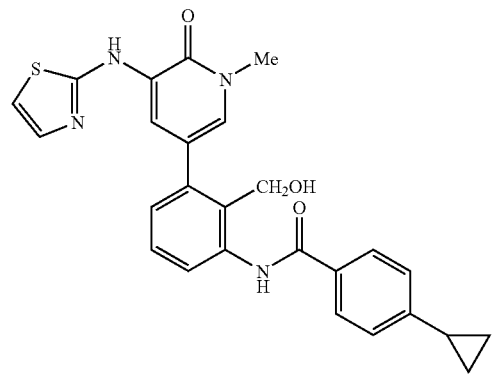 | 472 | 473 | | 0.034 |
| II-93 | 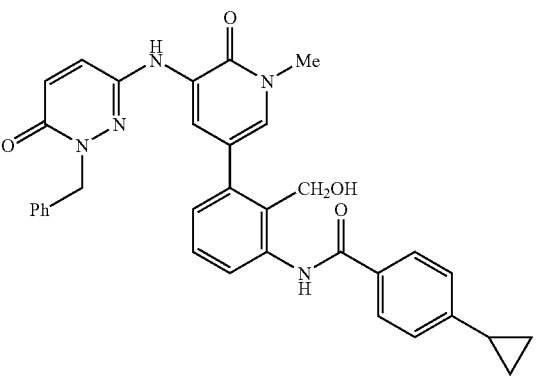 | 573 | 574 | | 0.298 |

TABLE II-continued
| Cpd. # | Structure | mw | ms | mp | IC$_{50}$[1] (μM) |
|---|---|---|---|---|---|
| II-94 | 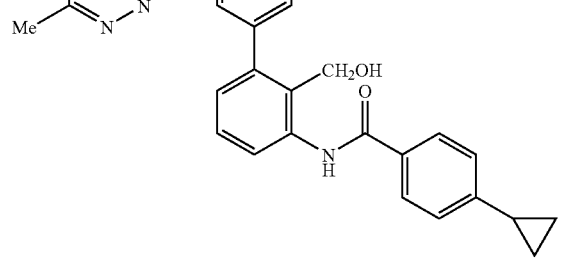 | 481 | 482 | | 0.024 |
| II-95 | 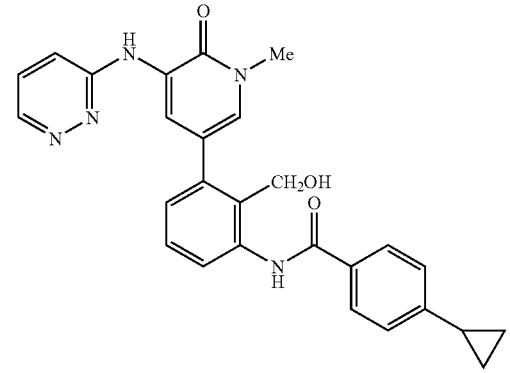 | 467 | 468 | | 0.02 |
| II-96 | 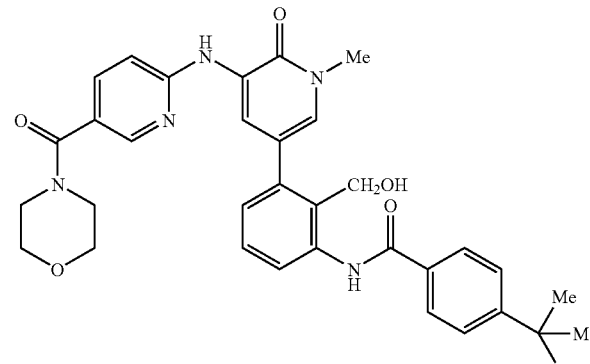 | 606 | 607 | | <0.01 |
| II-97 | 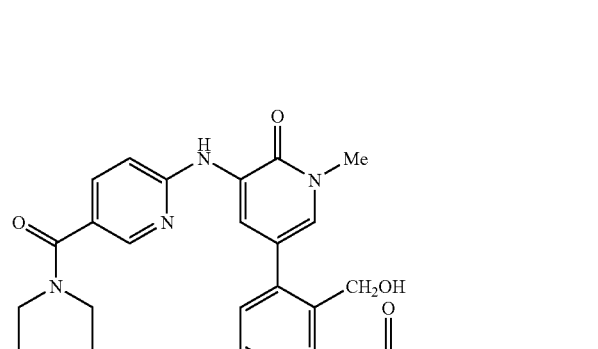 | 622 | 623 | | 0.114 |

TABLE II-continued

| Cpd. # | Structure | mw | ms | mp | IC$_{50}$$^1$ (μM) |
|---|---|---|---|---|---|
| II-98 | 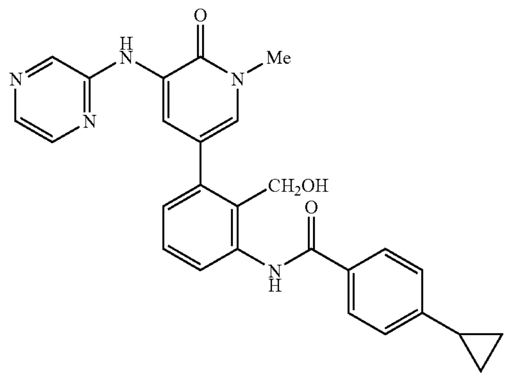 | 467 | 468 | | 0.09 |
| II-99 | 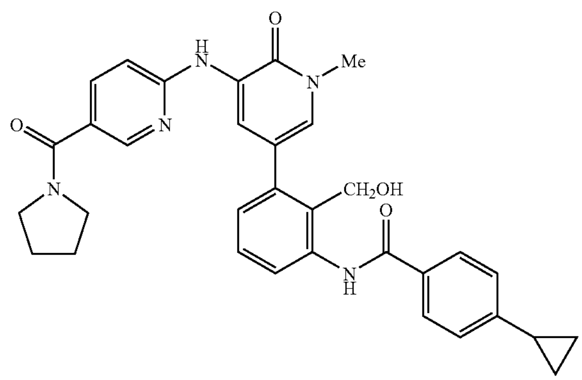 | 563 | 564 | | 0.011 |
| II-100 | 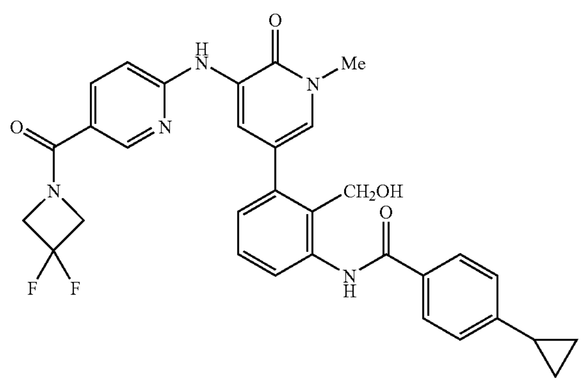 | 585 | 586 | | 0.031 |
| II-101 | 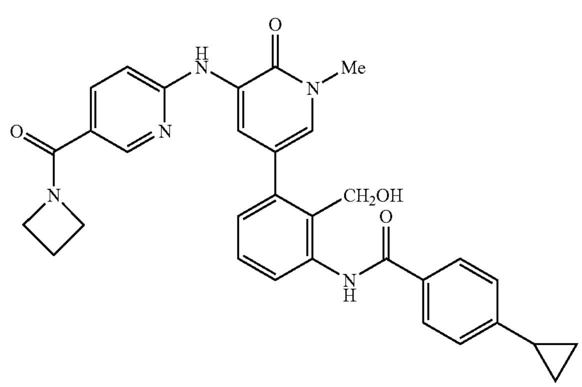 | 549 | 550 | | <0.01 |

TABLE II-continued

| Cpd. # | Structure | mw | ms | mp | IC$_{50}$[1] (µM) |
|---|---|---|---|---|---|
| II-102 | 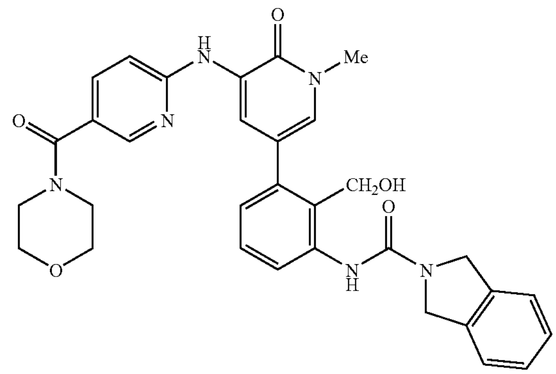 | 580 | 581 | | <0.01 |
| II-103 | 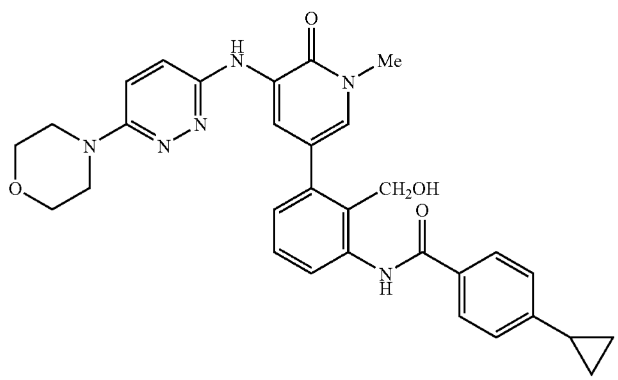 | 552 | 553 | | 0.014 |
| II-104 | 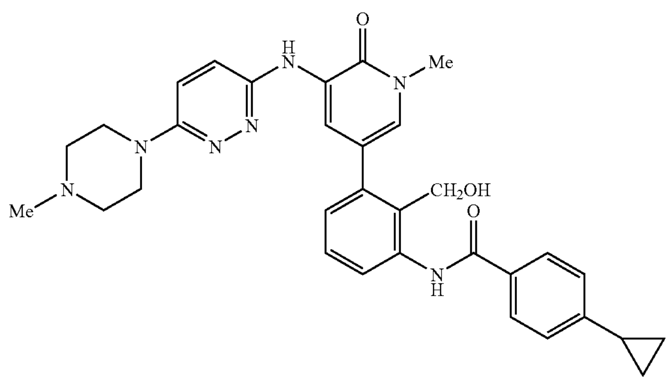 | 565 | 566 | | |

1. Bruton's tyrosine kinase Assay (Example 34)

Compounds of the present invention that are 2-amino(hetero)aryl-4-aryl-pyridazinone (TABLE I) derivatives are prepared utilizing a two step sequence starting from a 4,6-dihalo-2-alkyl-2H-pyridazin-3-one, e.g., A-1b. Displacement of the 2-halo moiety with a heterocyclic amine results in the introduction of the (hetero)aryl amine into the 6-position. The heterocyclic amine is optionally substituted with other groups within the scope of the invention or with a moiety which can be converted into desired substituents. Thus in SCHEME A the pyrimidine is 2-methylsulfanyl-pyrimidin-4-ylamine (A-5) The methylsulfanyl moiety can be oxidized to the corresponding sulfone which is easily displaced by nucleophiles in a subsequent step. The 4-substitued phenyl moiety is introduced by a Suzuki type coupling of a 4-halo-pyridazinone and a boronic acid derivative such as 4-(1,1-dimethylethyl)-N-[2-methyl-3-(4,4,5,5-tetramethyl-1,3,2-dioxaborolan-2-yl)phenyl]-benzamide (A-6, CASRN 910235-65-3) which affords A-3a. One skilled the art will appreciate that a wide variety of boronic acids are available including 4,4,5,5-tetramethyl-2-(3-nitro-phenyl)-[1,3,2]dioxaborolane (CASRN 68716-48-3) or 4,4,5,5-tetramethyl-2-(2-methyl-3-nitro-phenyl)-[1,3,2]dioxaborolane (C-1, CASRN 910235-64-2) which can undergo reduction of the nitro group and functionalization of the resulting amine to produce amides, ureas and sulfonamides. Other useful boronic acid derivatives which are described in the examples which follow. Elaboration of the phenyl substituents can occur either prior to or after the Suzuki coupling. Thus, for example, the Suzuki condensation can be carried out with 2-methyl-3-(4,4,5,5-tetramethyl-[1,3,2]dioxaborolan-2-yl)-phenylamine (14a, CASRN 882678-96-8) or 3-(4,4,5,5-tetramethyl-[1,3,2]dioxaborolan-2-yl)-phenylamine (14b) which can be acylated after the palladium-catalyzed coupling step (example 5). Coupling of [3-(4,4,5,5-tetramethyl-[1,3,2]dioxaborolan-2-yl)-phenyl]-acetic acid (CASRN 797755-05-6 allows introduction of the amine moiety afer the Suzuki condensation (example 8). Compounds of the present invention with a 3H-quinazolin-4-one moiety (e.g., I-8) were prepared from 38 which is prepared by sequential condensation of 4-tert-butyl-anthanilic acid with trimethylorthoformate and 14a to afford 38 which is utilized in the Suzuki coupling. Compounds with a 2,3-dihydro-1H-quinazolin-4-one moiety (e.g., I-34) are prepared by reduction of the corresponding 3H-quinazolin-4-one.

SCHEME A

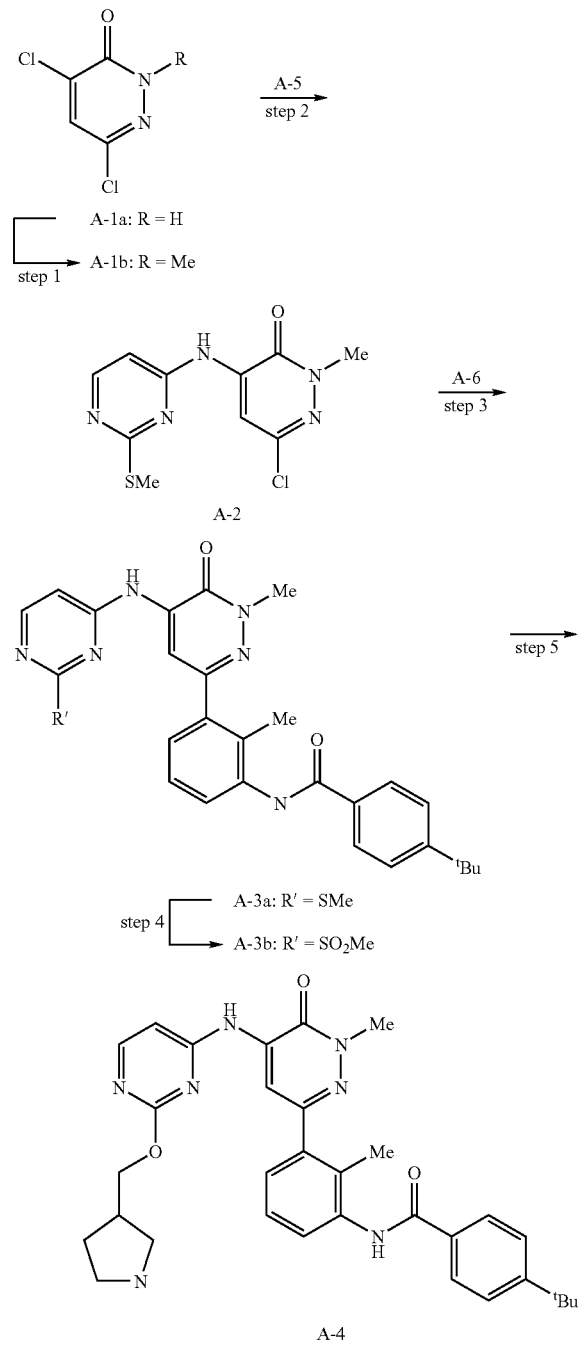

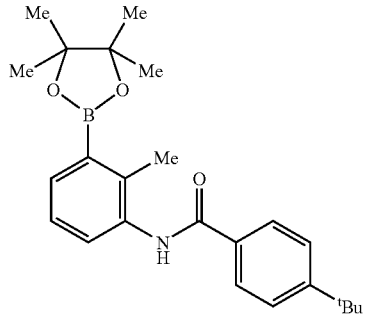

The Suzuki reaction (N. Miyama and A. Suzuki, *Chem Rev.* 1995 95:2457-2483; A. Suzuki, *J. Organomet. Chem.* 1999 576:147-168) is a palladium-catalyzed coupling of a boronic acid with an aryl or vinyl halide or triflate. The reaction is postulated to proceed by an oxidative-addition mechanism. Pd(II) compounds used as catalysts are believed to be reduced to the catalytically active Pd(0) species in situ. Typical catalysts bis-(tri-o-tolylphosphine) -palladium(II)chloride, (dba)$_3$ Pd$_2$(0)/tris-o-tolylphosphine, (dba)$_3$Pd$_2$(0)/tris-(2-furyl)phosphine, (dba)$_3$Pd$_2$(0)/2,2'-bis-(diphenylphosphino)-1,1'-binaphthyl, Pd(0)(PPh$_3$)$_4$, Pd(0)Cl$_2$(dppf) or Pd(II)(OAc)$_2$/1,3-bis-(triphenylphosphino)-propane. The reaction is often carried out in the presence of a base such as sodium-tert-butoxide, bis-(trimethylsilyl)-lithium amide, K2CO3, Cs$_2$CO$_3$ or TEA. The reaction can be carried out in a variety of organic solvents including toluene, THF, dioxane, DCE, DMF, DMSO and MeCN, aqueous solvents and under biphasic conditions. Reactions are typically run from about RT to about 150° C. Additives such as CsF, KF, TIOH, NaOEt and KOH frequently accelerate the coupling. Although there are numerous components in the Suzuki reaction including the palladium source, the ligand, additive solvent, temperature, etc., numerous protocols have been identified. Recently useful general conditions have been disclosed. A. F. Littke et al. *J. Am. Chem. Soc.* 2000 122:4020-4028 disclose conditions for Suzuki cross-coupling with arylboronic acids in high yield at RT utilizing Pd2(dba)$_3$/P(tert-bu)$_3$ and conditions for cross-coupling of aryl- and vinyl triflates utilizing Pd(OAc)$_2$/P(C$_6$H$_{11}$)$_3$ at RT. (J. P. Wolf et al. *J. Am. Chem. Soc.* 1999 121:9550-9561) disclose efficient condition for Suzuki cross-coupling utilizing Pd(OAc)$_2$/ o-(di-tert-butylphosphino)biphenyl or o-(dicyclohexylyphosphino)biphenyl. One skilled in the art will be able to identify a satisfactory protocol without undue experimentation.

Oxidation of a thiol to a sulfone is typically facile. Sulfur oxidations are commonly carried out with aqueous solution of hydrogen peroxide, NaIO$_4$, tert-butylhypochlorite, acyl nitrites, sodium perborate potassium hydrogen persulfate and peracids such as peracetic acid and meta-chloroperbenzoic acid. Exposure to two or more equivalents of oxidant results in oxidation to the sulfone. Displacement of the sulfone with oxygen and nitrogen nucleophiles yielded compounds as described in examples 1 and 2.

SCHEME B

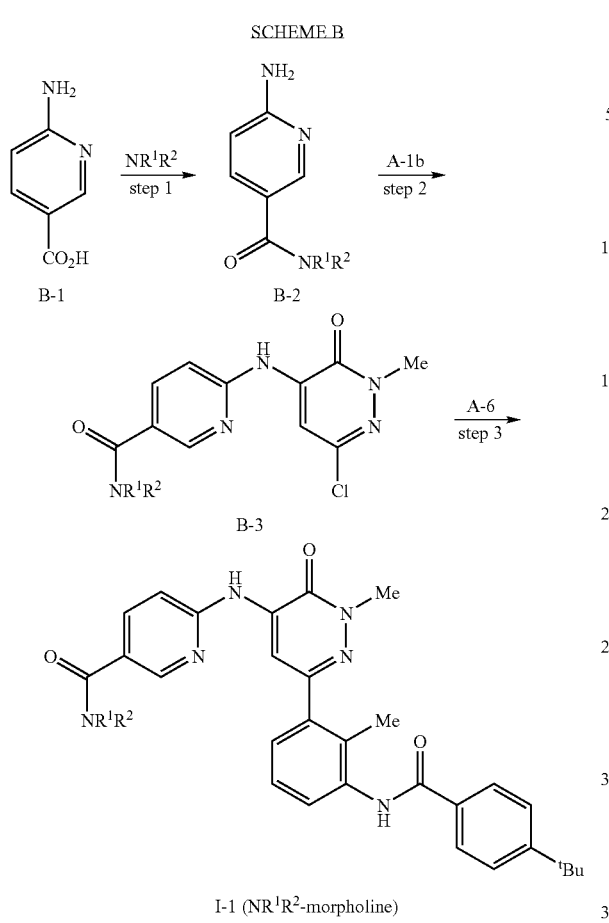

Compounds of the present invention which the pyridazinone is substituted with a 6-amino-nicotinamide moiety are prepared by contacting A-1 with a 6-amino-nictinamide derivative in which the amide can be a primary, secondary or tertiary amide which can be prepared by condensation of 6-amino-nicotinic acid with a suitable amine. (SCHEME B)

The amides are prepared by forming an activated carboxylic acid, such as an acid chloride or a symmetrical or mixed acid anhydride, and reacting the activated derivative with the appropriate amine in a solvent such as DMF, DCM, THF, with or without water as a co-solvent at temperatures between 0° and 60° C. generally in the presence of a base such as $Na_2CO_3$, $NaHCO_3$, $K_2CO_3$, DIPEA, TEA or pyridine and the like to afford an amide. Carboxylic acids are converted into their acid chlorides using standard reagents well known to someone skilled in the art, such as thionyl chloride, oxalyl chloride, phosphoryl chloride and the like. Those reagents can be used in presence of bases such as DIPEA, TEA or pyridine in inert solvent such as DCM or DMF.

Alternatively a carboxylic acid can be converted in situ into activated acids by different coupling procedures known to those skilled in the art. These activated acids were reacted directly with the amines to afford amides. Said activation with those peptide coupling procedures can involve the use of an activating agent like EDCI, DCC, HOBt, BOP, PyBrOP, HATU or Mukaiyama's reagent (2-fluoro-1-methylpyridinium p-toluenesulphonate) and the like with or without a base such NMM, TEA or DIPEA in an inert solvent such as DMF or DCM at temperatures between 0° and 60° C. The reaction may alternatively be carried out in presence of HATU or 1-hydroxy-7-azabenzotriazole (HOAt) and TEA or DIPEA in DMF, DCM or THF. Acylation of amines (J. March, supra pp.417-425; H. G. Benz, *Synthesis of Amides and Related Compounds in Comprehensive Organic Synthesis*, E. Winterfeldt, ed., vol. 6, Pergamon Press, Oxford 1991 pp. 381411) has been reviewed.

The boronic acid derivatives utilized in the coupling step also contain amide linkages (see e.g., SCHEME D) and these can be introduced by utilizing similar methodology. One skilled in the art will appreciate that the choice of coupling reagent is a matter of convenience.

SCHEME C

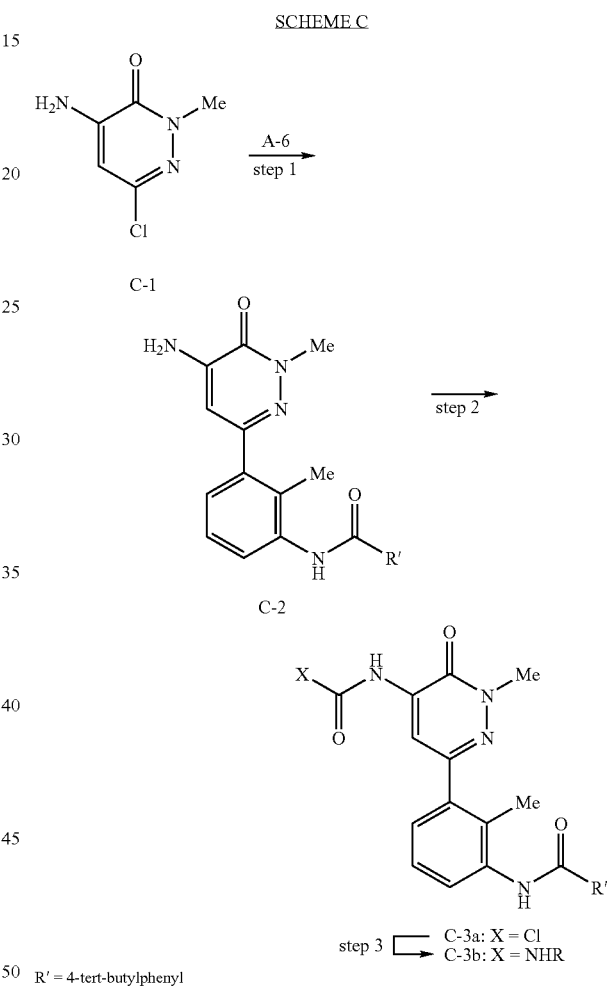

R' = 4-tert-butylphenyl
R = $C_{1-6}$ alkyl

Compounds of the present invention substituted at the 3-position by an N-alkyl-ureido moiety are accessible from 4-amino-6-chloro-2-methyl-2H-pyridazin-3-one (CASRN 3366-87-8). Suzuki coupling of A-6, or alternate dioxaborolanes, and C-1 affords C-2 which is converted to a urea C-3 by sequential treatment with phosgene and an amine or by direct condensation with an isocyanate. Alternatively the amino group of 42b can be converted to a urea prior to the Suzuki coupling step.

Compounds according to formula I wherein X is CH (TABLE II) are prepared analogously from 1-alkyl-3-amino-5-bromo-1H-pyridin-2-one (CASRN 910543-72-5) wherein $R^1$—NH— is a urea or from 1-alkyl-3,5-dibromo-1H-pyridin-2-one wherein $R^1$—NH— is a (hetero)aryl-amine.

Compounds of the present invention with a hydroxy methyl substitutent were prepared

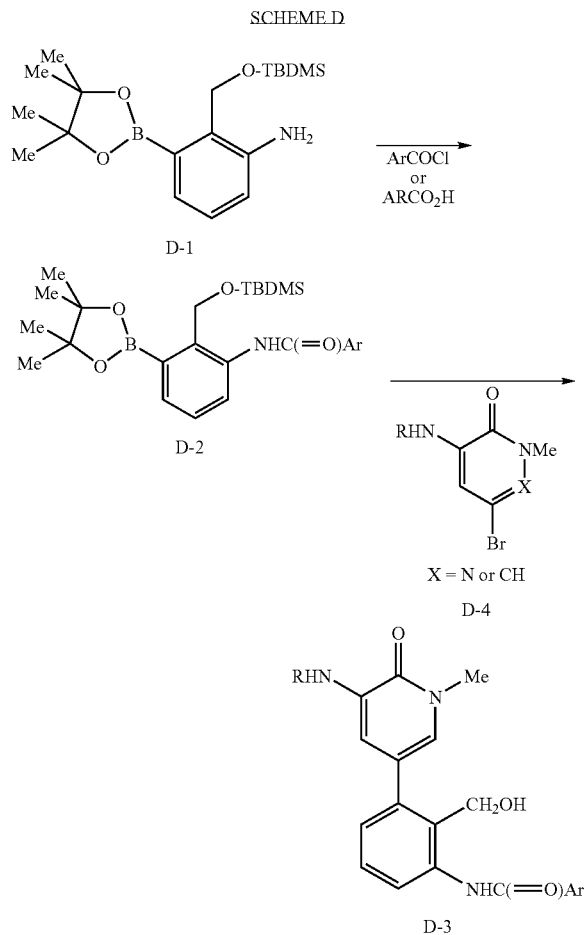

R = optionally substituted heteroaryl, phenyl, alkylcarbamoyl or heteroalkylcarbamoyl
Ar = optionally substituted aryl or heteroaryl by condensation a boronic acid derivative substituted by a tert-butyl-dimethyl-silanyloxymethyl) moiety and a appropriately substituted pyridone or pyridazinone D-4. While the present examples utilize the TBDMS protecting group on skilled in the art will appreciate that other alcohol protecting groups could be substituted for the TBDMS group. Suzuki-coupling of 2 -(tert-butyl-dimethyl-silanyloxymethyl)-3-(4,4,5,5-tetramethyl-[1,3,2]dioxaborolan-2-yl)-phenylamine or 2-[2-(tert-butyl-dimethyl-silanyloxymethyl)-3-nitro-phenyl]-4,4,5,5-tetramethyl-[1,3,2]dioxaborolane permit incorporation of the amide side chain at a later stage in the synthesis.

Pharmacological Activity

The pyrimidine and pyridine derivatives described herein are kinase inhibitors, in particular Btk inhibitors. These inhibitors can be useful for treating one or more diseases responsive to kinase inhibition, including diseases responsive to Btk inhibition and/or inhibition of B-cell proliferation, in mammals. Without wishing to be bound to any particular theory, it is believed that the interaction of the compounds of the invention with Btk results in the inhibition of Btk activity and thus in the pharmaceutical utility of these compounds.

Accordingly, the invention includes a method of treating a mammal, for instance a human, having a disease responsive to inhibition of Btk activity, and/or inhibiting B-cell proliferation, comprising administrating to the mammal having such a disease, an effective amount of at least one chemical entity provided herein. An effective concentration may be ascertained experimentally, for example by assaying blood concentration of the compound, or theoretically, by calculating bioavailability. Other kinases that may be affected in addition to Btk include, but are not limited to, other tyrosine kinases and serine/threonine kinases. Example 24 describes a enzyme inhibition assay to measure inhibition of Btk activity by compounds of the present invention. Example 25 describes a functional assay to measure inhibition of Ca2+ influx mediated by Btk kinase.

Kinases play notable roles in signaling pathways controlling fundamental cellular processes such as proliferation, differentiation, and death (apoptosis). Abnormal kinase activity has been implicated in a wide range of diseases, including multiple cancers, autoimmune and/or inflammatory diseases, and acute inflammatory reactions. The multifaceted role of kinases in key cell signaling pathways provides a significant opportunity to identify novel drugs targeting kinases and signaling pathways.

An embodiment includes a method of treating a patient having an autoimmune and/or inflammatory disease, or an acute inflammatory reaction responsive to inhibition of Btk activity and/or B-cell proliferation.

Autoimmune and/or inflammatory diseases that can be affected using compounds and compositions according to the invention include, but are not limited to: psoriasis, allergy, Crohn's disease, irritable bowel syndrome, Sjogren's disease, tissue graft rejection, and hyperacute rejection of transplanted organs, asthma, systemic lupus erythematosus (and associated glomerulonephritis), dermatomyositis, multiple sclerosis, scleroderma, vasculitis (ANCA-associated and other vasculitides), autoimmune hemolytic and thrombocytopenic states, Goodpasture's syndrome (and associated glomerulonephritis and pulmonary hemorrhage), atherosclerosis, rheumatoid arthritis, chronic Idiopathic thrombocytopenic purpura (ITP), Addison's disease, Parkinson's disease, Alzheimer's disease, diabetes, septic shock, and myasthenia gravis, Included herein are methods of treatment in which at least one chemical entity provided herein is administered in combination with an anti-inflammatory agent. Anti-inflammatory agents include but are not limited to NSAIDs, non-specific and COX-2 specific cyclooxgenase enzyme inhibitors, gold compounds, corticosteroids, methotrexate, tumor necrosis factor receptor (TNF) receptor antagonists and immunosuppressants.

Examples of NSAIDs include, but are not limited to, ibuprofen, flurbiprofen, naproxen and naproxen sodium, diclofenac, combinations of diclofenac sodium and misoprostol, sulindac, oxaprozin, diflunisal, piroxicam, indomethacin, etodolac, fenoprofen calcium, ketoprofen, sodium nabumetone, sulfasalazine, tolmetin sodium, and hydroxychloroquine. Examples of NSAIDs also include COX-2 specific inhibitors such as celecoxib, valdecoxib, lumiracoxib and/or etoricoxib.

In some embodiments, the anti-inflammatory agent is a salicylate. Salicylates include by are not limited to acetylsalicylic acid or aspirin, sodium salicylate, and choline and magnesium salicylates.

The anti-inflammatory agent may also be a corticosteroid. For example, the corticosteroid may be cortisone, dexamethasone, methylprednisolone, prednisolone, prednisolone sodium phosphate, or prednisone.

In additional embodiments the anti-inflammatory agent is a gold compound such as gold sodium thiomalate or auranofin.

The invention also includes embodiments in which the anti-inflammatory agent is a metabolic inhibitor such as a dihydrofolate reductase inhibitor, such as methotrexate or a dihydroorotate dehydrogenase inhibitor, such as leflunomide.

Other embodiments of the invention pertain to combinations in which at least one anti-inflammatory compound is an anti-C5 monoclonal antibody (such as eculizumab or pexelizumab), a TNF antagonist, such as entanercept, or infliximab, which is an anti-TNF alpha monoclonal antibody.

Still other embodiments of the invention pertain to combinations in which at least one active agent is an immunosuppressant compound such as an immunosuppressant compound chosen from methotrexate, leflunomide, cyclosporine, tacrolimus, azathioprine, and mycophenolate mofetil.

B-cells and B-cell precursors expressing BTK have been implicated in the pathology of B-cell malignancies, including, but not limited to, B-cell lymphoma, lymphoma (including Hodgkin's and non-Hodgkin's lymphoma), hairy cell lymphoma, multiple myeloma, chronic and acute myelogenous leukemia and chronic and acute lymphocytic leukemia.

BTK has been shown to be an inhibitor of the Fas/APO-1 (CD-95) death inducing signaling complex (DISC) in B-lineage lymphoid cells. The fate of leukemia/lymphoma cells may reside in the balance between the opposing proapoptotic effects of caspases activated by DISC and an upstream anti-apoptotic regulatory mechanism involving BTK and/or its substrates (Vassilev et al., *J. Biol. Chem.* 1998, 274, 1646-1656).

It has also been discovered that BTK inhibitors are useful as chemosensitizing agents, and, thus, are useful in combination with other chemotherapeutic drugs, in particular, drugs that induce apoptosis. Examples of other chemotherapeutic drugs that can be used in combination with chemosensitizing BTK inhibitors include topoisomerase I inhibitors (camptothecin or topotecan), topoisomerase II inhibitors (e.g. daunomycin and etoposide), alkylating agents (e.g. cyclophosphamide, melphalan and BCNU), tubulin directed agents (e.g. taxol and vinblastine), and biological agents (e.g. antibodies such as anti CD20 antibody, IDEC 8, immunotoxins, and cytokines).

Btk activity has also be associated with some leukemias expressing the bcr-abl fusion gene resulting from translocation of parts of chromosome 9 and 22. This abnormality is commonly observed in chronic myelogenous leukemia. Btk is constitutively phosphorylated by the bcr-abl kinase which initiates downstream survival signals which circumvents apoptosis in bcr-abl cells. (N. Feldhahn et al. *J. Exp. Med.* 2005 201(11):1837-1852)

Dosage and Administration

The compounds of the present invention may be formulated in a wide variety of oral administration dosage forms and carriers. Oral administration can be in the form of tablets, coated tablets, dragées, hard and soft gelatine capsules, solutions, emulsions, syrups, or suspensions. Compounds of the present invention are efficacious when administered by other routes of administration including continuous (intravenous drip) topical parenteral, intramuscular, intravenous, subcutaneous, transdermal (which may include a penetration enhancement agent), buccal, nasal, inhalation and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semi-solids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

The term "excipient" as used herein refers to a compound that is useful in preparing a pharmaceutical composition, generally safe, non-toxic and neither biologically nor otherwise undesirable, and includes excipients that are acceptable for veterinary use as well as human pharmaceutical use. The compounds of this invention can be administered alone but will generally be administered in admixture with one or more suitable pharmaceutical excipients, diluents or carriers selected with regard to the intended route of administration and standard pharmaceutical practice.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

A "pharmaceutically acceptable salt" form of an active ingredient may also initially confer a desirable pharmacokinetic property on the active ingredient which were absent in the non-salt form, and may even positively affect the pharmacodynamics of the active ingredient with respect to its therapeutic activity in the body. The phrase "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4 -toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polyactic acid.

Suitable formulations along with pharmaceutical carriers, diluents and expcipients are described in *Remington: The Science and Practice of Pharmacy* 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 1000 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The following examples illustrate the preparation and biological evaluation of compounds within the scope of the invention. These examples and preparations which follow are provided to enable those skilled in the art to more clearly understand and to practice the present invention. They should not be considered as limiting the scope of the invention, but merely as being illustrative and representative thereof.

EXAMPLE 1

4-tert-Butyl-N-(2-methyl-3-{1-methyl-6-oxo-5-[2-(pyrrolidin-3-ylmethoxy)-pyrimidin-4-ylamino]-1,6-dihydro-pyridazin-3-yl}-phenyl)-benzamide (I-19, SCHEME A)

step 1—A solution of 4,6-dichloro-2H-pyridazin-one (A-1a, 3.9 g, 23 mmol, CASRN 17285-37-9) in anhydrous DMF (45 mL) was cooled at 0° C. under nitrogen. To this solution was added sodium hydride (0.92 g, 23 mmol, 60% dispersion in mineral oil). The mixture was warmed to RT and stirred for 30 min. then cooled to about 10° C. and methyl iodide (3.2 g, 23 mmol) was added drop wise over 5 min. The resulting mixture was stirred at RT for about 4 h and then diluted with water (50 mL) and extracted with EtOAc (100 mL). The organic layer was washed three times with brine, dried ($Na_2SO_4$) and concentrated in vacuo to give 4 g (100%) of A-1b which used in the next step without further purification.

step 2—To a solution of 2-methylsulfanyl-pyrimidin-4-ylamine (A-5, 1.4 g, 9.8 mmol, CASRN 2183-66-6) and anhydrous DMF (14 mL) cooled at 0° C. and under nitrogen atmosphere was added NaH (0.392 g, 609.8 mmol, 60% mineral oil dispersion). The reaction mixture was warmed to RT and stirred for 30 min. To the resulting reaction mixture was added dropwise over 5 min a solution of A-1b (0.872 g, 4.9 mmol) in DMF (5 mL). The reaction mixture was stirred at RT for 2 h and then diluted with water (20 mL) and EtOAc (50 mL). The organic layer was washed three times with brine. The desired product which precipitated out of an EtOAc solution, was filtered and dried under high vacuum to afford 1 g (71.4%) of A-2 which was used in the next step without further purification.

step 3—To a suspension of A-2 (0.2 g, 0.7 mmol) and DME (8 mL) in a microwave tube was added a solution of $Na_2CO_3$ (0.223 g, 2.1 mmol) in water (3 mL) and A-6 (0.277 g, 0.70 mmol). The mixture was sparged with nitrogen, $Pd(0)(PPh_3)_4$ (0.041 g, 0.035 mmol) was added and the tube sealed and heated at 175° C. in a microwave apparatus for 45 min. After cooling, the combined reaction mixture was partitioned between EtOAc and $H_2O$. The organic layer was washed with brine, dried ($Na_2SO_4$), filtered and concentrated in vacuo. The crude residue was purified by $SiO_2$ chromatography eluting with a MeOH/DCM gradient (2% to 4% MeOH) to afford 0.4 g (55%) of I-12.

step 4—To a solution of I-12 (0.370 g, 0.719 mmol), MeOH (16 mL) and THF (10 mL) was added dropwise over 5 min a solution of oxone (0.884 g, 1.43 mmol) in $H_2O$ (6 mL). The solution was stirred at RT for 4 h then a second portion of oxone (0.6 g, 0.97 mmol) in $H_2O$ (4 mL) was added and the mixture stirred for additional 2 h. The reaction mixture was diluted with $H_2O$ (50 mL) and extracted with EtOAc (100 mL). The organic layer was washed with brine, dried ($Na_2SO_4$), filtered, concentrated and dried in vacuo to afford 0.380 g (96%) of I-13 which was used in the next step without further purification.

step 5—To a solution of I-13 (0.100 g, 0.18 mmol) and DMF (2 mL) was added NaH (0.028 g, 60%, 0.72 mmol) and the resulting solution warmed to RT and stirred 30 min. To the resulting solution was added pyrrolidin-3-yl-methanol (0.054 g, 0.535 mmol) and the mixture stirred at RT for 4 h. The reaction mixture was next diluted with water and extracted with EtOAc. The organic layer was washed with brine, dried (Na₂SO₄) and concentrated in vacuo. The resulting residue was purified on a preparative SiO₂ TLC plate developed with 10% MeOH/DCM to afford 0.025 g (26%) of I-19.

I-17 and I-18 were prepared analogously except pyrrolidin-3-ol was replaced with methanol and N,N-dimethylamino-ethanol, respectively.

I-45 can be prepared analogously except in step 2,2-methylsulfanyl-pyrimidin-4-ylamine is replaced with 3-amino-1-methyl-pyrazole, in step 3, A-6 is replaced with 120 (Ar=4-cyclopropylphenyl) and steps 3 and 4 are omitted.

EXAMPLE 2

4-tert-Butyl-N-(3-{5-[2-(3-hydroxy-pyrrolidin-1-yl) - pyrimidin-4-ylamino]-1-methyl-6-oxo-1-6 -dihydro-pyridazin-3-yl}-2-methyl-phenyl)-benzamide (I-22)

To a solution of I-13 (0.069 g, 0.12 mmol) and DMF (2 mL) was added pyrrolidin-3-ol (0.032 g, 0.36 mmol). The reaction mixture was stirred for 2 h at RT and then for 2 h at 60° C. The reaction mixture was cooled to RT and partitioned between EtOAc and H₂O. The organic layer was washed with brine, dried (Na₂SO₄), filtered and concentrated in vacuo. The recovered residue was purified on a preparative SiO₂ TLC plate developed with 5% MeOH/DCM to afford 0.028 g (42%) of I-22.

The following analogs were prepared analogously except pyrrolidin-3-ol was replaced with the amine or alcohol in parenthesis: I-11 (N-methyl piperazine), I-14 (morpholine), I-20 (pyrrolidin-3yl-methanol) and I-21 (pyrrolidine).

EXAMPLE 3

4-tert-Butyl-N-(2-methyl-3-{1-methyl-5-[5-(morpholine-4-carbonyl)-pyridin-2-ylamino]-1,6-oxo-dihydro-pyridazin-3-yl}-phenyl)-benzamide (I-1; SCHEME B)

step 1—To a solution of morpholine (9.00 g, 103 mmol) in EtOH (400 mL) was added EDCI (10.0 g, 52.2 mmol), HOBt (7.00 g 51.8 mmol), and 6-aminonicotinic acid (6.00 g, 43.4 mmol). After stirring for 18 h, the resulting solid was filtered. The solid was triturated with a mixture of MeOH (100 mL) and DCM (100 mL) to afford 3.08 g of B-2 (NR¹R² together are morpholine): MS (ESI) 208.1 (M+H).

step 2—To an ice cold suspension of B-2 (2.921 g, 14.11 mmol, CASRN 827587-90-6) and DMF (50 mL) was added NaH (847 mg, 21.2 mmol, 60% suspension in mineral oil). The mixture was stirred at RT for 30 min then re-cooled to 0° C. and A-1b (1.256 g, 7.056 mmol) was added. After 2 h, the reaction mixture was partitioned between saturated aqueous NH₄Cl and EtOAc. The EtOAc layer was dried (MgSO₄), filtered and concentrated in vacuo. The crude product was purified by SiO₂ chromatography eluting with 2% MeOH/DCM to afford 0.732 g (2.09 mmol) of B-3: MS (ESI) 350.1 (M+H)⁺.

step 3—To a suspension of B-3 (0.030 g, 0.085 mmol) and A-6 (0.035 g, 0.089 mmol and DME (2 mL) in a microwave tube was added a solution of Na₂CO₃ (0.028 g, 0.27 mmol) and H₂O (0.5 mL). After sparging the mixture with nitrogen, Pd(0)(PPh₃)₄ (0.01 g, 0.009 mmol) was added and the tube sealed and heated at 175° C. for 30 min in a microwave apparatus. The reaction mixture was partitioned between H₂O and EtOAc. The organic layer was washed with brine, dried (Na₂SO₄) and concentrated in vacuo. The crude product was purified on a preparative SiO₂ TLC plate developed with 5% MeOH/DCM to afford 0.034 g (69%) of I-1.

I-2 was prepared analogously except in step 1, morpholine was replaced with 1-methyl-piperazine which afforded (6-amino-pyridin-3-yl)-(4-methyl-piperazin-1-yl)-methanone (CASRN 652138-83-5).

I-3, I-4, I-9, and I-24 were prepared analogously except in step 1 was omitted and 2-amino-pyridine, 4-aminopyrimidine, methyl 6-amino-nicotinate (CASRN 36052-24-1) and 4-(4-aminobenzoyl)-morpholine (CASRN 51207-86-4), respectively, were was used in place of B-2 in step 2.

I-25 was prepared analogously except in step 3, A-6 was replaced with 14b (CASRN 210907-84-9) which was subsequently acylated with 4-tert-butyl-benzoic acid after the Suzuki coupling step I-26 was prepared by condensation of methyl 6-aminonicotinate (CASRN 36052-24-1) in place of B-2 in step 2. The Suzuki coupling proceeded with concomitant hydrolysis of the methyl ester and the resulting carboxylic acid was converted to the amide by BOP-mediated coupling of the acid and 4-hydroxy-piperidine in the presence of TEA and DMF. Step 1 in the example was omitted.

I-46 is prepared analogously except A-6 is replaced by 120 (Ar=4-cyclopropyl-phenyl) as described in step 5 of example 25.

EXAMPLE 4

4-tert-Butyl-piperazine-1-carboxylic acid (2-methyl-3-{1-methyl-5-[5-(morpholine-4-carbonyl) -pyridin-2-ylamino]-6-oxo-1,6-dihydro-pyridazin-3-yl}-phenyl)-amide (I-6)

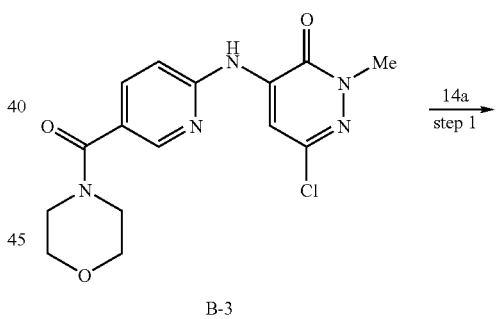

B-3

12a: R = Me
12b: R = H

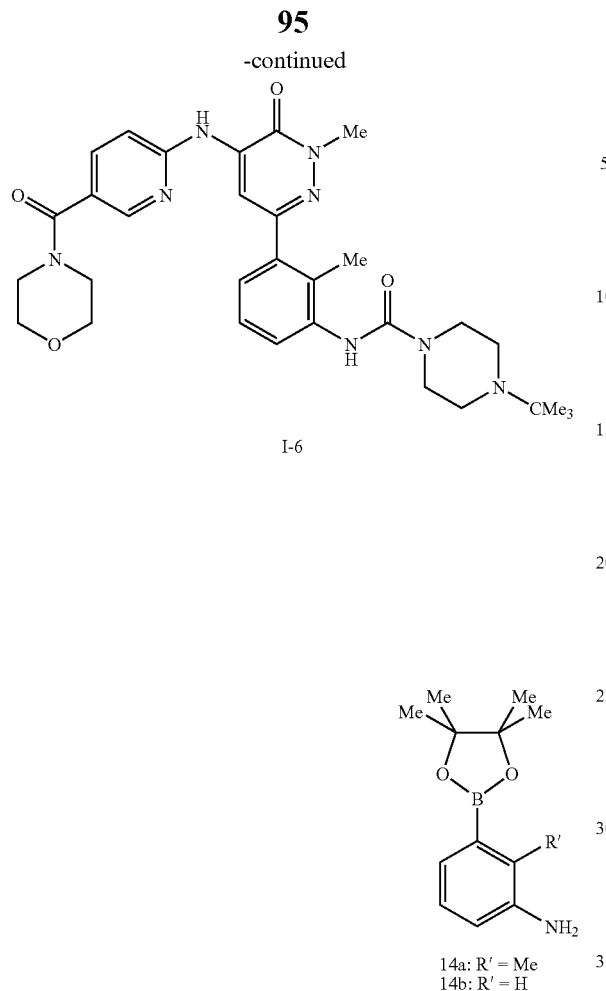

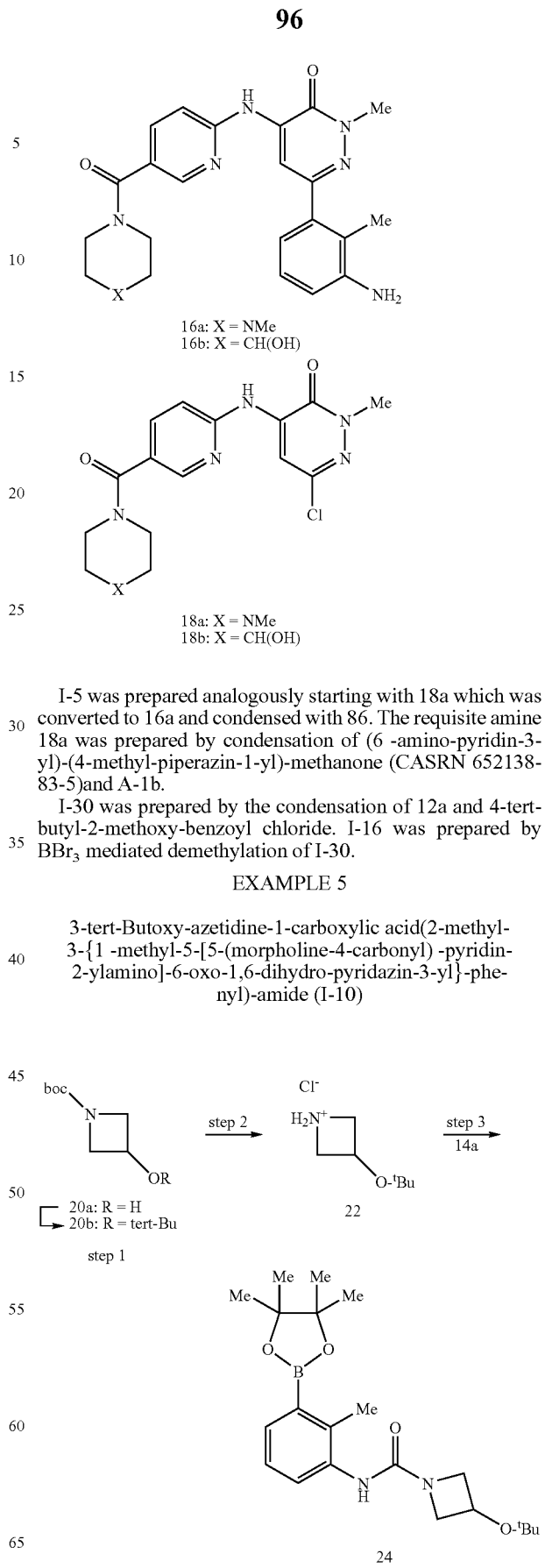

16a: X = NMe
16b: X = CH(OH)

18a: X = NMe
18b: X = CH(OH)

I-5 was prepared analogously starting with 18a which was converted to 16a and condensed with 86. The requisite amine 18a was prepared by condensation of (6-amino-pyridin-3-yl)-(4-methyl-piperazin-1-yl)-methanone (CASRN 652138-83-5) and A-1b.

I-30 was prepared by the condensation of 12a and 4-tert-butyl-2-methoxy-benzoyl chloride. I-16 was prepared by $BBr_3$ mediated demethylation of I-30.

EXAMPLE 5

3-tert-Butoxy-azetidine-1-carboxylic acid(2-methyl-3-{1-methyl-5-[5-(morpholine-4-carbonyl)-pyridin-2-ylamino]-6-oxo-1,6-dihydro-pyridazin-3-yl}-phenyl)-amide (I-10)

step 1—A solution of B-3 (149 mg, 0.426 mmol), 14a (105 mg, 0.426 mmol, CASRN 882678-96-8), Pd(0)(PPh$_3$)$_4$ (49 mg, 0.042 mmol), and Na$_2$CO$_3$ (135 mg, 1.28 mmol) in DME (2 mL) and H$_2$O (1 mL) was heated at 170° C. for 12.5 minutes in a microwave synthesizer. The resulting mixture was partitioned between EtOAc and water. The EtOAc layer was washed with brine, dried (MgSO$_4$), filtered and concentrated in vacuo. The crude product was purified by SiO$_2$ chromatography eluting with 4% MeOH/DCM to afford 0.154 g (0.366 mmol) of 12a: MS (ESI) 421 (M+H)$^+$.

step 2—To a suspension of 12a (50 mg, 0.12 mmol) in THF (4 mL) was added a phosgene solution (0.18 mL, 0.36 mmol, 1.93 M in toluene). After 20 min, 1-tert-butyl-piperazine (85 mg, 0.60 mmol) was added and the resulting solution stirred for 15 min. The resulting mixture was partitioned between EtOAc and dilute aqueous NaHCO$_3$. The EtOAc layer was washed with brine, dried (MgSO$_4$), filtered and concentrated in vacuo. The crude product was purified on a preparative SiO$_2$ TLC plate developed with 5% MeOH/DCM to afford 0.050 g (0.085 mmol) of I-6: MS (ESI) 589 (M+H)$^+$.

I-15 was prepared analogously except in step 2, 12a was condensed with 4-(1-hydroxy-1-methyl-ethyl)-benzoic acid (86) using BOP-mediated coupling as described in step 2 of example 6.

I-7 can be prepared analogously except in step 2, 12 is condensed with 4-tert-butyl-2-methoxy benzoic acid using BOP-mediated coupling as described in step 2 of example 6.

step 1—A solution of 20a (CASRN 141699-55-0, 1.313 g, 7.58 mmol), cyclohexane (20 mL), DCM (10 mL), tert-butyl trichloroacetimidate (5.4 mL, 30 mmol) and BF₃Et₂O (0.48 mL, 3.8 mmol) was stirred for 16 h. NaHCO₃ (2.5 g) was added, the mixture was filtered through CELITE®, and the filtrate was concentrated to 2.52 g of an oily white solid. The crude product was purified by SiO₂ chromatography eluting with an EtOAc/hexane gradient (0-50% EtOAc) to afford 0.408 g (23%) of 20b as a colorless oil.

step 2—A premixed solution of MeOH (2 mL) and acetyl chloride (0.5 mL) was added to a solution of 20b (0.251 g, 1.09 mmol) in MeOH (2 mL) at 0-5° C. The colorless solution was warmed to RT and stirred for 4 h, then concentrated, chasing with diethyl ether, to afford crude 22 as a white solid that was used without further purification.

step 3—Phosgene (20% in toluene, 0.459 mL, 0.874 mmol) was added to a solution of 14a (0.1697 g, 0.728 mmol) and DIPEA (0.510 mL, 2.93 mmol) in DCM (5 mL) cooled to 0-5° C. The reaction mixture was stirred for 10 min and then transferred via Pasteur pipette to a flask containing crude 22. A total of 5 mL of additional DCM was used in rinsing the flask. The yellow solution was stirred at 0-5° C. for 10 min, then 4 g of SiO₂ was added, and the mixture was concentrated to a pale yellow powder. The dry SiO₂ was applied to the top of a SiO₂ column and eluted with a EtOAc/hexane gradient (50-100% EtOAc) to afford 0.226 g (80%) of 24 as a white solid.

The synthesis of I-10 was completed by coupling of B-3 and 24 as previously described in step 3 of example 3.

EXAMPLE 6

N-(2-tert-Butoxy-ethyl)-2-(2-methyl-3-{1-methyl-5-[5-(morpholine-4-carbonyl)-pyridin-2-ylamino]-6-oxo-1,6-dihydro-pyridin-3-yl}-phenyl)-acetamide (I-32)

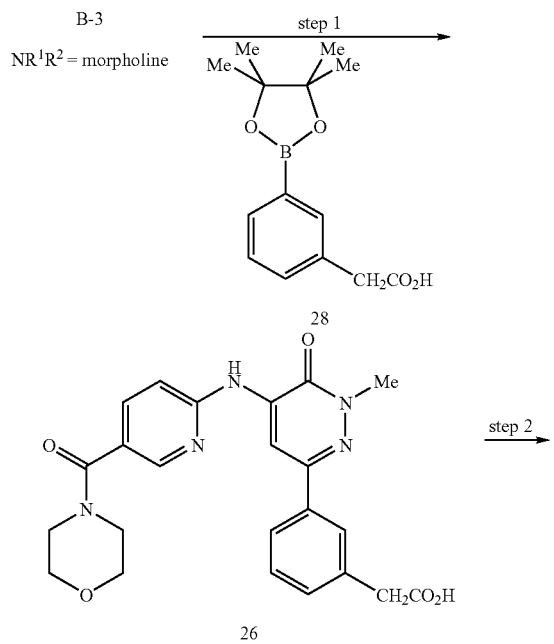

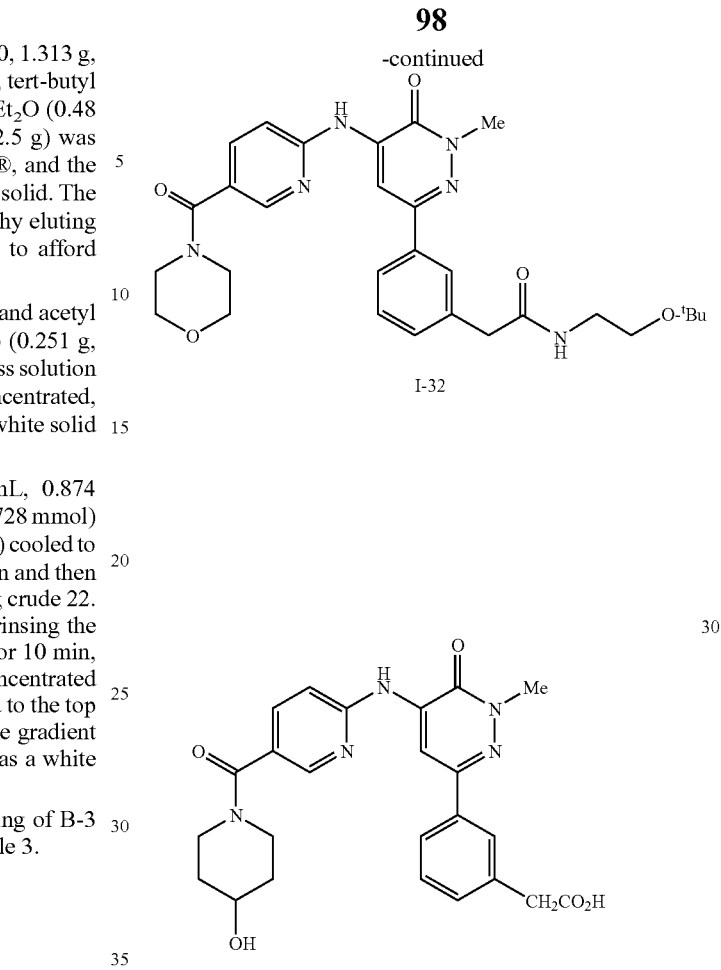

step 1—A solution of B-3 (256 mg, 0.732 mmol), 28 (192 mg, 0.732 mmol), Pd(0)(PPh₃)₄ (84 mg, 0.073 mmol), and Na₂CO₃ (310 mg, 2.93 mmol) in DME (2 mL) and H₂O (1 mL) was heated at 170° C. for 12.5 min in a microwave synthesizer. The resulting mixture was partitioned between EtOAc and H₂O. The pH of the aqueous layer was phase was adjusted to ca. pH 1 with 6M aqueous HCl and the resulting solid was filtered, washed with water and dried to afford 0.263 g (0.586 mmol) of 26: MS (ESI) 450.1 (M+H)⁺.

step 2—To 26 (50 mg, 0.11 mmol) and BOP (55 mg, 0.12 mmol) was added DMF (2 mL), N,N-dimethylaminoethanol (0.017 g, 0.11 mmol) and TEA (56 mg, 0.56 mmol). After 4 h the reaction mixture was partitioned between EtOAc and dilute aqueous NaHCO₃. The EtOAc layer was washed with brine, dried (MgSO₄), filtered and concentrated in vacuo. The crude product was purified on a preparative SiO₂ TLC plate developed with 5% MeOH/DCM to afford 0.033 g (0.060 mmol) of I-32: MS (ESI) 549 (M+H)⁺.

The following were prepared from 26: I-29, I-32 I-33 and I-36 were prepared by EDCI mediated coupling of 26, with 1-amino4,4-dimethyl-3-hydroxypentane, 2-tert-butoxy-ethylamine, 3-tert-butoxy-cyclobutylamine, pyrrolidine and 2-tert-butoxy-ethanol respectively using the EDCI coupling protocol described in step 2 of example 13 except excess DIPEA was added as the base. I-35 was prepared by BOP-catalyzed coupling of 28 and 3-iso-propoxy-cyclobutylamine using the protocol described in step 2 to afford 1-(3- tert-butoxy-azetidin-1-yl)-2-[3-(4,4,5,5-tetramethyl-[1,3,2]dioxaborolan-2-yl)-phenyl]-ethanone which was subjected to Suzuki-coupling with B-3 (NR$^1$R$^2$=morpholine).

I-31 was prepared analogously from 30 by EDCI mediated coupling with 2,3-dihydro-1H-isoindole to afford I-32. Suzuki coupling of 5-chloro-3-[5-(4-hydroxy-piperidine-1-carbonyl)-pyridin-2-ylamino]-1-methyl-1H-pyridin-2-one and 18 afforded 30.

EXAMPLE 7

6-{3-[2-(4-tert-Butyl-phenyl)-2-oxo-ethyl]-phenyl}-2-methyl-4-[5-(morpholine-4-carbonyl)-pyridin-2-ylamino]-2H-pyridazin-3-one (I-37)

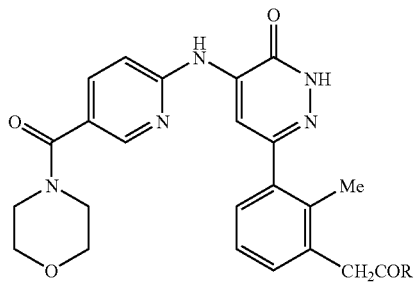

step 1 ⎡ 26: R = OH
       ⎣ 32: R = S-Ph step 2 ⎣ I-37: R = 4-tert-butyl-phenyl step 1—To 26 (163 mg, 0.362 mmol) and BOP (160 mg, 0.362 mmol) was added DMF (5 mL), TEA (125 mg, 1.23 mmol) and thiophenol (40 mg, 0.36 mmol). After stirring for 18 h, the resulting solution was partitioned between EtOAc and dilute aqueous NaHCO$_3$. The EtOAc layer was washed with brine, dried (MgSO$_4$), filtered and concentrated in vacuo. The crude product was purified by SiO$_2$ chromatography eluting with (2% MeOH/DCM) to afford 0.041 g (0.076 mmol) of 32: MS (ESI) 542.0 (M+H)$^+$.

step 2—To a solution of 32 (40 mg, 0.074 mmol), 4-tert-butylphenylboronic acid (16 mg, 0.089 mmol), copper(I) thiophenecarboxylate (17 mg, 0.089 mmol) and Pd$_2$(dba)$_3$ (1.6 mg, 0.0017 mmol) and THF (2 mL) was added a solution of triethylphosphite (1.2 mg, 0.072 mmol) and THF (2 mL). The resulting mixture was heated to 30° C. under an argon atmosphere for 18 h. The mixture was partitioned between EtOAc and H$_2$O. The EtOAc layer was washed with brine, dried (MgSO$_4$), filtered and concentrated in vacuo. The crude product was purified by preparative HPLC to afford 0.004 g (0.007 mmol) of I-37: MS (ESI) 566 (M+H)$^+$.

I-38 to I-44 can be prepared analogously except tha palladium coupling in step 2 is replaced by an amide coupling procedure of 26 with 1-methyl-piperazine, 3-tert-butoxy-azetidine, 2H-isoindole, 1-isopropyl-piperazine, 4-tert-butyl-piperidine, 3,3-dimethyl-butylamine, 1-acetyl-piperazine, respectively. The coupling can be carried out using BOP-mediated condensation as described in step 2 of example 6.

EXAMPLE 8

7-tert-Butyl-3-(2-methyl-3-{1-methyl-5-[5-(morpholine-4-carbonyl)-pyridin-2-ylamino]-6-oxo-1,6-dihydro-pyridazin-3-yl}-phenyl)-3H-quinazolin-4-one (I-8)

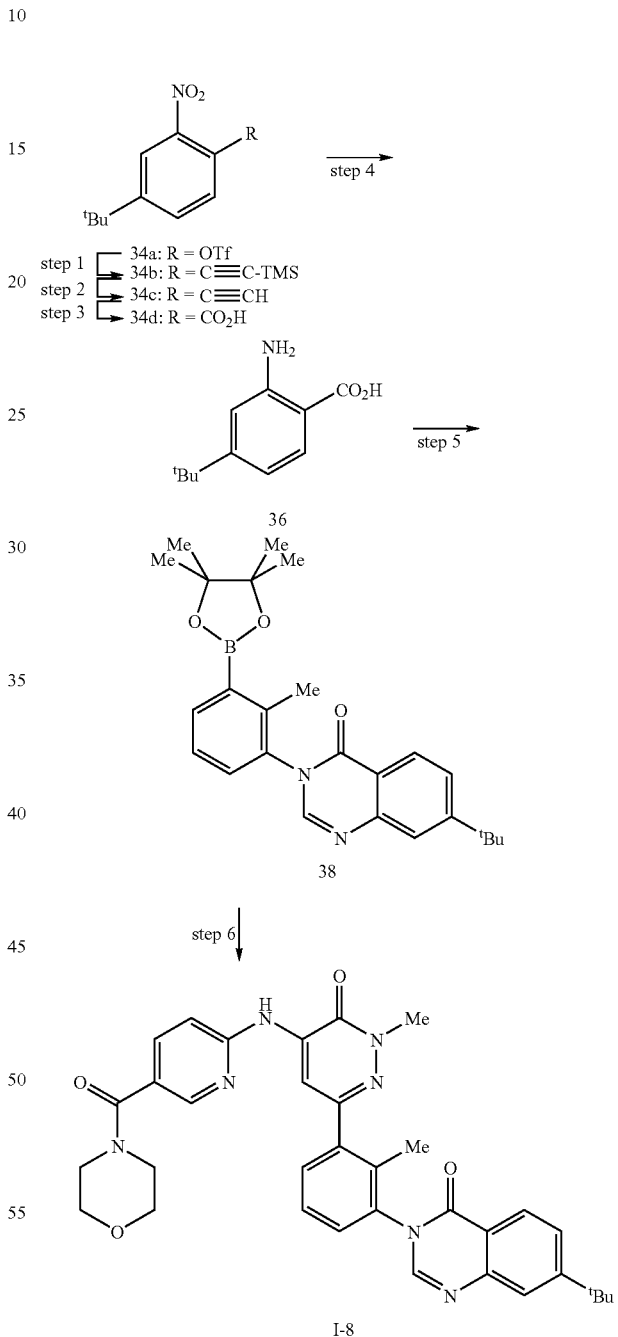

step 1—To 34a (3.715 g, 11.35 mmol), Cl$_2$(PPh$_3$)$_2$Pd(II) (336 mg, 0.478 mmol), CuI (168 mg, 0.882 mmol) was added DMF(45 ML), TEA (1.72 g, 17.0 mmol), and trimethylsilylacetylene (2.229 g, 22.70 mmol). The resulting mixture was heated at 90° C. under a nitrogen atmosphere for 15 min. The mixture was partitioned between EtOAc and H$_2$O. The EtOAc layer was washed with brine, dried (MgSO₄), filtered and concentrated in vacuo. The crude product was purified by SiO₂ chromatography eluting with DCM to yield 3.193 g (11.61 mmol) of 34b.

step 2—A solution of 34b (3.167 g, 11.51 mmol), K₂CO₃ (3.18 g, 23.0 mmol) were stirred in MeOH (75 mL) for 20 min. The resulting mixture was partitioned between EtOAc and water. The EtOAc layer was washed with brine, dried (MgSO₄), filtered and concentrated in vacuo. The crude product was purified by SiO₂ chromatography eluting with an EtOAc/hexane gradient (0 to 5% EtOAc/hexanes) to yield 1.910 g (9.398 mmol) of 34c.

step 3—To a solution of 34c (1.662 g, 8.176 mmol), CCl₄ (20 mL), MeCN (20 mL) and H₂O (40 mL) was added sequentially H₂IO₄ (9.322 g, 40.89 mmol) and Ru(III)Cl₃ (85 mg, 0.41 mmol). After stirring of 90 min, the resulting mixture was diluted with water and extracted with three portions of DCM. The combined DCM extracts were dried (MgSO₄), filtered and concentrated in vacuo to afford 1.924 g (19 mmol) of 34d.

step 4—A suspension of 34d (199 mg, 8.91 mmol), 10% Pd/C (40 mg) were stirred in EtOH (6 mL) under a hydrogen atmosphere 3 h. The resulting mixture was filtered and concentrated in vacuo to yield 0.177 g (0.916 mmol) of 36.

step 5—A solution of 36 (78 mg, 0.41 mmol) and trimethylorthoformate (2 mL) was heated to 105° C. for 30 min. The resulting solution was concentrated in vacuo. A solution of A-6 (100 mg, 0.41 mmol) in toluene (2 mL) was added. The resulting mixture was heated at reflux for 1 h, concentrated in vacuo, and purified by SiO₂ chromatography eluting with 15% EtOAc/hexanes to afford 0.068 g (0.16 mmol) of 38: MS (ESI) 419.2 (M+H)⁺.

step 6—A solution of B-3 (56 mg, 0.16 mmol, NR¹R² together are morpholine), 38 (68 mg, 0.16 mmol), Pd(0) (PPh₃)₄ (19 mg, 0.016 mmol), and Na₂CO₃ (52 mg, 0.49 mmol) in DME (2 mL) and H₂O (1 mL) was heated at 170° C. for 12.5 min in a microwave synthesizer. The resulting mixture was partitioned between EtOAc and H₂O. The EtOAc layer was washed with brine, dried (MgSO₄), filtered and concentrated in vacuo. The crude product was purified on a preparative SiO₂ TLC plate developed with 10% MeOH/DCM to afford 0.264 g (0.044 mmol) of I-8: MS (ESI) 606 (M+H)⁺.

EXAMPLE 9

7-tert-Butyl-3-(2-methyl-3-{1-methyl-5-[5-(morpholine-4-carbonyl)-pyridin-2-ylamino]-6-oxo-1,6-dihydro-pyridazin-3-yl}-phenyl)-2,3-dihydro-1H-quinazolin-4-one (I-34)

To a mixture of I-8 (11 mg, 0.018 mmol) and NaBCNH₃ (1.3 mg, 0.019 mmol) in 1 mL MeOH was added 1 drop of 2M HCl in MeOH to bring the pH to ca. 3. After stirring for 45 min, the resulting mixture was partitioned between EtOAc and dilute aqueous NaHCO₃. The EtOAc layer was washed with brine, dried (MgSO₄), filtered and concentrated in vacuo. The crude product was purified on a SiO₂ preparative TLC plate developed with 5% MeOH/DCM to afford 6.5 mg (0.011 mmol) of I-34: MS (ESI) 608 (M+H)⁺.

EXAMPLE 10

4-tert-Butyl-N-{2-methyl-3-[1-methyl-5-(3-methyl-ureido)-6-oxo-1,6-dihydro-pyridazin-3-yl]-phenyl}-benzamide (I-23)

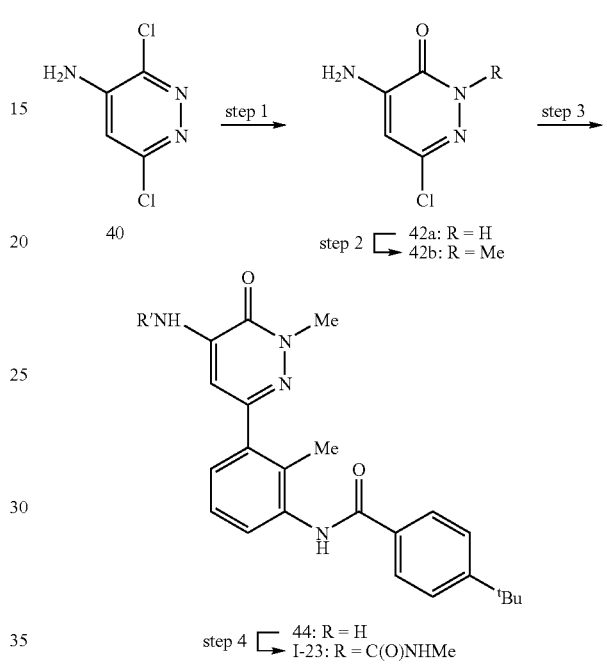

step 1—A mixture of 40 (0.127 g, 0.774 mmol; CASRN 823-58-5) and 4% aqueous NaOH solution (3 mL) was heated at reflux for 21 h, then cooled to RT. The pH was adjusted to 4 with glacial HOAc, then the mixture was partitioned between H₂O (20 mL) and EtOAc (30 mL). The aqueous layer was extracted with EtOAc (30 mL). The combined organic layers were dried (MgSO₄), filtered, and concentrated to give 0.082 g (73%) of 42a as a pink solid that was used without further purification.

step 2—A mixture of 42a (0.082 g, 0.56 mmol) and K₂CO₃ (0.117 g, 0.845 mmol) in DMF (3 mL) was treated with methyl iodide (0.035 mL, 0.56 mmol), stirred for 42 h, then diluted with H₂O (20 mL ). The mixture was twice extracted with EtOAc (20 mL each), and the combined organic layers were dried (MgSO₄), filtered, and concentrated. The crude product was purified by SiO₂ chromatography eluting with a EtOAc/hexane gradient (10 to 50% EtOAc) to afford 0.035 g (39%) of 42b as an off-white solid.

step 3—A mixture of 42b (0.035 g, 0.22 mmol), A-6 (0.102 g, 0.26 mmol), Na₂CO₃ (0.070 g, 0.66 mmol), and Pd(0) (PPh₃)₄ (0.025 g, 0.022 mmol) in DME (2 mL) and H₂O (1 mL) was stirred and heated at 170° C. for 30 min in microwave synthesizer. The mixture was partitioned between EtOAc (30 mL) and H₂O (30 mL). The aqueous layer was extracted with two 30 mL portions of EtOAc. The combined organic layers were dried (MgSO₄), filtered, and concentrated. The crude product was purified by SiO₂ chromatography eluting with a MeOH/DCM gradient (0 to 3% MeOH) to afford 0.079 g (92%) of 44 as a white solid. The material was not completely pure but was used as is in the next step.

step 4—A solution of 44 (0.039 g, 0.100 mmol) and DIPEA (0.044 mL, 0.25 mmol) in DCM (2.5 mL) cooled to 0-5° C. was treated with a 20% phosgene in toluene solution (0.25 mL, 0.55 mmol). The mixture was stirred for 10 min, then a 2 M methylamine in tetrahydrofuran solution (1.0 mL, 2.0 mmol) was added. The mixture was stirred for 1 h, treated with methanol, and adsorbed onto $SiO_2$. The $SiO_2$ was placed atop a $SiO_2$ flash column and eluted with a MeOH/EtOAc gradient (0 to 4% MeOH) to afford 0.039 g (87%) of impure I-23 as a white solid. This solid was combined with other batches and finally completely purified with a second $SiO_2$ chromatography eluting with a MeOH/DCM gradient (2 to 3% MeOH).

I-27 was prepared analogously except in step 4, the methylamine/THF solution was replaced with an ethylamine/THF solution.

EXAMPLE 11

4-tert-Butyl-N-{2-methyl-3-[1-methyl-5-(3 -methyl-ureido)-6-oxo-1,6-dihydro-pyridin-3-yl]-phenyl}-benzamide (II-4)

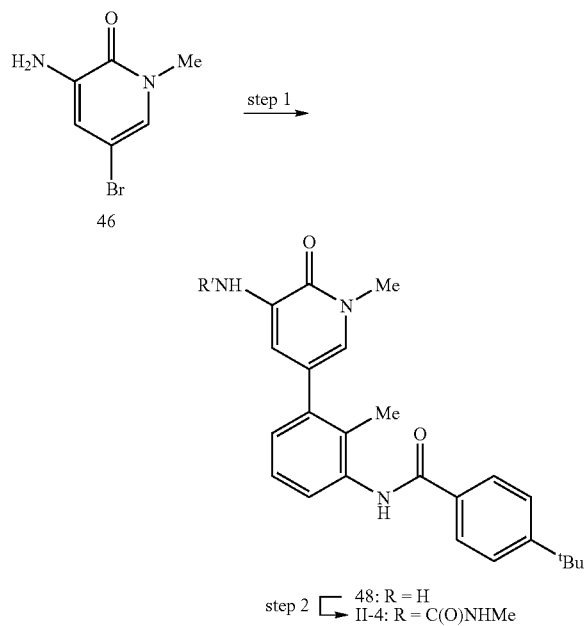

step 1—A mixture of 46 (0.248 g, 1.22 mmol, CASRN 910543-72-5), A-6 (0.574 g, 1.46 mmol), $Na_2CO_3$ (0.388 g, 3.66 mmol), and $Pd(0)(PPh_3)_4$ (0.141 g, 0.122 mmol) in DME (10 mL) and $H_2O$ (5 mL) was stirred and heated at 170° C. for 30 min in a microwave synthesizer. The mixture was partitioned between EtOAc (100 mL) and $H_2O$ (100 mL). The aqueous layer was extracted with two 100 mL portions of EtOAc. The combined organic layers were dried ($MgSO_4$), filtered and concentrated. The crude product was purified by $SiO_2$ chromatography eluting with a MeOH/DCM gradient (0 to 4% MeOH) to afford 0.341 g (72%) of 48 as a yellow solid. The material was not completely pure but was used as is in the next step.

step 2—A solution of 48 (0.136 g, 0.348 mmol) and DIPEA (0.15 mL, 0.87 mmol) in DCM (7 mL) at 0-5° C. was treated with a 20% phosgene solution in toluene (0.19 mL, 0.42 mmol). The mixture was stirred for 10 min, then a 2 M methylamine THF solution (0.87 mL, 1.8 mmol) was added. The mixture was stirred for 15 min, then adsorbed onto $SiO_2$. The crude product was purified by two $SiO_2$ chromatographies eluting first with a MeOH/EtOAc gradient (0 to 5% MeOH) then (0 to 3% MeOH) to afford 0.101 g (65%) of II-4 as a white solid.

II-5, II-6, II-7, II-8, II-9, II-16, II-18 and II-22 were prepared analogously except in step 2 methyl amine was replaced with ethylamine, iso-propylamine, 2,2,2 -trifluoro-ethylamine, aniline, benzyl amine, $N^1,N^1$-dimethyl-ethane-1,2-diamine, 3 -dimethylamino-propan-1-ol and $N^1,N^1$-dimethyl-propane-1,3-diamine respectively.

II-27 was prepared analogously except in step 1, A-6 was replaced with 4-tert-butyl-N-[3-(4,4,5,5-tetramethyl-[1,3,2]dioxaborolan-2-yl)-phenyl]-benzamide (49) which was prepared by acylation of 3-(4,4,5,5-tetramethyl-[1,3,2]dioxaborolan-2 -yl)-phenylamine with 4-tert-butyl-benzoyl chloride II-13 was prepared analogously except in the Suzuki coupling in step 1, A-6 was replaced with 56. II-21 was prepared analogously except in step 2, methyl amine was replaced with $N^1,N^1$-dimethyl-ethane-1,2-diamine II-15 was also prepared analogously except in step 1, A-6 was replaced with 6-dimethylamino-N-[3-(4,4,5,5-tetramethyl-[1,3,2]dioxaborolan-2-yl)-phenyl ]-nicotinamide prepared from 6-dimethylamino-nicotinoyl chloride and 14a as described in step 1 of example 14.

EXAMPLE 12

4,5,6,7-Tetrahydro-benzo[b]thiophene-2-carboxylic acid{2-methyl-3-[1-methyl-5-(3-methyl-ureido)-6-oxo-1,6-dihydro-pyridin-3-yl]-phenyl}-amide (II-11)

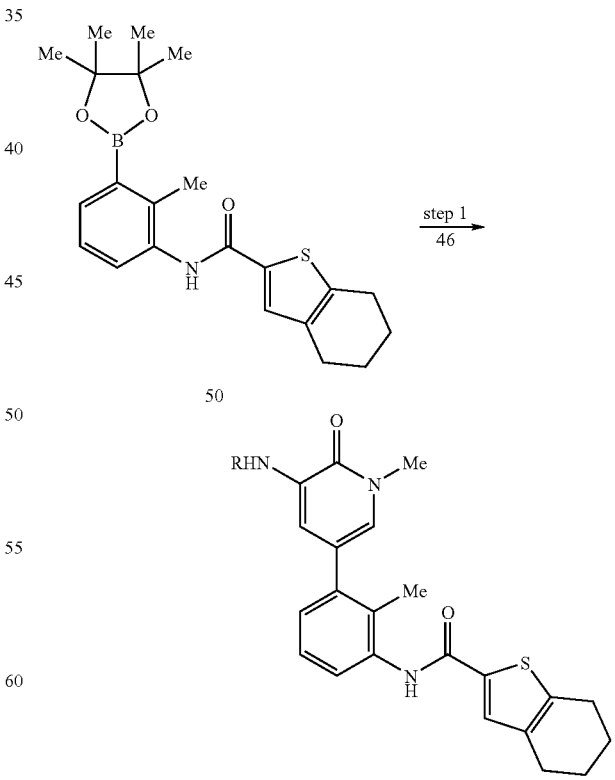

I-11 was prepared by Suzuki coupling of 46 and 50 and subsequently converting the amine the urea as described in steps 1 and 2 of example 11. II-10 and II-12 (dioxaborolane 38 was described in example 8) were prepared analogously except 50 was replaced with 53 (infra) and 38, respectively.

The requisite dioxaborolanes were prepared by acylation 14a (CASRN 882678-96-8) with 4,5,6,7-tetrahydrobenzo[b]thiophene-2-carbonyl chloride (CASRN 65361-26-4) and benzo[b]thiophene-2-carbonyl chloride (CASRN 39827-11-7).

Benzo[b]thiophene-2-carboxylic acid[2-methyl-3-(4,4,5,5-tetramethyl-[1,3,2]dioxaborolan-2-yl)-phenyl]-amide— To a solution of 14a (0.396 g, 1.7 mmol) and TEA (0.355 mL, 2.55 mmol) in THF (10 mL) was added a solution of benzo[b]-thiophene-2-carbonyl chloride (0.334 g, 1.7 mmol) in THF (2 mL). The white suspension was stirred for 1 h, then $H_2O$ (5 mL) was added. The mixture was partitioned between EtOAc (30 mL) and H2O (30 mL), and the aqueous layer was extracted with EtOAc (30 mL). The combined organic extracts were dried (MgSO4), filtered, and concentrated to a solid. The crude product was purified by SiO2 chromatography eluting with a EtOAc/hexane gradient (0 to 15% EtOAc) to afford 0.399 g (60%) of benzo[b]thiophene-2-carboxylic acid[2-methyl-3-(4,4,5,5-tetramethyl-[1,3,2]dioxaborolan-2-yl)-phenyl]-amide (53) as a white solid.

EXAMPLE 13

4-tert-Butyl-N-(2-methyl-3-{1-methyl-5-[5-(morpholine-4-carbonyl)-pyridin-2-ylamino]-6-oxo-1,6-dihydro-pyridin-3-yl}-phenyl)-benzamide (II-2)

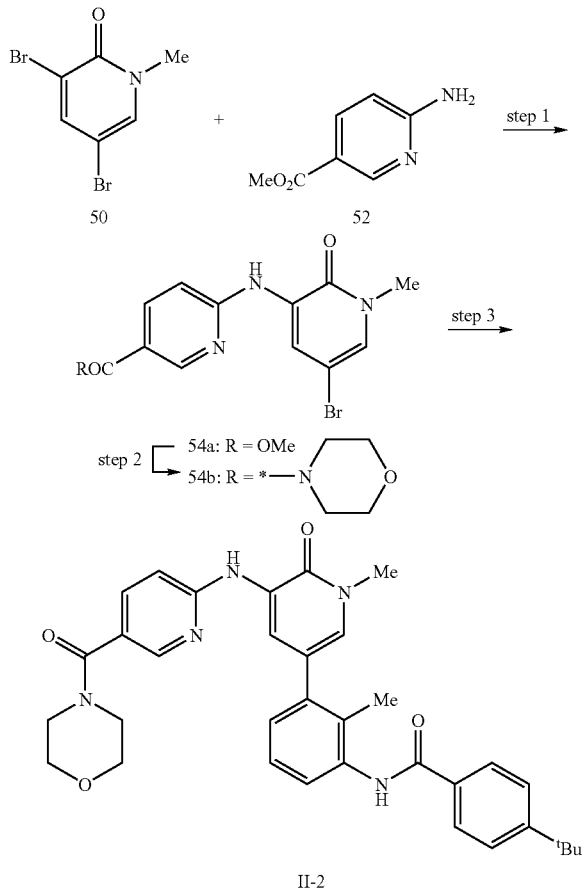

step 1—To a suspension of 50 (0.80 g, 3.0 mmol, CASRN 14529-54-5), methyl 6-amino-nicotinate (52, 0.55 g, 3.6 mmol, CASRN 36052-24-1) and toluene (10 mL) was added BINAP (0.140 g, 0.22 mmol), $Pd_2(dba)_3$ (0.137 g, 0.15 mmol), $Cs_2CO_3$ (1.37 g, 4.2 mmol). The glass reaction vessel was sealed and heated to 1300 C overnight. The reaction mixture was cooled, concentrated in vacuo and purified by $SiO_2$ chromatography eluting with 1% MeOH/DCM to afford 1.80 g of 54a.

step 2—To a solution of 54a (0.75 g, 2.22 mmol) and EtOH (100 mL) was added 3 N NaOH (2.22 mL). The solution was heated at reflux for 2 h, cooled, concentrated in vacuo and dried under a high vacuum. The residue was dissolved in DMF (50 mL) and EDCI (1.28 g, 6.65 mmol), HOBt (0.90 g, 6.66 mmol) and morpholine (0.29 mL, 3.33 mmol) were added and the resulting reaction mixture stirred at RT overnight. The solution was diluted with $H_2O$ (50 mL) and stirred overnight. The reaction mixture was extracted with DCM and the organic extracts washed with $Na_2CO_3$ and brine. The DCM solution was dried ($MgSO_4$), filtered and evaporated. The crude product was purified by $SiO_2$ chromatography eluting with 2% MeOH/DCM to afford 0.30 g of 54b.

step 3—A solution of 54b (0.110 g, 0.28 mmol), A-6 (0.132 g, 0.33 mmol), $Pd(0)(PPh_3)_4$ (0.032 g, 0.03 mmol) in 1 N $Na_2CO_3$ (1 mL) and DME (1 mL) was heated at 120C for 40 min in a microwave synthesizer. The solution was cooled and partitioned between EtOAc and $H_2O$. The organic extract was washed with brine, dried ($MgSO_4$), filtered and evaporated. The crude product was purified by $SiO_2$ chromatography eluting with 4% MeOH/DCM to afford 0.062 g of II-2.

II-1 and II-25 were prepared analogously except in step 2, morpholine was replaced with 1-methyl-piperazine and pyrrolidin-3-ol, respectively.

II-3 was prepared analogously except in step 1, methyl 6-amino-nicotinate was replaced with 2-amino-pyridine and step 2 was omitted.

II-36 was prepared analogously except in step 3, A-6 was replaced with 60 (see example 16). II-34 was prepared by Suzuki-mediated coupling of 54b and 14a. The resulting aryl amine was acylated with 4-tert-butyl-3-methoxy-benzoyl chloride to afford II-34 which was demethylated with $BBr_3$ to afford II-32.

II-48 is prepared analogously except in step 3, A-6 is replaced with 60 (Ar=4-dimethylamino-phenyl, see example 16).

II-95 is prepared analogously except in step I, 52 is replaced with pyridazin-3-ylamine and in step 3, A-6 is replaced with 120 (Ar=4-cyclopropyl-phenyl).

II-94 is except in step I, 52 is replaced with 3-amino-6-methyl-pyridazine and in step 3, A-6 is replaced with 120 (Ar=4-cyclopropyl-phenyl).

II-98 is except in step I, 52 is replaced with pyrazin-2-ylamine and in step 3, A-6 is replaced with 120 (Ar=4-cyclopropyl-phenyl).

II-103 is except in step I, 52 is replaced with 6-morpholin-4-yl-pyridazin-3-ylamine and in step 3, A-6 is replaced with 120 (Ar=4-cyclopropyl-phenyl).

EXAMPLE 14

4-Dimethylamino-N-(3-{5-[5-(4-hydroxy-piperidine-1-carbonyl)-pyridin-2-ylamino]-1-methyl-6-oxo-1,6-dihydro-pyridin-3-yl}-2-methyl-phenyl)-benzamide (II-20)

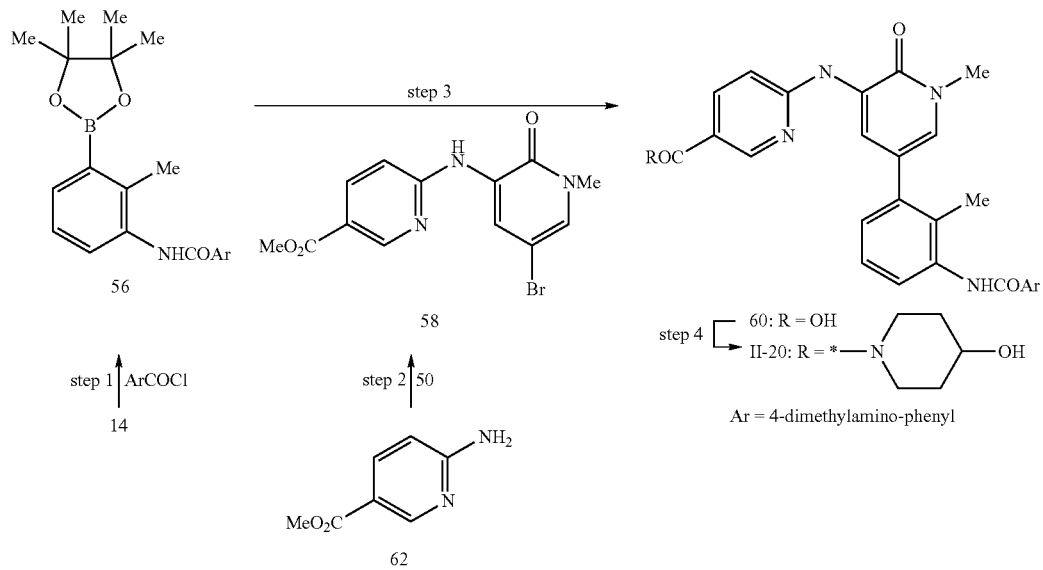

step 1—To a solution of 4-dimethylamino-benzoyl chloride (1.49 g, 8.15 mmol) and TEA (1.2 g, 12 mmol) and DCM (60 mL) under nitrogen was added 14a (1.9 g, 8.15 mmol). The mixture was stirred at RT for 16 h, then diluted with water and extracted with EtOAc. The organic layer was washed with brine, dried ($Na_2SO_4$), filtered and concentrated in vacuo. The residue was purified by $SiO_2$ chromatography eluting with a EtOAc/hexane gradient (10% to 50% EtOAc) affording 2 g (66%) of 56.

step 2—A suspension of 50 (5 g, 18.7 mmol) and 62 (3.4 g, 22.5 mmol) in toluene (60 mL) was sparged with argon, racemic BINAP (0.931 g, 1.5 mmol) was added followed by $Pd_2(dba)_3$ (0.514 g, 0.56 mmol) and sodium tert-butoxide (2.51 g, 26.18 mmol). The mixture was heated at 120° C. for 16 h. After cooling the reaction mixture was diluted with $H_2O$ (200 mL) and twice extracted with EtOAc (150 mL each). The organic layer was concentrated in vacuo, the residue triturated with EtOAc and filtered. The solid was washed with water, MeOH and EtOAc and dried to afford 6 g of 58 which used in the next step without further purification.

step 3—To a suspension of 56 (0.562 g, 1.47 mmol) and 58 (0.5 g, 1.47 mmol) in DME (10 mL) in a microwave tube was added a solution of $Na_2CO_3$ (0.467 g, 4.41 mmol) in $H_2O$ (3 mL). After sparging with argon, $Pd(0)(PPh_3)_4$ (0.085 g, 0.0735 mmol) was added, the tube was sealed and the reaction mixture was heated at 175° C. for 45 min in a microwave apparatus. The reaction mixture was partitioned between $H_2O$ and EtOAc. The aqueous layer was acidified with 4N HCl to ca. pH 5 and thrice extracted with EtOAc to afford 0.5 g (68%) of 60.

step 4—To a solution of 60 (0.1 g, 0.2 mmol) and anhydrous DMF (3 mL) maintained under a nitrogen a atmosphere was added BOP (0.088 g, 0.2 mmol) followed by TEA (0.060 g, 0.6 mmol) and piperidin-4-ol (0.02 g, 0.2 mmol). The mixture was stirred at RT for 6 h. After this time, the mixture was diluted with water, extracted with EtOAc, washed with brine and concentrated in vacuo. The residue was purified on a preparative TLC plate three times developed with 5% MeOH/DCM to afford 0.024 g (20%) of II-20 (yield 20%).

II-33 was prepared analogously except in step 4, 1-methyl-piperzine was used in place of piperidin-4-ol. II-35 was prepared analogously except in step 3, 56 is replaced with 88 (example 21) and in step 4,1-methyl-piperzine is used in place of piperidin-4-ol. II-87 is prepared analogously except in step 1 4-dimethylamino-benzoyl chloride is replaced with 4-cyclopropyl-benzoyl chloride and in step 4, 1-ethyl-piperzine is used in place of 1-methyl-piperzine.

II-60 is prepared analogously except in step 3, 56 is replaced with 106 and in step 4, piperidin-4-ol is replaced with 4-dimethylamino-piperidine.

II-99 is prepared analogously except in step 3, 56 is replaced with 106 and in step 4, piperidin-4-ol is replaced with pyrrolidine.

II-100 is prepared analogously except in step 3, 56 is replaced with 106 and in step 4, piperidin-4-ol is replaced with 3,3-difluoroazetidine (CASRN 679431-52-8).

II-101 is prepared analogously except in step 3, 56 is replaced with 106 and in step 4, piperidin-4-ol is replaced with azetidine.

EXAMPLE 15

1-Methyl-1H-indole-5-carboxylic acid{2-methyl-3-[1-methyl-5-(3-methyl-ureido)-6-oxo-1,6-dihydro-pyridin-3-yl]-phenyl}-amide (II-23)

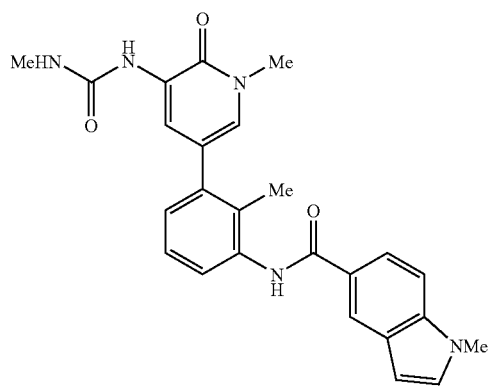

step 1—Sodium hydride (1.71 g, 42.80 mmol, 60% in mineral oil) was added at 0° C. in portions to a stirred solution of methyl indole-5-carboxylate (5.0 g, 28.53 mmol, CASRN 1670-81-1) in DMF over a 30 min period. While still at 0° C. MeI (5.33 mL, 85.61 mmol) was added. The resulting mixture was stirred at 0° C. for 60 min then at RT overnight. The mixture was partitioned between $H_2O$ and EtOAc and the aqueous layer was further extracted with EtOAc. The combined organic extracts were washed with water, dried ($MgSO_4$), filtered and concentrated to afford 4.91 g of 1-methyl-1H-indole-5-carboxylic acid methyl ester (53).

step 2—To the solution of 53 (4.90 g, 25.89 mmol) in $THF/H_2O$ was added 1N NaOH and the resulting mixture was heated at reflux for 60 min. The reaction mixture was cooled to 0° C., acidified with 1N HCl to ca. pH=3, and the mixture was partitioned between $H_2O$ and EtOAc and the combined organic layers were dried ($MgSO_4$), filtered and concentrated to afford 4.25 g of 1-methyl-1H-indole-5-carboxylic acid (55).

step 3—To a solution of 55 (0.608 g, 3.474 mmol, CASRN 186129-25-9) and DMF was added 14a (0.27 g, 1.158 mmol), DIPEA (0.60 mL, 3.474 mmol)) and HATU (0.484 g, 1.274 mmol). The reaction mixture was stirred at RT over night. The reaction mixture was partitioned between EtOAc and $H_2O$, the EtOAc phase was washed with brine, dried ($MgSO_4$), filtered and concentrated. The crude product was purified by $SiO_2$ chromatography eluting with 42% EtOAc/hexane to afford 236 mg of 59.

The synthesis of II-23 was completed by Suzuki coupling of 59 and 46 followed by sequential treatment with phosgene and methylamine as described in example 11

EXAMPLE 16

4-(Cyano-dimethyl-methyl)-N-{2-methyl-3-[1-methyl-5-(3-methyl-ureido)-6-oxo-1,6-dihydro-pyridin-3-yl]-phenyl}-benzamide (II-42)

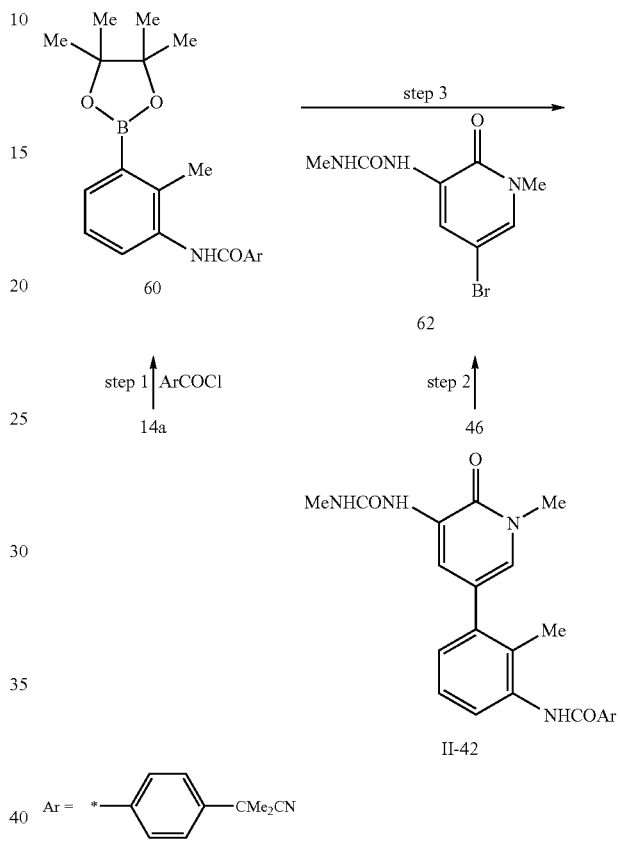

step 1—To a solution of 4-(cyano-dimethyl-methyl) benzoic acid (0.5 g, 2.64 mmol, CASRN 129488-74-0) and DMF (15 mL) was added BOP (1.16 g; 2.64 mmol), TEA (0.8 g; 7.92 mmol) and 14a (0.615 g, 2.64 mmol). The mixture was stirred at RT for 16 h, then diluted with EtOAc and washed with brine. The organic layer was dried ($Na_2SO_4$), filtered and concentrated in vacuo. The residue was triturated with EtOAc and the solid was filtered to afford 0.650 g (61%) of 60. Additional impure product (0.3 g) was recovered from filtrate.

step 2—To a solution of 46 (0.5 g, 2.46 mmol), DIPEA (0.952 g; 7.38 mmol) and DCM (40 mL) cooled to 0° C. under a nitrogen atmosphere was added phosgene (1.8 mL, 3.69 mmol, 20% in toluene). The reaction mixture was stirred for 20 min then methylamine (12 mL, 24.6 mmol, 2M solution in THF) was added slowly. The mixture warmed to RT and stirred for 5 h. The product was filtered, washed with DCM and dried in vacuo to afford 0.8 g (99%, 80% pure) of 62 which was used in the following step without further purification.

step 3—To a suspension of 60 (0.153 g, 0.38 mmol) and 62 (0.125 g, 0.38 mmol) in DME (3 mL) in a microwave tube was added Na$_2$CO$_3$ (0.120 g, 1.14 mmol) in H$_2$O (1.5 mL). After sparging with argon, Pd(0)(PPh$_3$)$_4$ (22 mg, 0.019 mmol) was added, the tube was sealed and the mixture heated at 175° C. in a microwave apparatus. The reaction mixture was cooled, diluted with water and extracted with EtOAc. The organic layer was concentrated and the precipitate filtered and washed with H$_2$O (2 mL), MeOH (2 mL) and DCM (4 mL), then dried, to afford 0.058 g (33%) of H-42.

EXAMPLE 17

4-(1-Hydroxy-1-methyl-ethyl)-N-{2-methyl-3-[1-methyl-5-(3-methyl-ureido)-6-oxo-1,6-dihydro-pyridin-3-yl]-phenyl}-benzamide (II-28)

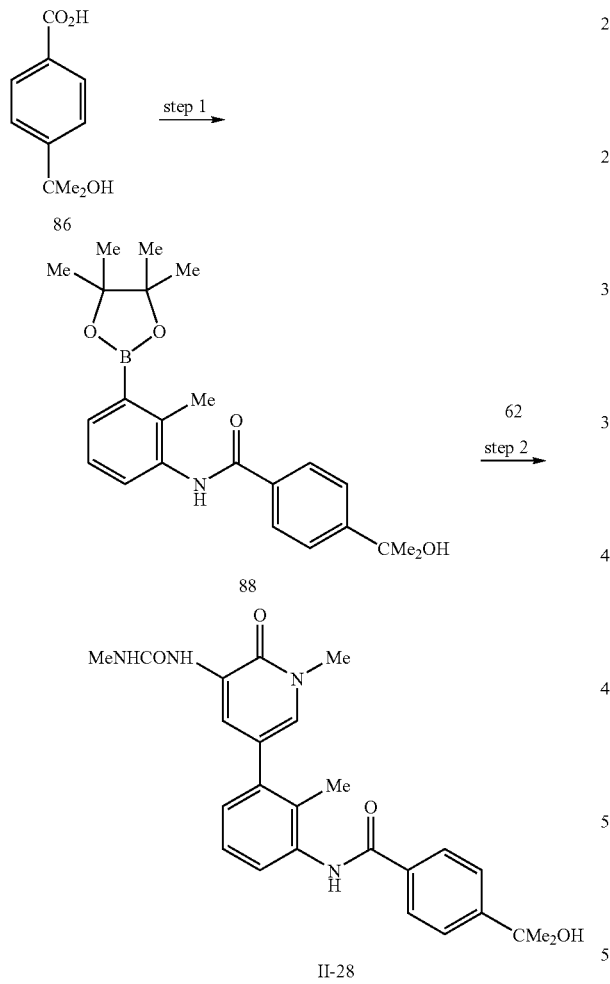

step 1—A solution of 86 (2.10 g, 11.653 mmol) and 14a in DMF (30 mL) was stirred at RT and DIPEA (5.53 mL, 31.78 mmol) and HATU (4.43 g, 11.65 mmol) were added and the resulting mixture was stirred at RT over night. The mixture was partitioned between H$_2$O (150 mL) and EtOAc (150 mL). The aqueous layer was further extracted with 50 mL of EtOAc. The combined organic extracts were thrice washed with H$_2$O (50 mL each), dried (MgSO$_4$), filtered and concentrated to afford 2.90 g of 88.

The Suzuki coupling of 88 and 62 was carried out as described in step 3 of example 16.

EXAMPLE 18

5-{3-[2-(1,3-Dihydro-isoindol-2-yl)-2-oxo-ethyl]-phenyl}-1-methyl-3-[5-(morpholine-4-carbonyl)-pyridin-2-ylamino]-1H-pyridin-2-one (II-24)

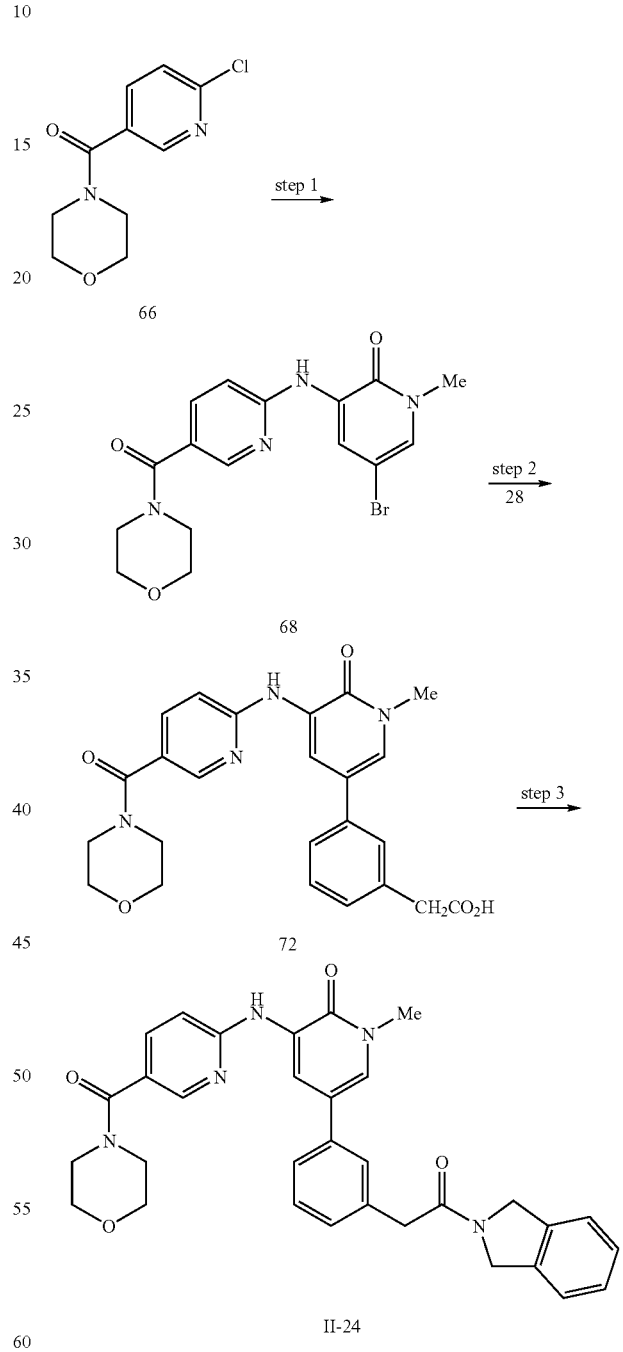

(6-chloro-pyridin-3-yl)-morpholin-4-yl-methanone

To a solution of 6-chloronicotinic acid (25.0 g, 142 mmol) and DCM cooled to a 0° C. was added morpholine (13.6 g, 156 mmol) and TEA (28.7 g, 284 mmol). After stirring for 2 h at 0° C., the solution was washed with aqueous NaHCO₃, dried (MgSO₄), filtered and concentrated in vacuo to afford 29.5g (130 mmol) of 66: MS (ESI) 227.1 (M+H)⁺.

step 1—To a 0° C. solution of 66 (14.00 g, 61.77 mmol) and 46 (12.54 g, 61.77 mmol) in DMF (160 mL) was added sodium hydride (95%, 3.12 g, 123.5 mmol). This solution was slowly warmed to RT, stirred for 18 h then poured into 1.3 L cold water. EtOAc (3mL) was added and the resulting precipitate was filtered, washed with water, and air dried for 3 d to afford 18.84 g (47.91 mmol) of 68: MS (ESI) 393.1 (M+H)⁺.

The Suzuki coupling of 68 and 28 was carried out as described in step 1 of example 8 to afford 72 which was converted to II-24 by EDCI coupling of 2,3-dihydro-1H-isoindole using the protocol described in step 2 of example 14.

II-26, II-40 and II-41 were prepared analogously except 6,7-dihydro-5H-pyrrolo[3,4-b]pyridine (CASRN 147739-88-6,3-tert-butoxy-cyclobutylamine and 3-iso-propoxy-cyclobutylamine respectively were used in place of 2,3-dihydro-1H-isoindole.

EXAMPLE 19

N-(2-tert-Butoxy-ethyl)-2-(2-methyl-3-{1-methyl-5-[5-(morpholine-4-carbonyl)-pyridin-2-ylamino]-6-oxo-1,6-dihydro-pyridin-3-yl}-phenyl)-acetamide (II-39)

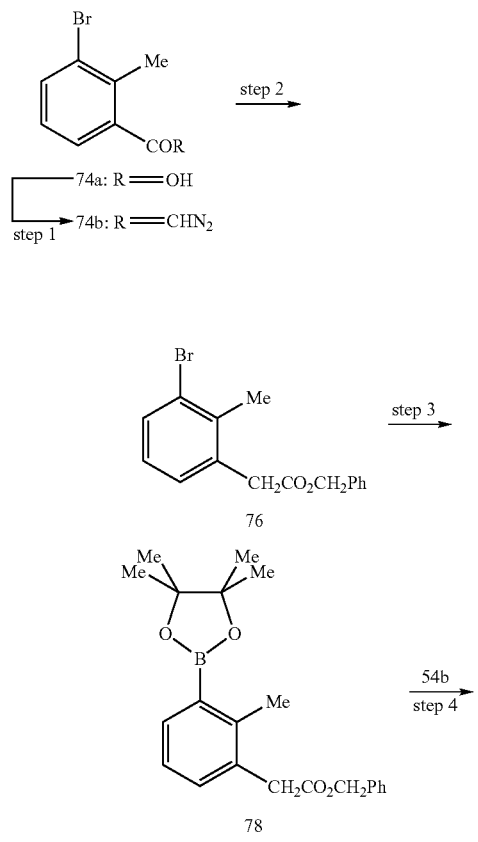

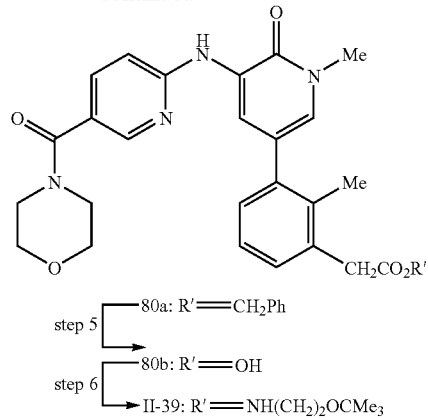

step 1—To a solution of 74a (1.00 g, 4.65 mmol) in DCM (15 mL) was added oxalyl chloride (649 mg, 5.12 mmol) and 4 drops DMF. After 40 min, the resulting mixture was concentrated in vacuo. The residue was dissolved in toluene (20 mL) and (trimethylsilyl)diazomethane solution (6.30 mL, 12.6 mmol, 2.0M in Et₂O) was added. After stirring for 3 d, the solution was partitioned between EtOAc and H₂O. The organic layer was washed with brine, dried (MgSO₄), filtered and concentrated in vacuo. The crude product was purified by SiO₂ chromatography and eluted with a EtOAc/hexane gradient (50 to 100% EtOAc) to afford 0.394 g of 74b: MS (ESI) 238.9 (M−H).

step 2—A solution of 74b (115 mg, 0.479 mmol) in benzyl alcohol (0.5 mL) and 2,4,6-collidine (0.5 mL) was heated to 180° C. for 7 min in a microwave synthesizer. The resulting solution was partitioned between EtOAc and 1M aq. HCl. The organic layer was washed with water and brine, dried (MgSO₄), filtered and concentrated in vacuo. The crude product was purified by SiO₂ chromatography eluting with 5% EtOAc/hexanes to afford 0.072 g of 76:

¹HNMR (300 MHz, CDCl₃) δ 2.36 (s, 3H), 3.73 (s, 2H), 5.14 (s, 2H), 7.00 (t, J=8 Hz, 1H), 7.14 (d, J=8 Hz, 1H), 7.26-7.36 (m, 5H), and 7.49 ppm (d, J=8 Hz, 1H).

step 3—To a solution of 76 (200 mg, 0.626 mmol), bis-(pinacolato)diboron (191 mg, 0.752 mmol), KOAc (184 mg, 1.88 mmol) in DMSO (4 mL) was added a solution of [1,1'-bis-(diphenylphosphino) ferrocene]dichloropalladium(II) in DCM (15 mg, 0.018 mmol) and the resulting solution was heated at 80° C. under an atmosphere of argon for 2 h. The resulting solution was partitioned between EtOAc and H₂O. The organic layer was washed with brine, dried (MgSO₄), filtered and concentrated in vacuo. The crude product was purified by SiO₂ chromatography eluting with 4% EtOAc/hexanes to afford 0.094 g of 78: MS (ESI) 389.2 (M+Na)⁺.

step 4—A solution of 54b (99 mg, 0.25 mmol), 78 (92 mg, 0.25 mmol), Pd(0)(PPh₃)₄(29 mg, 0.025 mmol), and Na₂CO₃ (80 mg, 0.75 mmol) in DME (3 mL) and H₂O (1 mL) was heated at 170° C. for 10 min in a microwave synthesizer. The resulting mixture was partitioned between EtOAc and water. The EtOAc layer was washed with brine, dried (MgSO₄), filtered and concentrated in vacuo. The crude product was purified by on a preparative TLC plate developed with 5% MeOH/DCM) to afford 36 mg of 80a: MS (ESI) 553.2 (M+H)⁺.

step 5—A suspension of 80a (36 mg, 0.065 mmol) and 10% Pd/C (22 mg) and EtOH (15 mL) was stirred under H₂ atmosphere for 2 h. The resulting mixture was filtered and concentrated in vacuo to afford 0.020 g of 80b: MS (ESI) 463.1 (M+H)⁺.

step 6—To a solution of 80b (30 mg, 0.065 mmol), BOP (29 mg, 0.066 mmol), and 2-tert-butoxy-ethylamine hydrochloride (10 mg, 0.065 mmol, CASRN 335598-67-9) in DMF (2 mL) was added TEA (33 mg, 0.33 mmol). The solution was stirred at RT for 5 h and the resulting mixture was partitioned between EtOAc and aqueous NaHCO₃. The EtOAc layer was washed with brine, dried MgSO₄, filtered and concentrated in vacuo. The crude product was purified on a preparative SiO₂ TLC plate developed with 5% MeOH/DCM) to afford 0.0092 g of II-39: MS (ESI) 562 (M+H)⁺.

II-43 was prepared analogously except in step 6, 2-tert-butoxy-ethylamine hydrochloride was replaced with 2,3-dihydro-1H-isoindole

EXAMPLE 20

6-Dimethylamino-N-{2-methyl-3-[1-methyl-5-(3-methyl-ureido)-6-oxo-1,6-dihydro-pyridin-3-yl]-phenyl}-nicotinamide (II-15)

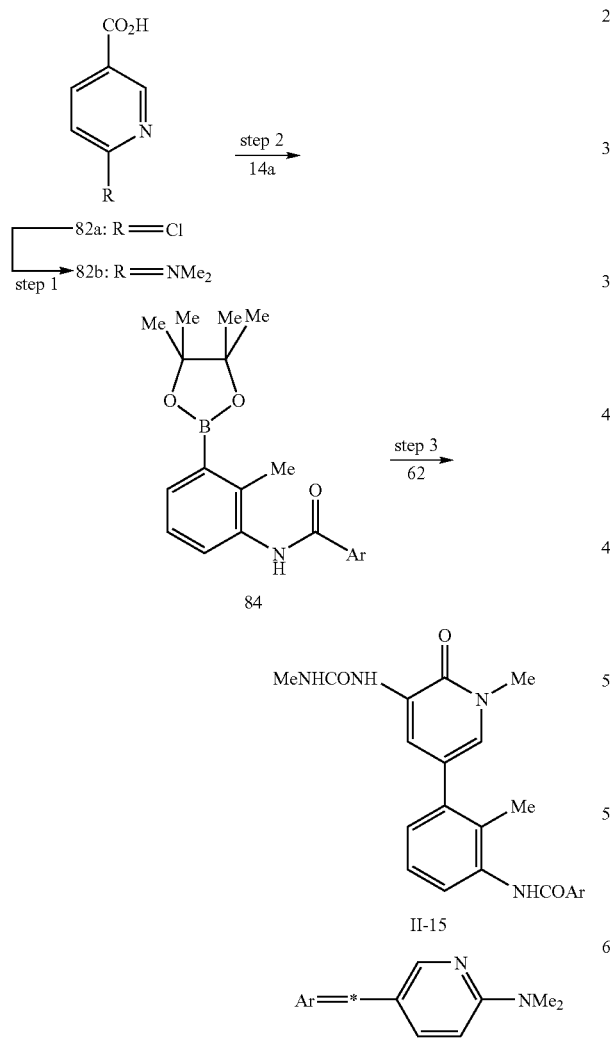

step 1—To a solution of 82a (1.0 g, 6.34 mmol) and THF (15 mL) was added Me₂NH (6.35 mL, 12.69 mmol; 2.0 M solution in THF) and the mixture was stirred in a microwave and heated to 150° C. for 45 min. The solvent was evaporated to afford 1.0 g of 82b which was used in the next step.

step 2—A solution of 82b (0.60 g, 3.61 mmol) and 14a (0.280g, 1.20 mmol) and DMF (20 mL) was stirred at RT. DIPEA (0.63 mL, 3.61 mmol) and HATU (0.50 g, 1.32 mmol) were added sequentially and the resulting mixture was stirred at RT overnight. The mixture was partitioned between H₂O and EtOAc. The aqueous layer was separated and further extracted with EtOAc (50 mL). The combined organic extracts were thrice washed with H₂O (50 mL each), dried (MgSO₄), filtered and concentrated. The crude product was purified by SiO₂ chromatography eluting with a EtOAc/hexanes gradient (0-50% EtOAc) to afford 0.140 g of 84.

The Szuki coupling of 84 and 62 was carried out as described in step 4 of example 17.

II-19 was prepared analogously except in step 1, dimethylamine was replaced with piperidine.

II-50 can be prepared analogously except 84 is replaced with 4-tert-Butyl-N-[2-methyl-3-(4,4,5,5-tetramethyl-[1,3,2]dioxaborolan-2-yl)-phenyl]-benzamide and 62 is replaced with 1-(5-Bromo-2-oxo-1,2-dihydro-pyridin-3-yl)-3-methyl-urea

EXAMPLE 21

N-(2-Hydroxymethyl-3-{1-methyl-6-oxo-5-[5-(piperazine-1-carbonyl)-pyridin-2-ylamino]-1,6-dihydro-pyridin-3-yl}-phenyl)4-(2,2,2-trifluoro-1,1-dimethyl-ethyl)-benzamide (II-81)

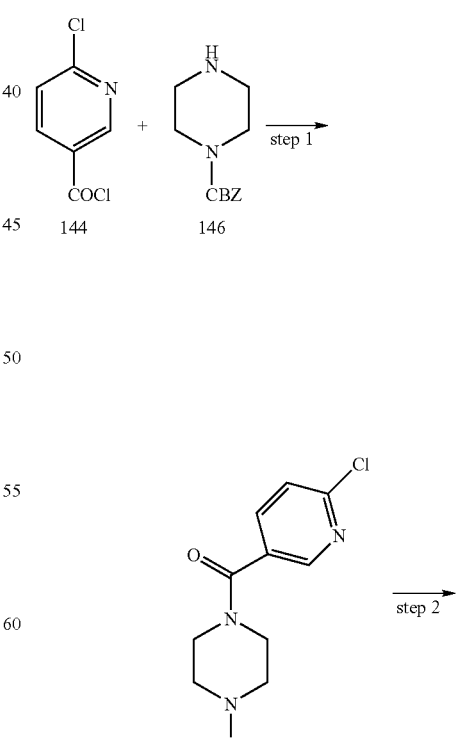

-continued

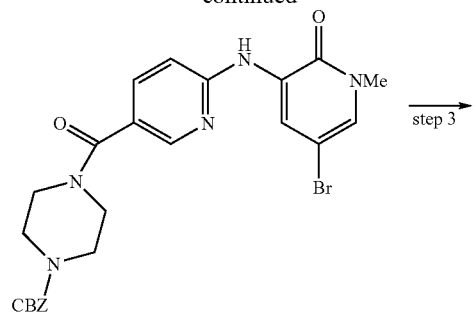

150

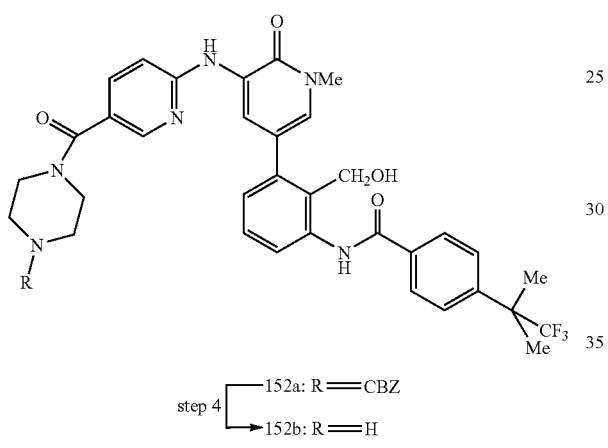

step 1—To a solution of 144 (2.16 g, 12.27 mmol) and TEA (3.42 mL, 2 eq) in DCM (50 mL) at 0° C. was added 146 (2.42 mL, 1 eq) and the resulting mixture was stirred and warmed from 0° C. to RT over one h. The DCM was removed under reduced pressure at 55° C. and the residue partitioned between EtOAc (200 mL) and water (50 mL) The organic phase was washed sequentially with water (2×50 mL), saturated NaHCO$_3$ (3×50 mL) and brine (1×50 mL). The organic layer was dried (MgSO4), filtered, and concentrated to afford 4.4 g of 148 as a viscous colorless oil.

step 2—Condensation of 148 and 46 can be carried out as described in step 1 of example 18 to afford 150.

step 3—Palladium-catalyzed coupling of 120 (Ar=4-(2,2,2 - trifluoro-1,1-dimethyl-ethyl)-phenyl) and 150 can be carried out as described in step 5 of example 25 to afford 152a.

step 4—A solution of 152a (73 mg, 0.093 mmol) in EtOH (40 mL) and THF (10 mL) and was purged with nitrogen gas for five min then 10% Pd/C carbon (50 mg) was carefully added. The resulting mixture was stirred under 1 atm of hydrogen gas (balloon) at RT for about 18 h. The mixture was filtered through a 3 cm bed of SOLKA-FLOC and the filtrate was oncentrated. The crude product was purified on a preparative SiO$_2$ TLC plate developed with 30% MeOH/DCM to afford 7 mg of II-81 as an off-white powder.

II-82 is prepared analogously except 152b is formylated with one equivalent of acetic formic mixed anhydride.

EXAMPLE 22

1-(5-{3-[2-(3-tert-Butoxy-azetidin-1-yl)-2 -oxo-ethyl]-phenyl}-1-methyl-2-oxo-1,2 -dihydro-pyridin-3-yl)-3-methyl-urea (II-29)

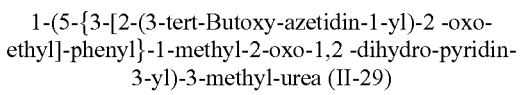

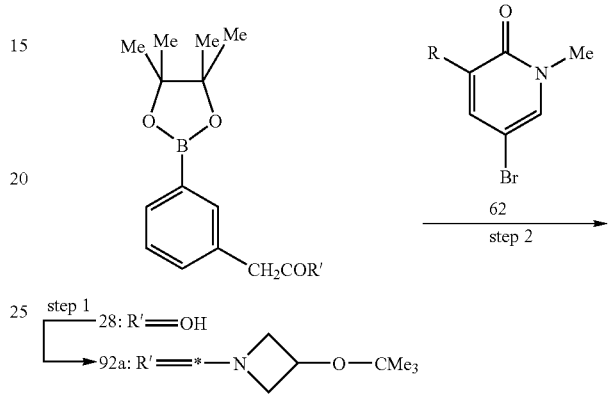

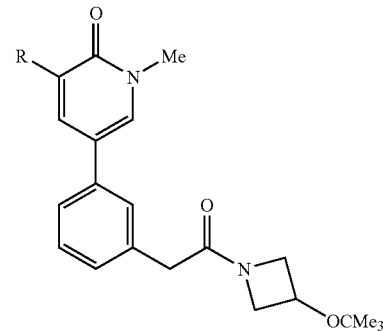

II-29

R═MeNHCONH—

The title compound is prepared by Suzuki coupling (step 2) of 92a and 62 using the protocol described in step 1 of example 6. The amide 92a is prepared (step 2) by BOP-mediated coupling of 28 and 3-tert-butoxy-azetidine using the protocol described in step of example 6.

II-30 (3-iso-propoxy-azetidine) and II-31 (5,6-dichloro-2,3 -dihydro-1H-isoindole) were prepared analogously except in step 2, 3-tert-butoxy-azetidine was replaced by the secondary amine in parenthesis.

II-45 and II-46 can be prepared analogously except in step 1, 28 is coupled with 2H-isoindole and 5-fluoro-2H-isoindole respectively.

II-47 can be prepared analogously except in step 1, 28 is coupled with azetindin-3-yl-propan-2-ol using HATU as described in example 21.

EXAMPLE 23

1,3-Dihydro-isoindole-2-carboxylic acid{2-methyl-3-[1-methyl-5-(3-methyl-ureido)-6-oxo-1,6-dihydro-pyridin-3-yl]-phenyl}-amide (II-17)

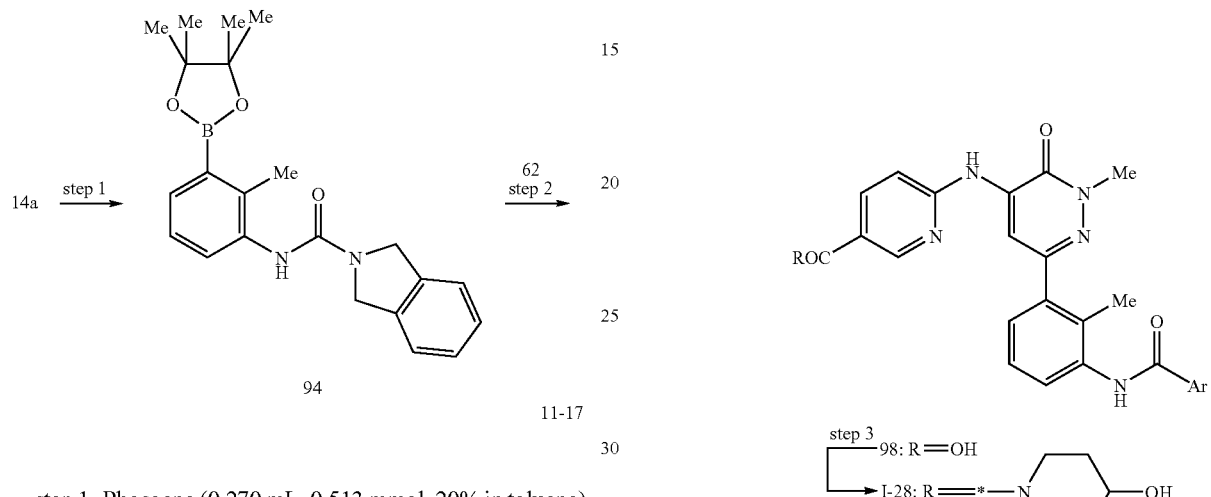

step 1—Phosgene (0.270 mL, 0.513 mmol, 20% in toluene) was added to a solution of 14a (0.100 g, 0.43 mmol) and TEA (0.150 mL, 1.08 mmol) in DCM (6 mL) cooled to 0-5° C. The reaction mixture was stirred for 10 min, then 2,3-dihydro-1H-isoindole (0.122 mL, 1.08 mmol) was added. The brown mixture was stirred at 0-5° C. for 10 min. To the solution was added SiO₂ (10 g) of silica gel and the mixture was concentrated to a powder. The resulting solid was applied to the top of a SiO₂ column eluting with a EtOAc/hexanes gradient (0 to 40% EtOAc) to afford 0.150 g (92%) of 94 as a dark brown solid that was used without further purification.

Suzuki coupling of 14a and 94 was carried out utilizing the protocol described in step 1 of example 6 to afford II-17.

II-14 was prepared analogously except in step 1,2,3-dihydro-1H-isoindole was replaced by 5-fluoro-2,3-dihydro-1H-isoindole (CASRN 57584-71-1).

EXAMPLE 24

4-Dimethylamino-N-(3-{5-[5-(4-hydroxy-piperidine-1-carbonyl)-pyridin-2-ylamino]-1-methyl-6-oxo-1,6-dihydro-pyridazin-3-yl}-2-methyl-phenyl)-benzamide (I-28)

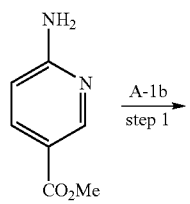

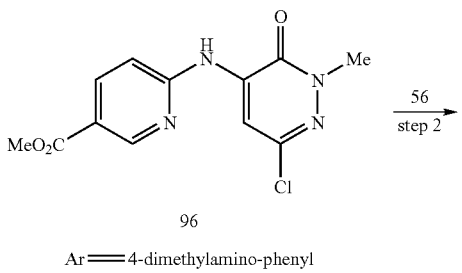

step 1—To a solution methyl 6-amino-nicotinate (0.234 g, 1.53 mmol) and DMF (4 mL) cooled to 0° C. was added NaH (61.2 mg, 60% mineral oil dispersion) and the solution warmed to RT and stirred for 0.5 h. The resulting solution was re-cooled to 0° C. and a solution of A-1b (0.137 g, 0.76 mmol) and DMF (1 mL) was added and the resulting solution stirred for 4 h at RT. The solution was diluted with EtOAc and brine which resulted in the formation of an insoluble solid which was filtered and dried to afford 0.140 g of 96.

step 2—To a suspension of 96 (0.140 g, 0.47 mmol) and 56 (0.1809 g, 0.47 mmol) in microwave tube containing DME (5 mL) was added a solution of Na₂CO₃ in water (2 mL). The tube was flushed with N2 and Pd(0)(PPh₃)₄ (0.050, 0.047 mmol) was added and the tube sealed and heated to 175° C. for 45 min in a microwave. The resulting mixture was cooled to RT and partition between EtOAc and brine. The ester hydrolyzed during the coupling procedure and the aqueous brine solution was acidified with 2N HCl, extracted with EtOAc. The aqueous solution was extracted with EtOAc and the combined extracts were dried (Na₂SO₄), filtered and evaporated to afford 0.060 g of 98.

step 3—To a solution of 98 (0.060 g, 0.12 mmol) and BOP (0.053 g, 0.12 mmol) in DMF (3 mL) was added 4-hydroxy-piperidine (0.012 g, 0.21 mmol) and TEA (0.036 g, 0.36 mmol) and the resulting solution was stirred at RT for 8 h. The solution was partition between EtOAc and brine. The EtOAc phase was dried (Na₂SO₄), filtered and evaporated. The crude product was purified on a preparative SiO₂ plate developed with 5% MeOH/DCM and eluted to afford I-28.

EXAMPLE 25

4-Dimethylamino-N-(2-hydroxymethyl-3-{1-methyl-5-[5-(morpholine-4-carbonyl)-pyridin-2-ylamino]-6-oxo-1,6-dihydro-pyridin-3-yl}-phenyl)-benzamide (II-49)

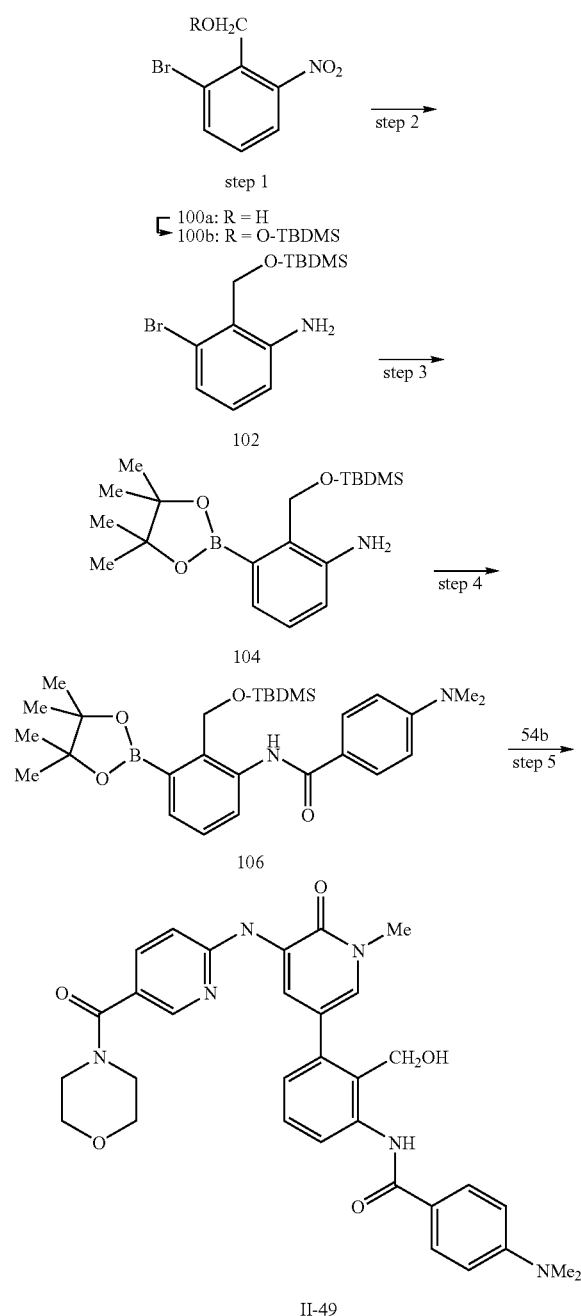

step 1—To a solution of above 100a (1.1 g, 4.74 mmol, CASRN 861106-914) in DCM (10 mL) were added sequentially ᵗBuMe₂SiCl (0.86 g, 5.69 mmol) and TEA (0.8 mL, 5.69 mmol). The resulting mixture was stirred at RT until the reaction was complete. The reaction mixture was partitioned between EtOAc (150 mL) and water (100 mL). The organic layer was dried (MgSO₄), filtered and concentrated. The residue was then purified by SiO₂ chromatography eluting with an EtOAc/hexane gradient (0 to 50% EtOAc) to afford 1.5 g of 100b.

step 2—A mixture of the 102b (1.5 g, 6.46 mmol), iron powder (1.08 g, 19.4 mmol) and ammonium chloride (1.73 g, 32.3 mmol) in EtOH (25 mL) and water (25 mL) was heated at 70° C. for 2 h. The mixture was filtered and extracted with EtOAc (100 mL). The organic layer was dried (MgSO₄), filtered and concentrated to afford 0.87 g of 102.

step 3—A mixture of the 102 (0.87 g, 2.76 mmol), PdCl2 (dppf) (10 mg, 0.012 mmol), pinacol diborane (0.84 g, 3.31 mmol), KOAc (0.974 g, 9.94 mmol) in DMSO (4 mL) was heated at 70° C. overnight. The mixture was then partitioned between EtOAc (100 mL) and water (100 mL). The organic layer was dried (MgSO₄), filtered and concentrated. The residue was purified by SiO₂ chromatography eluting with an EtOAc/hexane gradient (0 to 30% EtOAc) to afford 0.090 g of 104.

step 4—To a mixture of 104 (90 mg, 0.248 mmol) and p-N,N-dimethylamino-benzoyl chloride (45 mg, 0.248 mmol) in DCM (3 mL), was added dropwise TEA (54 µL, 0.372 mmol). The resulting solution was stirred at RT for 0.5 h and purified by SiO₂ chromatography eluting a EtOAc/hexane gradient (0 to 50% EtOAc) to afford 100 mg of 106.

step 5—A mixture of above 106 (100 mg, 0.196 mmol), 54b (77 mg, 0.196 mmol), Pd(Ph₃P)₄ (10 mg, 0.009 mmol), and Na₂CO₃ (62 mg, 0.588 mmol) in DME (1.5 mL) and water (1.5 mL) was heated at 170° C. for 0.5 h in a microwave. The resulting mixture was partitioned between EtOAc (100 mL) and water (100 mL). The organic layer was then dried (MgSO₄), filtered and concentrated. The residue was purified on a preparative SiO₂ TLC plate developed with 8% MeOH/DCM to afford 0.035 g of II-49 as white solid: MS: 583 (M+1)⁺.

II-52 can be prepared analogously to the procedure described in example 25, except in step 4, p-N,N-dimethylamino-benzoyl chloride is replaced with 4-(1-fluoro-1-methyl-ethyl)-benzoyl chloride. The latter is prepared from 4-(1-fluoro-1-methyl-ethyl)-benzoic acid (CASRN 477219-30-0) by standard methodology.

II-53 is prepared analogously to the procedure described in example 25, except in step 4, p-N,N-dimethylamino-benzoyl chloride is replaced with 4-(1-fluoro-cyclopropyl)-benzoyl chloride. The latter is prepared from 4-(1-fluoro-cyclopropyl)-benzoic acid (CASRN 946118-80-5) by standard methodology.

II-74 is prepared analogously to the procedure described in example 25, except in step 4, p-N,N-dimethylamino-benzoyl chloride is replaced with 4-trichloromethyl-benzoyl chloride.

II-75 is prepared analogously to the procedure described in example 25, except in step 4, p-N,N-dimethylamino-benzoyl chloride is replaced with 4-(1-chloro-cyclopropyl)-benzoyl chloride.

II-55 is prepared analogously to the procedure described in example 25, except in step 4, p-N,N-dimethylamino-benzoyl chloride is replaced with 4-trifluoromethyl-benzoyl chloride (CASRN 329-15-7).

II-58 is prepared analogously to the procedure described in example 25, except in step 4, p-N,N-dimethylamino-benzoyl chloride is replaced with 4-tert-butyl-benzoyl chloride (CASRN 329-15-7).

II-64 is prepared analogously except in step 4, p-N,N-dimethylamino-benzoyl chloride is replaced with is replaced with 4-(1-fluoro-cyclopropyl)-benzoyl chloride and in step 5, 54b is replaced with 5-bromo-1-methyl-3-(pyridin-2-ylamino)-1H-pyridin-2-one.

II-59 can be prepared analogously except in step 5, 54b is replaced with 5-bromo-1-methyl-3-(pyridin-2-ylamino)-1H-pyridin-2-one which is prepared as described in step 1 of example 13 wherein methyl 6-amino-nicotinate is replaced by 2-amino-pyridine.

II-62 is prepared analogously to the procedure described in example 25, except in step 4, p-N,N-dimethylamino-benzoyl chloride is replaced with 4-cyclopropyl-benzoyl chloride (CASRN 76274-96-77).

II-63 is prepared analogously to the procedure described in example 25, except in step 4, p-N,N-dimethylamino-benzoyl chloride is replaced with 4-bromo-benzoyl chloride.

II-66 is prepared analogously to the procedure described in example 25, except in step 4, p-N,N-dimethylamino-benzoyl chloride is replaced with 4-(1-methoxy-1-methyl-ethyl)-benzoyl chloride. The latter is prepared from 4-(1-methoxy-1-methyl-ethyl)-benzoic acid (CASRN 50604-11-0) by standard methodology.

II-67 is prepared analogously to the procedure described in example 25, except in step 4, p-N,N-dimethylamino-benzoyl chloride is replaced with benzoyl chloride.

II-68 is prepared analogously to the procedure described in example 25, except in step 4, p-N,N-dimethylamino-benzoyl chloride is replaced with 4-(1,2,2,2-tetrafluoro-1-trifluoromethyl-ethyl)-benzoyl chloride (CASRN 62480-31-3).

II-69 is prepared analogously to the procedure described in example 25, except in step 4, p-N,N-dimethylamino-benzoyl chloride is replaced with 4-ethynyl-benzoyl chloride (CASRN 62480-31-3).

II-96 is prepared analogously to the procedure described in example 25, except in step 4, p-N,N-dimethylamino-benzoyl chloride is replaced with 4-(cyano-dimethyl-methyl)-benzoyl chloride (CASRN 129488-75-1).

II-89 is prepared analogously to the procedure in example 25, except in step 4, p-N,N-dimethylamino-benzoyl chloride is replaced 4-pentafluorothio-benzoic acid and the coupling of the carboxylic acid to 104 is carried out with HATU as described in step 1 of example 21.

II-76 is prepared analogously to the procedure described in example 25, except in step 4, p-N,N-dimethylamino-benzoyl chloride is replaced with trimethylsilyl-benzoic acid (CASRN 15290-29-6) and the coupling of the carboxylic acid to 104 is carried out with HATU as described in step 1 of example 21.

II-97 is prepared analogously to the procedure described in example 25, except in step 4, p-N,N-dimethylamino-benzoyl chloride is replaced with 4-piperidin-1-yl-benzoic acid (CASRN 22090-24-0) and the coupling of the carboxylic acid to 104 is carried out with HATU as described in step 1 of example 21.

II-90 is prepared by palladium-catalyzed coupling of 50 and 2-amino-6-ethoxy-pyridine (CASRN 768-42-3) which can be carried out as described in step 1 of example 13 to afford 5-bromo-3-(6-ethoxy-pyridin-2-ylamino)-1-methyl-1H-pyridin-2-one (105). Condensation of 105 with 120 (Ar is 4-cyclopropyl-phenyl) is carried out as described in step 5 of the present example.

II-91 is prepared by palladium-catalyzed coupling of 50 and 6-amino-2-ethyl-2H-pyridazin-3-one (CASRN 50500-52-2) which can be carried out as described in step 1 of example 13 to afford 6-(5-bromo-1-methyl-2-oxo-1,2-dihydro-pyridin-3-ylamino)-2-ethyl-2H-pyridazin-3-one (107). Condensation of 107 with 120 (Ar is 4-cyclopropyl-phenyl) is carried out as described in step 5 of the present example.

II-93 is prepared by coupling of 42b and 2-benzyl-6-chloro-2 H-pyridazin-3-one which can be carried out as described in step 1 of example 10 to afford 2-benzyl-6-(5-chloro-1-methyl-2-oxo-1,2-dihydro-pyridin-3-ylamino)-2H-pyridazin-3-one (109). Condensation of 109 with 120 (Ar is 4-cyclopropyl-phenyl) is carried out as described in step 5 of the present example.

II-102 is prepared analogously except in step 5, 106 is replaced with 1,3-Dihydro-isoindole-2-carboxylic acid[2-(tert-butyl-dimethyl-silanyloxymethyl)-3-(4,4,5,5-tetramethyl-[1,3,2]dioxaborolan-2-yl)-phenyl]-amide which can be prepared treating 104 sequentially with phosgene and 2,3-dihydro-1H-isoindole according to the procedure in step 1 of example 23.

EXAMPLE 26

N-(2-Hydroxymethyl-3-{1-methyl-5-[5-(morpholine-4-carbonyl)-pyridin-2-ylamino]-6-oxo-1,6-dihydro-pyridin-3-yl}-phenyl)-4-(2,2,2-trifluoro-1-methyl-ethyl)-benzamide (II-51)

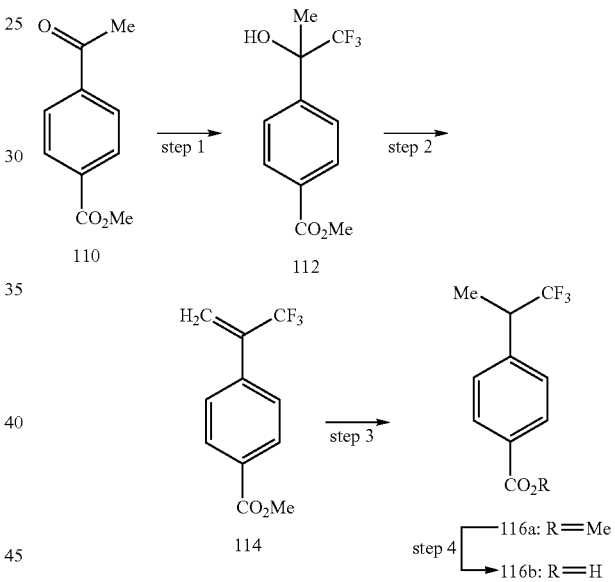

step 1—To a solution of 110 (4 g, 22.4 mmol) in THF (120 mL) was added trimethyl-trifluoromethyl-silane (9.5 g, 67 mmol). The mixture was cooled to 0° C. and a solution of tetrabutylammonium fluoride (67 ml, 66.7 mmol. 1M in THF) was added slowly. The reaction mixture was warmed to RT and stirred for 16 h. The mixture was diluted with EtOAc and washed with brine. The organic layer was dried ($Na_2SO_4$), filtered and concentrated in vacuo. The residue was purified by $SiO_2$ chromatography eluting with a EtOAc/hexane gradient (15% to 35% EtOAc) to afford 5 g (91.7%) of 112.

step 2—To a solution of 112 (1 g, 4 mmol) in THF (6 mL) cooled to 0° C. was added pyridine (0.9 g, 12 mmol) and $SOCl_2$ (1.4 g, 12 mmol) followed by DMAP (20 mg). The mixture was warmed to 50° C. for 2 h with stirring. The reaction mixture was cooled to RT, diluted with EtOAc, washed with brine, dried ($Na_2SO_4$), filtered and concentrated in vacuo. The residue was purified by $SiO_2$ chromatography eluting with a EtOAc/hexane gradient (10% to 30% EtOAc) to afford 0.4 g (43.4%) of 114.

step 3—A suspension of 114(0.150 g, 0.65 mmol) MeOH (50 mL) and 10% Pd/C (20 mg) was stirred under $H_2$ at RT and atmospheric pressure. After 4 h the Pd was filtered and the solvent removed in vacuo to afford 100 mg (66%) of 116a.

step 4-To a solution of 116a (100 mg, 0.43 mmol) and MeOH (4 mL) was added a solution of LiOH monohydrate (65.1 mg, 1.55 mmol) and water (1 mL). The mixture was stirred at RT for 16 h. The reaction mixture was concentrated in vacuo. The residue was dissolved in water (3 mL), acidified to a pH of about 2 with 3N HCl and extracted with EtOAc. The organic layer was dried ($Na_2SO_4$), filtered and concentrated in vacuo to afford 93 mg (99%) of 116b.

II-51 can be prepared analogously to the procedure described in example 25, except in step 4, p-N,N-dimethylamino-benzoyl chloride is replaced with 116b and the coupling of the 116 to 104 is carried out with HATU as described in step 1 of example 21.

EXAMPLE 27

4-tert-Butyl-N-{3-[5-(3-ethyl-ureido)-1-methyl-6-oxo-1,6-dihydro-pyridin-3-yl]-2-hydroxymethyl-phenyl}-benzamide (II-56)

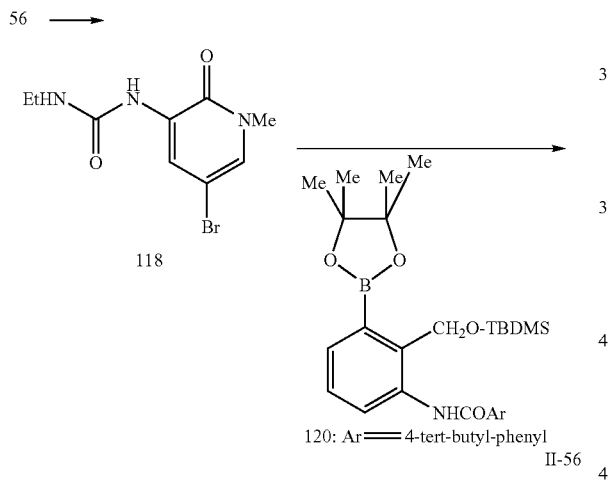

The urea (118) is prepared from 46 by the procedure in step 2 of example 16 except methyl amine was replaced by ethyl amine. The palladium-coupling of 120 and 118 was carried out as described in step 5 of example 25. II-65 is made analogously except the Suzuki coupling is carried out with 120 (Ar=4-(1-fluoro-cyclopropyl)-phenyl).

II-54 can be prepared analogously except 118 is replaced with 1-(5-Bromo-2-oxo-1,2-dihydro-pyridin-3-yl)-3-((S)-2-hydroxy-propyl)-urea which can be prepared from 46 and (S)-1-amino-propan-2-ol by the procedure described in step 2 of example 16 and the Suzuki coupling is carried out with 120 (Ar=4-cyclopropyl-phenyl).

II-57 was prepared analogously except 120 is replaced by N-[2-( tert-butyl-dimethyl-silanyloxymethyl)-3-(4,4,5,5-tetramethyl-[1,3,2]dioxaborolan-2-yl)-phenyl]-4-cyclopropyl-benzamide (120, Ar=4-cyclopropyl-phenyl).

II-61 was prepared analogously except 120 is replaced by N-[2-( tert-butyl-dimethyl-silanyloxymethyl)-3-(4,4,5,5-tetramethyl-[1,3,2]dioxaborolan-2-yl)-phenyl]-4 -dimethylamino-benzamide (120, Ar=4-dimethylamino-phenyl).

II-64 was prepared analogously except 120 is replaced by N-[2-( tert-butyl-dimethyl-silanyloxymethyl)-3-(4,4,5,5-tetramethyl-[1,3,2]dioxaborolan-2-yl)-phenyl]-4-(1-fluoro-cyclopropyl)-benzamide (120, Ar=1-fluoro-cyclopropyl-phenyl).

II-77 was prepared analogously except 120 is replaced by N-[2-( tert-butyl-dimethyl-silanyloxymethyl)-3-(4,4,5,5-tetramethyl-[1,3,2]dioxaborolan-2-yl)-phenyl]-4 -cyclopropyl-benzamide (120, Ar=cyclopropyl-phenyl). II-78, II-79, II-80, II-83, II-84, I-85 and II-86 were prepared analogously except the requisite ureas were prepared by substituting 2-pyridin-2-yl-ethylamine (CASRN 2706-56-1), 2-pyridin-3-yl-ethylamine (CASRN 20173-24-4), $N^1,N^1$-dimethyl-propane-1,3-diamine (CASRN 109-55-7), 3-morpholin-4-yl-propylamine (CASRN 123-00-2), C-(tetrahydro-furan-2-yl)-methylamine (CASRN 4795-29-3), 1-amino-butan-2-ol (CASRN 13552-21-1) and 1-amino-propan-2-ol respectively for methylamine in the procedure described in step 2 of example 16.

EXAMPLE 28

N-{3-[5-(5-Diethylaminomethyl-pyridin-2-ylamino)-1-methyl-6-oxo-1,6 -dihydro-pyridin-3-yl]-2-hydroxymethyl-phenyl}-4-(1-fluoro-cyclopropyl)-benzamide (II-70)

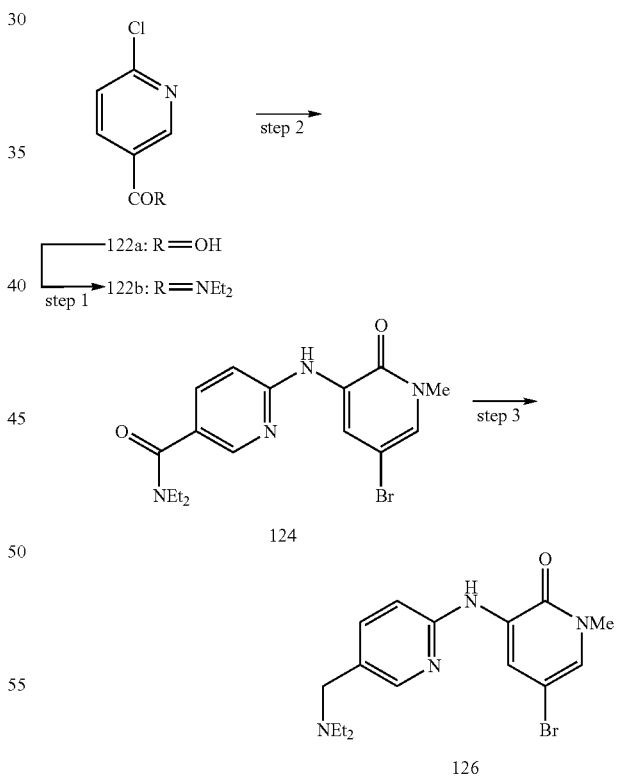

Step 1 was carried out by converting 122a to the corresponding acid chloride which was subsequently contacted with diethyl amine to afford 122b. Treating 3-amino-5-bromo-1-methyl-1H-pyridin-2-one with sodium hydride in DMF as described in step 1 of example 18 and subsequently adding 122b afforded 124 which was reduced to 126 by diborane THF. The palladium-coupling of 126 and 120

(Ar=1-fluoro-cyclopropyl-phenyl) was carried out as described in step 5 of example 25.

EXAMPLE 29

3,3-Dimethyl-2,3-dihydro-benzofuran-6-carboxylic acid (2-hydroxymethyl-3-{1-methyl-5-[5-(morpholine-4-carbonyl)-pyridin-2-ylamino]-6-oxo-1,6-dihydro-pyridin-3-yl}-phenyl)-amide (II-71)

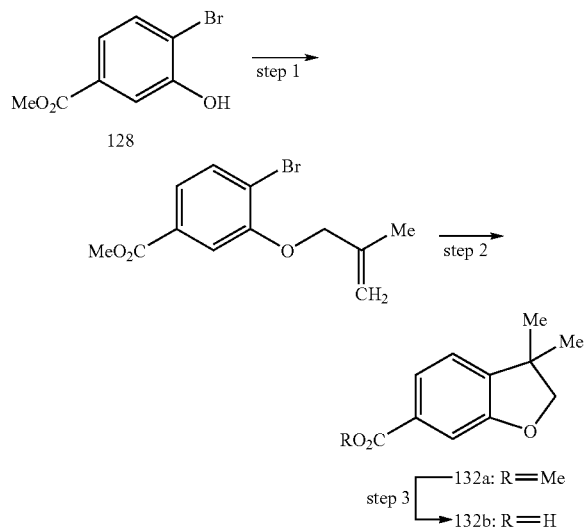

step 1—To a stirred suspension of the 128 (5.01 g, 21.7 mmol) and K$_2$CO$_3$ (4.5 g, 32.5 mmol) in DMF (15 mL) was added dropwise 3-bromo-2-methylpropene (2.93 g, 21.7 mmol) and the resulting suspension was maintained at RT with vigorous stirring overnight. The mixture was diluted with 20% EtOAc/hexanes (100 mL), filtered, and concentrated in vacuo to a clear oil. The residue was purified with SiO$_2$ chromatography eluting with a EtOAc/hexane gradient (0 to 8% EtOAc) to afford 5.8 g (94%) of 130 as a clear oil.

step 2—Solid AIBN (150 mg) was added in one portion to a solution of 130 (2.32 g, 8.14 mmol) and tributyltin hydride (2.84 g, 9.76 mmol) in degassed benzene (75 mL), and the solution was heated at 100° C. under a N$_2$ atmosphere for 32 h. The benzene was removed in vacuo, and the residue was dissolved in Et$_2$O (100 mL). Aqueous KF (10% w/v, 150 mL) was added and the biphasic mixture was vigorously stirred for 3.5 h. The layers were separated and the organic layer was washed sequentially with saturated NaHCO$_3$ (25 mL) and brine (25 mL), dried (MgSO$_4$), filtered and concentrated to a yellow oil. The residue was purified with SiO$_2$ chromatography eluting with a EtOAc/hexane gradient (0 to 8% EtOAc) to afford 1.65 g (99%) of 132a as a clear oil.

step 3—Aqueous LiOH (1 N, 21 mL) was added to a solution of 132a (1.45 g, 7.03 mmol) in MeOH (42 mL), and the solution was maintained at RT for 4 h. The reaction pH was adjusted to 2.0 by the addition of 2 N HCl, and this suspension was extracted with EtOAc (2×50 mL). The combined organics were washed with brine (25 mL), dried (MgSO$_4$), filtered and concentrated in vacuo to afford 1.34 g (99%) of 132b as a white amorphous solid which was used without further purification.

The preparation of II-71 is then carried out in analogy to the procedures described in example 25, except in step 4, p-N,N-dimethylamino-benzoyl chloride is replaced with 132b and the coupling to 104 was accomplished with HATU as described in step I of example 21.

EXAMPLE 30

4-(1-Difluoromethyl-cyclopropyl)-N-(2-hydroxymethyl-3-{1-methyl-5-[5-(morpholine-4-carbonyl)-pyridin-2-ylamino]-6-oxo-1,6-dihydro-pyridin-3-yl}-phenyl)-benzamide (II-72)

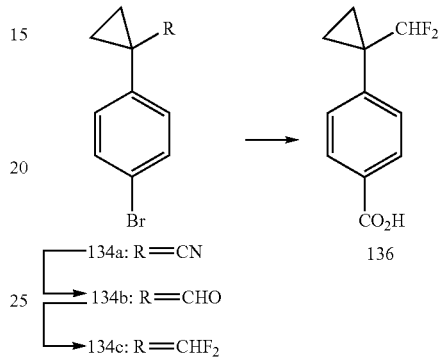

step 1—To a solution of 134a (0.8 g, 3.6 mmol, 124276-67-1) in toluene (8 mL) cooled to −50° C. was added dropwise DIBAH (4.4 mL, 4.4 mmol, 1 M solution in toluene) while maintaining temperature below −40° C. After stirring for 1 h at −40° C. the reaction was quenched with 6 M HCl (3 mL) and stirred at RT for 30 min. The mixture was diluted with EtOAc, the organic layer was separated and washed sequentially with saturated NaHCO$_3$ and brine, dried (Na$_2$SO$_4$), filtered and evaporated to afford 0.67 g (83%) of 134b which was used in the next step without further purification.

step 2—To a solution of 134b (0.56 g, 2.5 mmol) and DCM (6 mL) under a nitrogen atmosphere was added dropwise a solution of DAST (0.40 g, 2.5 mmol) in DCM (1.5 mL). The reaction mixture was stirred at RT for 2 h, then cooled in an ice bath and carefully quenched with ice water (4 mL). The resulting mixture was diluted with EtOAc and the organic phase washed sequentially with saturated NaHCO$_3$ and brine, dried (Na$_2$SO$_4$), filtered and concentrated in vacuo. The residue was purified by SiO$_2$ chromatography eluting with a EtOAc/hexane gradient (0 to 10% EtOAc) to afford 0.208 g (33% yield) of 134c.

step 3—To a solution of n-BuLi and pentane (0.5 mL, 1 mmol, 2M solution) was added THF (8 ml) and the solution was cooled to −78° C. A solution of compound 134c (0.208 g, 0.84 mmol) in THF (1 mL) was added. The mixture was stirred at −78° C. for 20 min and then CO$_2$ gas was bubbled through the solution for 0.5 h. The reaction mixture was warmed to RT, quenched with saturated NH$_4$Cl (4 mL) and extracted with ether. The combined organic extracts were washed with brine, dried (Na$_2$SO$_4$), filtered and concentrated in vacuo. The residue was dissolved in saturated NaHCO$_3$ (10 mL) and extracted with 10% EtOAc in hexane. The aqueous layer was acidified to a pH of about 2 with 3N HCl and the acidified solution extracted with EtOAc. The organic layer was washed with brine, dried (Na$_2$SO$_4$), filtered and concentrated in vacuo to afford 0.040 g (22%) of 136.

The preparation of II-72 is then carried out in analogy to the procedures described in example 25, except in step 4, p-N,N- dimethylamino-benzoyl chloride is replaced with 136 and the coupling to 104 was accomplished with HATU as described in step 1 of example 21.

EXAMPLE 31

N-(2-Hydroxymethyl-3-{1-methyl-5-[5-(morpholine-4-carbonyl)-pyridin-2-ylamino]-6-oxo-1,6-dihydro-pyridin-3-yl}-phenyl)-4-(2,2,2-trifluoro-1,1-dimethyl-ethyl)-benzamide (II-73)

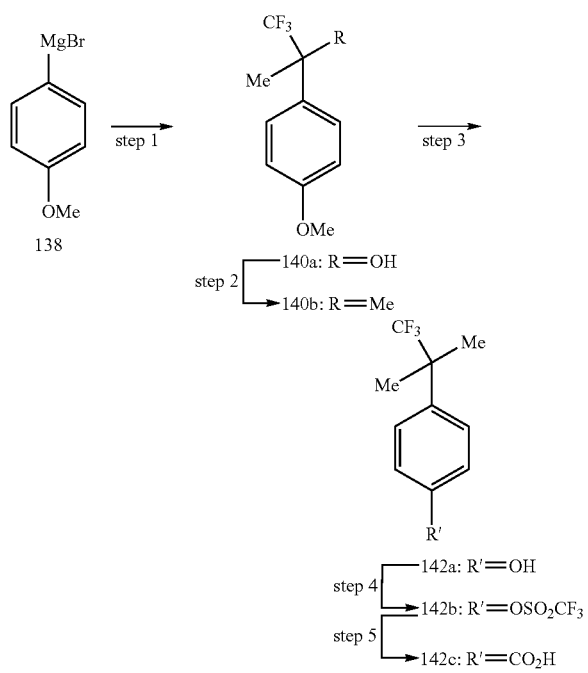

step 1—To a solution of 1.0 M 4-methoxyphenyl magnesium bromide in THF (50 mL) at 0° C. with stirring was added dropwise a solution of 1,1,1-trifluoroacetone (6.11 mL, 1.3 eq) in THF (50 mL). After the addition was completed, the reaction mixture was removed from the ice bath and stirred at RT overnight. The reaction was complete by TLC, and the solution was partitioned between EtOAc (300 mL) and 1M HCl (100 mL) and the mixture was stirred for 10 min. Then the layers were separated and the organic layer was washed with brine (1×100 mL). Finally the EtOAc layer was dried (MgSO4), filtered and concentrated. The crude product was purified by SiO$_2$ chromatography eluting with 5% EtOAc/hexane to afford 2.181 g of 140a as a clear colorless oil.

step 2—To a solution of 140a (2.181 g, 9.90 mmol) in DCM (33 mL) cooled to −78° C. was added TiCl$_4$ (2.17 mL, 2 eq) via syringe and the resulting mixture was stirred at −78° C. for 1.5 h. A solution of dimethylzinc in heptane (39.6 mL, 4 eq, 1.0 M) was added slowly via syringe while maintaining the temperature at −78° C. and the resulting mixture was warmed to RT over about 3.5 h. Finally the reaction mixture was poured into crushed ice (500 g) and stirred vigorously for about 20 min. DCM (300 mL) then was added and the mixture was partitioned and the layers separated. The aqueous layer was extracted with DCM (2×200 ML) and the combined DCM extracts were washed with brine (2×200 mL), dried (MgSO4), filtered and concentrated. The crude product was purified by SiO$_2$ chromatography eluting with a EtOAc/hexane gradient (1% to 5% EtOAc) to afford 1.002 g of 140b as a white powder.

step 3—To a solution of 140b (735 mg, 3.37 mmol) and DCM (50 mL) cooled to −78° C. was added BBr$_3$ (0.955 mL, 3 eq) was added with stirring at −78° C. and the resulting mixture was stirred at −78° C. for 30 min before the dry ice bath was removed and the solution stirred at RT for 3.5 h. TLC analysis indicated that the starting material was entirely consumed. Water (15 mL) was added carefully to the mixture while stirring vigorously followed by 2N NaOH (10 mL) with stirring and then the solution was acidified to pH of about 2 with 4N HCl. The layers were separated and the aqueous layer was further extracted with DCM (2×50 mL) and the combined DCM extracts were washed with brine (1×50mL), dried (MgSO4), filtered and concentrated to afford 0.711 g of 142a as a brownish powder.

step 4—To a solution of 142a (702 mg, 3.44 mmol) in pyridine (3.5 mL) cooled to 0° C. was added dropwise with stirring triflic anhydride (0.64 ml, 1.1 eq) via syringe and the resulting mixture warmed to RT overnight with continued stirring. EtOAc (100 mL) was added and the mixture was washed sequentially with 1M Cu(SO$_4$)$_2$ (4×20 mL), water (2×20 mL) and brine (1×25 mL) and the organic layer was dried (MgSO4), filtered and concentrated. The crude reaction mixture was purified by SiO$_2$ chromatography eluting with a EtOAc/hexane gradient (1% to 3% EtOAc) to afford 0.927 g of 142b as a colorless oil.

step 5—A 5 mL microwave vessel was charged with 142b (410 mg, 1.22 mmol), dppf (68 mg, 0.1 eq), Pd(II)(OAc)$_2$ (28 mg, 0.1 eq), pyridine (0.45 mL), molybdenum hexacarbonyl (161 mg, 0.5 eq) and water (3.9 mL). The sample was irradiated for 20 min at 150° C. then the mixture was partitioned between EtOAc (120 mL) and 4 N HCl. The EtOAc layer was concentrated, 2N NaOH (75 mL) and ether (75 mL) were added, the layers portioned and separated. Finally EtOAc (75 mL) was added and the stirred mixture at 0° C. was acidified to pH of about 2 with concentrated HCl. The EtOAc layer was washed with brine (2×50 mL), dried (MgSO4), filtered and concentrated to afford 0.169 g of 142c as a light tan powder.

The preparation of II-73 is then carried out in analogy to the procedures described in example 25, except in step 4, p-N,N-dimethylamino-benzoyl chloride is replaced with 142c and the coupling to 104 was accomplished with HATU as described in step 1 of example 21.

EXAMPLE 32

4-Cyclopropyl-N-{2-hydroxymethyl-3-[1-methyl-5-(4-methyl-thiazol-2-ylamino)-6-oxo-1,6-dihydro-pyridin-3-yl]-phenyl}-benzamide (II-92)

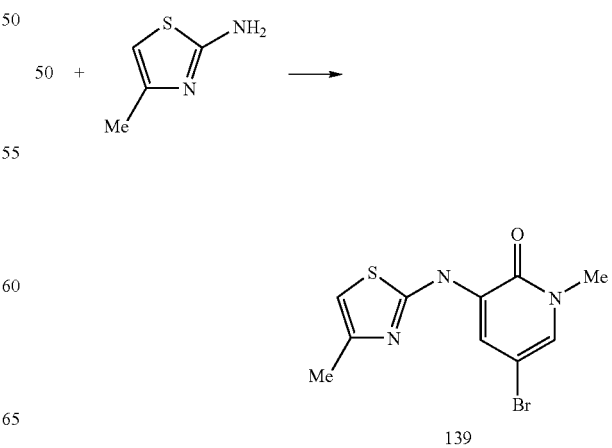

A sealable vial was charged with 50 (0.05 g, 0.19 mmol), 4-methyl-thiazol-2-ylamine (0.03 g, 1.2 eq), Pd(OAc)$_2$ (0.004 g, 0.1 eq), Xantphos (0.02 g, 0.2 eq), and K$_2$CO$_3$ (0.05 g, 2 eq) and 1,4-dioxane (0.5 mL). The argon purged mixture was sealed and heated to 95° C. for 5 h. The cooled reaction was filtered through CELITE, washed with DCM and purified on a preparative SiO$_2$ TLC plate developed with 3% MeOH/DCM to afford 55 mg of 139 as a dark green solid.

The condensation of 139 and 120 (Ar=4-cyclopropyl-phenyl) to afford II-92 was carried out as described in step 5 of example 25

EXAMPLE 33

4-Cyclopropyl-N-(2-hydroxymethyl-3-{1-methyl-5-[6-(4-methyl-piperazin-1-yl)-pyridazin-3-ylamino]-6-oxo-1,6-dihydro-pyridin-3-yl}-phenyl)-benzamide (II-104)

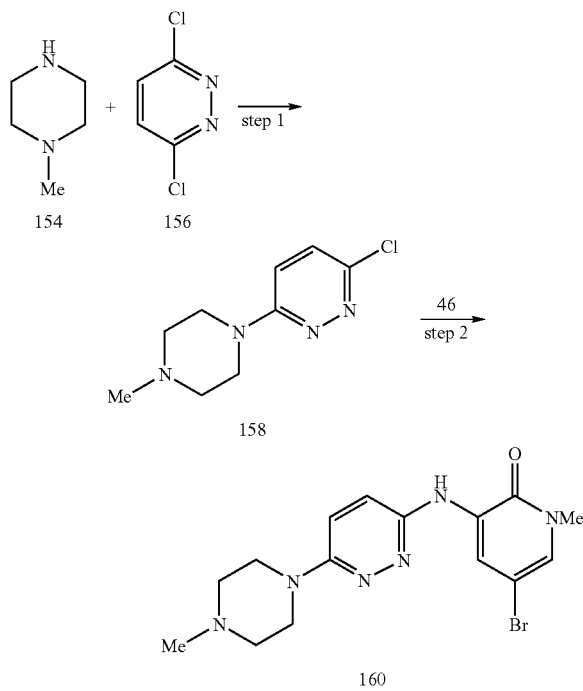

step 1—A mixture of 154 (1.5 g, 15 mmol) and 156 (2.23 g, 15 mmol) in dry toluene (10 mL) was heated in a sealed tube to 110° C. for 3 h. The precipitous mixture was cooled to room temperature dissolved in methanol and dry loaded onto granular SiO$_2$. The crude reaction was purified by SiO$_2$ chromatography eluting with 7% MeOH/DCM to afford 1.3 g of 158 as an off-white solid.

step 2—A heterogeneous mixture of 46 (0.1 g, 0.49 mmol), 158 (0.16 g, 1.5 eq), Pd$_2$(dba)$_3$ (32 mg, 0.07 eq), xantphos (31 mg, 0.1 eq), and Cs$_2$CO$_3$ (0.32 g, 2 eq) in dioxane (1.5 mL) was purged with argon. The mixture was sealed and heated for 18 h in a sand bath at 95° C. The cooled mixture was partitioned between EtOAc and H$_2$O, concentrated, and purified on a preparative SiO$_2$ plate developed with 6% MeOH/DCM to afford 39 mg of 160 as a dark green solid.

Condensation of 160 with D-2 (Ar=4-cyclopropyl-phenyl) was carried out by the procedure in set 5 of example 25.

EXAMPLE 34

Bruton's Tyrosine Kinase (Btk) Inhibition Assay

The assay is a capture of radioactive $^{33}$P phosphorylated product through filtration. The interactions of Btk, biotinylated SH$_2$ peptide substrate (Src homology), and ATP lead to phosphorylation of the peptide substrate. Biotinylated product is bound streptavidin sepharose beads. All bound, radio-labeled products are detected by scintillation counter.

Plates assayed are 96-well polypropylene (Greiner) and 96-well 1.2 μm hydrophilic PVDF filter plates (Millipore). Concentrations reported here are final assay concentrations: 10-100 μM compounds in DMSO (Burdick and Jackson), 5-10 nM Btk enzyme (His-tagged, full-length), 30 μM peptide substrate (Biotin-Aca-AAAEEIYGEI-NH$_2$), 100 μM ATP (Sigma), 8 mM imidazole (Sigma, pH 7.2), 8 mM glycerol-2-phosphate (Sigma), 200 μM EGTA (Roche Diagnostics), 1 mM MnCl$_2$ (Sigma), 20 MM MgCl$_2$ (Sigma), 0.1 mg/ml BSA (Sigma), 2 mM DTT (Sigma), 1 μCi $^{33}$P ATP (Amersham), 20% streptavidin sepharose beads (Amersham), 50 mM EDTA (Gibco), 2 M NaCl (Gibco), 2 M NaCl w/1% phosphoric acid (Gibco), microscint-20 (Perkin Elmer).

IC$_{50}$ determinations are calculated from 10 data points per compound utilizing data produced from a standard 96-well plate assay template. One control compound and seven unknown inhibitors were tested on each plate and each plate was run twice. Typically, compounds were diluted in half-log starting at 100 μM and ending at 3 nM. The control compound was staurosporine. Background was counted in the absence of peptide substrate. Total activity was determined in the presence of peptide substrate. The following protocol was used to determine Btk inhibition.

1) Sample preparation: The test compounds were diluted at half-log increments in assay buffer (imidazole, glycerol-2-phosphate, EGTA, MnCl$_2$, MgCl$_2$, BSA).

2) Bead preparation
   a.) rinse beads by centrifuging at 500 g
   b.) reconstitute the beads with PBS and EDTA to produce a 20% bead slurry 3) Pre-incubate reaction mix without substrate (assay buffer, DTT, ATP, $^{33}$P ATP) and mix with substrate (assay buffer, DTT, ATP, $^{33}$P ATP, peptide substrate) 30° C. for 15 min.

4) To start assay, pre-incubate 10 μL Btk in enzyme buffer (imidazole, glycerol-2-phosphate, BSA) and 10 μL of test compounds for 10 min at RT.

5) Add 30 μL reaction mixture without or with substrate to Btk and compounds.

6) Incubate 50 μL total assay mix for 30 min at 30° C.

7) Transfer 40 μL of assay to 150 μL bead slurry in filter plate to stop reaction.

8) Wash filter plate after 30 min, with following steps
   a. 3×250 μL NaCl
   b. 3×250 μL NaCl containing 1% phosphoric acid
   c. 1×250 μL H$_2$O 9) Dry plate for 1 h at 65° C. or overnight at RT 10) Add 50 μL microscint-20 and count $^{33}$P cpm on scintillation counter.

Calculate percent activity from raw data in cpm percent activity=(sample−bkg)/(total activity−bkg)×100

Calculate IC$_{50}$ from percent activity, using one-site dose response sigmoidal model $y=A+((B-A)/(1+((x/C)^D)))$ x=cmpd conc, y=% activity, A=min, B=max, C=IC$_{50}$, D=1 (hill slope)

EXAMPLE 35

Inhibition of B-cell Activation—B cell FLIPR assay in Ramos cells

Inhibition of B-cell activation by compounds of the present invention is demonstrated by determining the effect of the test compounds on anti-IgM stimulated B cell responses.

The B cell FLIPR assay is a cell based functional method of determining the effect of potential inhibitors of the intracellular calcium increase from stimulation by an anti-IgM antibody. Ramos cells (human Burkitt's lymphoma cell line. ATCC-No. CRL-1596) were cultivated in Growth Media (described below). One day prior to assay, Ramos cells were resuspended in fresh growth media (same as above) and set at a concentration of $0.5 \times 10^6$/mL in tissue culture flasks. On day of assay, cells are counted and set at a concentration of $1 \times 10^6$/mL1 in growth media supplemented with 1 μM FLUO-3AM (TefLabs Cat-No. 0116, prepared in anhydrous DMSO and 10% Pluronic acid) in a tissue culture flask, and incubated at 37° C. (4% $CO_2$) for one h. To remove extracellular dye, cells were collected by centrifugation (5 min, 1000 rpm), resuspended in FLIPR buffer (described below) at $1 \times 10^6$ cells/mL and then dispensed into 96-well poly-D-lysine coated black/clear plates (BD Cat-No. 356692) at $1 \times 10^5$ cells per well. Test compounds were added at various concentrations ranging from 100 μM to 0.03 μM (7 concentrations, details below), and allowed to incubate with cells for 30 min at RT. Ramos cell $Ca^{2+}$ signaling was stimulated by the addition of 10 μg/mL anti-IgM (Southern Biotech, Cat-No. 2020-01) and measured on a FLIPR (Molecular Devices, captures images of 96 well plates using a CCD camera with an argon laser at 480nM excitation).

Media/Buffers:

Growth Medium: RPMI 1640 medium with L-glutamine (Invitrogen, Cat-No. 61870-010), 10% Fetal Bovine Serum (FBS, Summit Biotechnology Cat-No. FP-100-05); 1 mM Sodium Pyruvate (Invitrogen Cat. No. 11360-070).

FLIPR buffer: HBSS (Invitrogen, Cat-No. 141175-079), 2 mM $CaCl_2$ (Sigma Cat-No. C-4901), HEPES (Invitrogen, Cat-No. 15630-080), 2.5mM Probenecid (Sigma, Cat-No. P-8761), 0.1% BSA (Sigma, Cat-No. A-7906), 11 mM Glucose (Sigma, Cat-No. G-7528)

Compound dilution details:

In order to achieve the highest final assay concentration of 100 μM, 24 μL of 10 mM compound stock solution (made in DMSO) is added directly to 576 μL of FLIPR buffer. The test compounds are diluted in FLIPR Buffer (using Biomek 2000 robotic pipettor) resulting in the following dilution scheme: vehicle, $1.00 \times 10^{-4}$ M, $1.00 \times 10^{-5}$, $3.16 \times 10^{-6}$, $1.00 \times 10^{-6}$, $3.16 \times 10^{-7}$, $1.00 \times 10^{-7}$, $3.16 \times 10^{-8}$.

Assay and Analysis:

Intracellular increases in calcium were reported using a max-min statistic (subtracting the resting baseline from the peak caused by addition of the stimulatory antibody using a Molecular Devices FLIPR control and statistic exporting software. The $IC_{50}$ was determined using a non-linear curve fit (GraphPad Prism software). Representative results are in Table III.

TABLE III

| Compound | Ramos B Cell FLIPR $IC_{50}$ (μM) |
|---|---|
| I-2 | 0.0.0747 |
| I-8 | 0.205 |
| I-32 | 0.032 |
| I-17 | 0.415 |
| II-13 | 0.552 |
| II-48 | 0.222 |
| II-2 | 0.067 |
| II-56 | 0.004 |
| II-58 | 0.015 |

EXAMPLE 36

Rat Collagen-induced Arthritis (rCIA)

On day 0, rats are injected with an emulsion of Bovine Type II Collagen in Incomplete Freund's adjuvant (IFA) is injected intradermally (i.d.) on several locations on the back. A booster injection of collagen emulsion is given around day 7, (i.d.) at the base of the tail or alternative sites on the back. Arthritis is generally observed 12-14 days after the initial collagen injection. Animals may be evaluated for the development of arthritis as described below (Evaluation of arthritis) from day 14 onwards. Animals are dosed with candidate therapeutic agents in a preventive fashion starting at the time of secondary challenge and for the prescribed time (typically 2-3 weeks) and dosing frequency, daily (QD) or twice-daily (BID).

Evaluation of Arthritis:

In both models, developing inflammation of the paws and limb joints is quantified using a scoring system that involves the assessment of the 4 paws following the criteria described below:

Scoring: 1=swelling and/or redness of paw or one digit.

2=swelling in two or more joints.

3=gross swelling of the paw with more than two joints involved.

4=severe arthritis of the entire paw and digits.

Evaluations are made on day 0 for baseline measurement and starting again at the first signs or swelling for up to three times per week until the end of the experiment. The arthritic index for each mouse is obtained by adding the four scores of the individual paws, giving a maximum score of 16 per animal.

EXAMPLE 37

Pharmaceutical compositions of the subject compounds for administration via several routes were prepared as described in this Example.

Composition for Oral Administration (A)

| Ingredient | % wt./wt. |
|---|---|
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

Composition for Oral Administration (B)

| Ingredient | % wt./wt. |
|---|---|
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

Composition for Oral Administration (C)

| Ingredient | % wt./wt. |
|---|---|
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

Parenteral Formulation (D)

| Ingredient | % wt./wt. |
|---|---|
| Active ingredient | 0.25 g |
| Sodium Chloride | qs to make isotonic |
| Water for injection to | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

Suppository Formulation (E)

| Ingredient | % wt./wt. |
|---|---|
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

Topical Formulation (F)

| Ingredient | grams |
|---|---|
| Active compound | 0.2-2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

The features disclosed in the foregoing description, or the following claims expressed in their specific forms or in terms of a means for performing the disclosed function, or a method or process for attaining the disclosed result, as appropriate, may, separately, or in any combination of such features, be utilized for realizing the invention in diverse forms thereof.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

We claim:

1. A compound of formula I wherein:

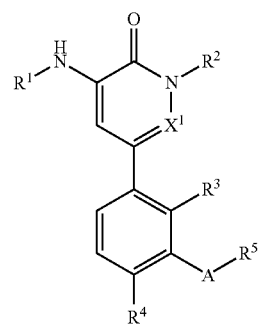

(I)

$X^1$ is N;

$R^I$ is C(=O)NHR$^6$, phenyl or heteroaryl wherein said heteroaryl is selected from the group consisting of pyridinyl, pyridazinyl, pyrimidinyl, pyrazinyl; pyrrolyl, furanyl, thiophenyl, imidazolyl, pyrazolyl, oxazolyl, thiazolyl, isoxazolyl, isothiazolyl, 2-$C_{1-6}$ alkyl-pyridazin-3-on-6-yl, 2-benzyl-pyridazin-3-on-6-yl, 1,4,5, 6-tetrahydro-pyrimidin-2-yl and 4,5-dihydro-1H-imidazol-2-yl;

$R^6$ is hydrogen, $C_{1-6}$alkyl, $C_{1-6}$haloalkyl, $C_{1-6}$heteroalkyl, $C_{3-6}$cycloalkyl, pyridinyl-$C_{1-3}$alkyl, phenyl or phenyl-$C_{1-3}$alkyl said phenyl optionally substituted with $C_{1-6}$alkyl, $C_{1-6}$alkoxy, $C_{1-6}$heteroalkoxy, halogen, CONR$^a$R$^b$, CO$_2$R$^g$.

$R^a$ and $R^b$ (i) selected independently are hydrogen, $C_{1-6}$alkyl, $C_{1-6}$heteroalkyl, $C_{1-3}$ alkoxy-$C_{1-3}$alkyl, carboxy-$C_{1-3}$alkyl, $C_{3-6}$cycloalkyl or heterocyclyl; (ii) together are $(CH_2)_mX^2(CH_2)_2$ wherein m is 2 or 3 and $X^2$ is O, S(O)$_n$ or NR$^8$ and n is zero to two, and R$^8$ is hydrogen, $C_{1-6}$alkyl, $C_{1-6}$hydroxyalkyl or $C_{1-3}$ acyl; or (iii) together with the nitrogen to which they are attached are piperidinyl or pyrrolidinyl said piperidinyl or said pyrrolidinyl optionally substituted with hydroxy, $C_{1-3}$alkoxy, $C_{1-3}$hydroxyalkyl;

R$^g$ is hydrogen or $C_{1-6}$alkyl;

$R^2$ is hydrogen or $C_{1-6}$ alkyl;

$R^3$ and $R^4$ are independently hydrogen, halogen, amino, $C_{1-6}$hydroxyalkyl, $C_{1-6}$alkyl or cyclopropyl;

$R^5$ is (i) phenyl,
(ii) heteroaryl selected from the group consisting of pyridinyl, benzo[b]thiophen-2-yl, 4,5,6,7-tetrahydrobenzo[b]thiophen-2-yl, thiophenyl, 1',2',3',4',5',6'-hexahydro-[2,4']bipyridin-5-yl and $C_{1-3}$alkyl-indolyl optionally substituted with one or two $C_{1-6}$alkyl or halogen;
(iii) azetidin-1-yl, pyrrolidin-2-yl, piperidin-1-yl, azepan-1-yl or 2,3-dihydro-1H-isoindolin-2-yl, or 6,7-dihydro-5H-pyrrolo[3,4-b]pyridine;
(iv) NR$^c$R$^d$ wherein R$^c$ and R$^d$ together are $(CH_2)_oX^2(CH_2)_p$, wherein o and p are independently 1 or 2, and $X^2$ is as defined above, or R$^c$ and R$^d$ independently are hydrogen $C_{1-10}$alkyl or $C_{1-10}$hydroxyalkyl;

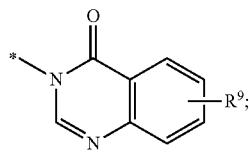 (v)

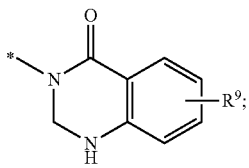 (vi)

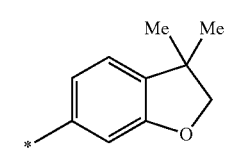 (vii)

wherein R$^9$ is hydrogen, halogen or $C_{1-6}$alkyl;
wherein said phenyl, heteroaryl, azetidin-1-yl, pyrrolidin-2-yl, piperidin-1-yl, azepan-1-yl or 2,3-dihydro-1H-isoindolin-2-yl ring is optionally substituted with one to three groups independently selected from the group consisting of (a) halogen, (b) $C_{1-6}$alkyl, (b) $C_{2-6}$alkenyl, (c) $C_{2-6}$alkynyl, (d) $C_{1-6}$haloalkyl, (e) $C_{1-6}$heteroalkyl, (f) $C_{3-7}$cycloalkyl optionally substituted with one to three groups selected from $C_{1-6}$alkyl, $C_{1-6}$haloalkyl or halogen, (g) $C_{1-6}$alkoxyalkyl, (h) hydroxy, (i) NR$^e$R$^f$, wherein R$^e$ and R$^f$ are (i) independently hydrogen, $C_{1-6}$alkyl or (ii) together are $(CH_2)_mX^3(CH_2)_2$ wherein m is 2 or 3 and $X^3$ is $CH_2$, O, S(O)$_n$ or NR$^8$ and n is zero to two and R$^8$ is as defined above; (j) $C_{1-6}$alkoxy, (k) trialkylsilyl, (l) $C_{1-6}$cyanoalkyl and (m) SF$_5$ A is —NHC(═O)—, C(═O)NH—, NHC(═O)NH, $CH_2C$(═O), $CH_2SO_2$ or R$^5$ is (v) or (vi) A is absent;

or a pharmaceutically acceptable salt thereof.

2. A compound according to claim 1 wherein:
$R^1$ is phenyl, pyridin-2-yl or pyrimidin-4-yl
$R^2$ is $C_{1-3}$ alkyl;
$R^3$ is hydrogen or $C_{1-3}$ alkyl; and,
A is NHC(═O).

3. A compound according to claim 1 wherein:
$R^1$ is phenyl, pyridin-2-yl or pyrimidin-4-yl
$R^2$ is $C_{1-3}$ alkyl;
$R^3$ is hydroxymethyl; and,
A is NHC(═O).

4. A compound according to claim 3 wherein $R^5$ is optionally substituted phenyl, optionally substituted pyridinyl, benzo[b]thiophen-2-yl or 4,5,6,7-tetrahydro-benzo[b]thiophen-2-yl.

5. A compound according claim 1 wherein $R^5$ is (v) or (vi).

6. A compound according claim 1 wherein A is $CH_2C$(═O) and $R^5$ is (i), (ii), (iii) or (iv).

7. A pharmaceutical composition comprising a compound according to claim 1 admixed with at least one pharmaceutically acceptable carrier, excipient or diluent.

8. A compound selected from the group consisting of:
4-tert-Butyl-N-(2-methyl-3-{1-methyl-5-[5-(morpholine-4-carbonyl)-pyridin-2-ylamino]-6-oxo-1,6-dihydro-pyridazin-3-yl}-phenyl)-benzamide;
4-tert-Butyl-N-(2-methyl-3-{1-methyl-5-[5-(4-methyl-piperazine-1-carbonyl)-pyridin-2-ylamino]-6-oxo-1,6-dihydro-pyridazin-3-yl}-phenyl)-benzamide;
4-tert-Butyl-N-{2-methyl-3-[1-methyl-6-oxo-5-(pyridin-2-ylamino)-1,6-dihydro-pyridazin-3-yl]-phenyl}-benzamide;
4-tert-Butyl-N-{2-methyl-3-[1-methyl-6-oxo-5-(pyrimidin-4-ylamino)-1,6-dihydro-pyridazin-3-yl]-phenyl}-benzamide;
4-(1-Hydroxy-1-methyl-ethyl)-N-(2-methyl-3-1-methyl-5-[5-(4-methyl-piperazine-1-carbonyl)-pyridin-2-ylamino]-6-oxo-1,6-dihydro-pyridazin-3-yl}-phenyl)-benzamide;
4-tert-Butyl-piperazine-1-carboxylic acid (2-methyl-3-{1-methyl-5-(morpholine-4-carbonyl)-pyridin-2-ylamino]-6-oxo-1,6-dihydro-pyridazin-3-yl}-phenyl)-amide;
4-tert-Butyl-2-methoxy-N-(2-methyl-3-{1-methyl-5-[5-(morpholine-4-carbonyl)-pyridin-2-ylamino]-6-oxo-1,6-dihydro-pyridazin-3-yl}-phenyl)-benzamide;
7-tert-Butyl-3-(2-methyl-3-1-methyl-5-[5-(morpholine-4-carbonyl)-pyridin-2-ylamino]-6-oxo-1,6-dihydro-pyridazin-3-yl}-phenyl)-3H-quinazolin-4-one,
6-{6-[3-(4-tert-Butyl-benzoylamino)-2-methyl-phenyl]-2-methyl-3-oxo-2,3-dihydro-pyridazin-4-ylamino}-nicotinic acid methyl ester;
3-tert-Butoxy-azetidine-1-carboxylic acid (2-methyl-3-{1-methyl-5-[5-(morpholine-4-carbonyl)-pyridin-2-ylamino]-6-oxo-1,6-dihydro-pyridazin-3-yl}-phenyl)-amide;
4-tert-Butyl-N-(2-methyl-3-{1-methyl-5-[2-(4-methyl-piperazin-1-yl)-pyrimidin-4-ylamino]-6-oxo-1,6-dihydro-pyridazin-3-yl}-phenyl)-benzamide;

4-tert-Butyl-N-{2-methyl-3-[1-methyl-5-(2-methylsulfanyl-pyrimidin-4-ylamino)-6-oxo-1,6-dihydro-pyridazin-3-yl]-phenyl}-benzamide;

4-tert-Butyl-N-{3-[5-(2-methanesulfonyl-pyrimidin-4-ylamino)-1-methyl-6-oxo-1,6-dihydro -pyridazin-3-yl]-2-methyl-phenyl}-benzamide;

4-tert-Butyl-N-{2-methyl-3-[1-methyl-5-(2-morpholin-4-yl-pyrimidin-4-ylamino)-6-oxo-1,6-dihydro-pyridazin-3-yl]-phenyl}-benzamide;

4-(1-Hydroxy-1-methyl-ethyl)-N-(2-methyl-3-{1-methyl - 5-[5-(morpholine-4-carbonyl) -pyridin-2-ylamino]-6-oxo-1,6-dihydro-pyridazin-3-yl}-phenyl)-benzamide;

4-(1-Hydroxy-1-methyl-ethyl)-N-(3-{1-methyl-5-[5-(morpholine-4-carbonyl) -pyridin-2-ylamino]-6-oxo-1,6-dihydro-pyridazin-3-yl}-phenyl)-benzamide;

4-tert-Butyl-N-{3-[5-(2-methoxy-pyrimidin-4-ylamino)-1-methyl-6-oxo-1,6-dihydro -pyridazin-3-yl]-2-methyl-phenyl}-benzamide;

4-tert-Butyl-N-(3-{5-[2-(2-dimethylamino-ethoxy)-pyrimidin-4-ylamino]-1-methyl-6-oxo-1,6-dihydro-pyridazin-3-yl}-2-methyl-phenyl)-benzamide;

4-tert-Butyl-N-(2-methyl-3-{1-methyl-6-oxo-5-[2-(pyrrolidin-3-ylmethoxy)-pyrimidin-4-ylamino]-1,6-dihydro-pyridazin-3-yl}-phenyl)-benzamide;

4-tert-Butyl-N-(3-{5-[2-(3-hydroxymethyl-pyrrolidin-1-yl)-pyrimidin-4-ylamino]-1-methyl-6-oxo-1,6-dihydro-pyridazin-3-yl}-2-methyl-phenyl)-benzamide;

4-tert-Butyl-N-{2-methyl-3-[1-methyl-6-oxo-5-(2-pyrrolidin-1-yl-pyrimidin-4-ylamino)-1,6-dihydro-pyridazin-3-yl]-phenyl}-benzamide;

4-tert-Butyl-N-(3-{5-[2-(3-hydroxy-pyrrolidin-1-yl)-pyrimidin-4-ylamino]-1-methyl-6-oxo-1,6-dihydro-pyridazin-3-yl}-2-methyl-phenyl)-benzamide;

4-tert-Butyl-N-{2-methyl-3-[1-methyl-5-(3-methyl-ureido)-6-oxo-1,6-dihydro-pyridazin-3-yl]-phenyl}-benzamide;

4-tert-Butyl-N-(2-methyl-3-{1-methyl-5-[4-(morpholine-4-carbonyl)-phenylamino]-6-oxo-1,6-dihydro-pyridazin-3-yl}-phenyl)-benzamide;

4-tert-Butyl-N-(3-{1-methyl-5-[5-(morpholine-4-carbonyl)-pyridin-2-ylamino]-6-oxo-1,6-dihydro-pyridazin-3-yl}-phenyl)-benzamide;

4-tert-Butyl-N-(3-{5-[4-(4-hydroxy-piperidine-1-carbonyl)-phenylamino]-1-methyl-6-oxo-1,6-dihydro-pyridazin-3-yl}-2-methyl-phenyl)-benzamide;

4-tert-Butyl-N-{3-[5-ethyl-ureido)-1-methyl-6-oxo-1,6-dihydro-pyridazin-3-2-methyl -phenyl}-benzamide;

4-Dimethylamino-N-(3-{5-[5-(4-hydroxy-piperidine-1-carbonyl)-pyridin-2-ylamino ]-1-methyl-6-oxo-1,6-dihydro-pyridazin-3-yl]-2-methyl-phenyl)-benzamide;

N-(3-Hydroxy-4,4-dimethyl-pentyl)-2-(3-{1-methyl-5-[5-(morpholine-4-carbonyl)-pyridin-2-ylamino]-6-oxo-1,6-dihydro-pyridazin-3-yl}-phenyl)-acetamide;

4-tert-Butyl-2-hydroxy-N-(2-methyl-3-{1-methyl-5-[5-(morpholine-4-carbonyl)-pyridin-2-ylamino]-6-oxo-1,6-dihydro-pyridazin-3-yl}-phenyl)-benzamide;

6-{3-[2-(1,3-Dihydro-isoindol-2-yl)-2-oxo-ethyl]-phenyl}-4-[5-(4-hydroxy -piperidine-1-carbonyl)-pyridin-2-ylamino]-2-methyl-2H-pyridazin-3-one;

7-tert-Butyl-3-(2-methyl-3-{1-methyl-5-[5-(morpholine-4-carbonyl)-pyridin-2-ylamino ]-6-oxo-1,6-dihydro-pyridazin-3-yl}-phenyl)-2,3-dihydro-1H-quinazolin-4-one;

6-{3-[2-(2-Isopropoxy-azetidin-1-yl)-2-oxo-ethyl]-phenyl}-2-methyl-4-[5-(morpholine-4-carbonyl)-pyridin-2-ylamino]-2H-pyridazin-3-one;

6-{3-[2-(4-tert-Butyl-phenyl)-2-oxo-ethyl]-phenyl}-2-methyl-4-[5-(morpholine-4-carbonyl) -pyridin-2-ylamino]-2H-pyridazin-3-one;

6-{3-[2-(4-tert-Butyl-piperazin-1-yl)-2-oxo-ethyl]-phenyl}-2-methyl-4-[5-(morpholine-4-carbonyl)-pyridin-2-ylamino]-2H-pyridazin-3-one;

6-{3-[2-(3-tert-Butoxy-azetidin-1-yl)-2-oxo-ethyl]-phenyl}-2-methyl-4-[5-(morpholine-4-carbonyl)-pyridin-2-ylamino]-2H-pyridazin-3-one;

6-{3-[2-(1,3-Dihydro-isoindol-2-yl)-2-oxo-ethyl]-phenyl}-2-methyl-4-[5-(morpholine-4-carbonyl)-pyridin-2-ylamino]-2H-pyridazin-3-one;

6-{3-[2-(4-Isopropyl-piperazin-1-yl)-2-oxo-ethyl]-phenyl}-2-methyl-4-[5-(morpholine-4-carbonyl)-pyridin-2-ylamino]-2H-pyridazin-3-one;

6-{3-[2-(4-tert-Butyl-piperidin-1-yl)-2-oxo-ethyl]-phenyl}-2-methyl-4-[5-(morpholine-4-carbonyl)-pyridin-2-ylamino]-2H-pyridazin-3-one;

N-(3,3-Dimethyl-butyl)-2-(3-{1-methyl-5-[5-(morpholine-4-carbonyl)-pyridin-2-ylamino ]-6-oxo-1,6-dihydro-pyridazin-3-yl}-phenyl)-acetamide;

6-{3-[2-(4-Acetyl-piperazin-1-yl)-2-oxo-ethyl]-phenyl}-2-methyl-4-[5-(morpholine-4-carbonyl)-pyridin-2-ylamino]-2H-pyridazin-3-one;

4-Cyclopropyl-N-{2-hydroxymethyl-3-[1-methyl-5-(1-methyl-1H-pyrazol-3-ylamino)-6-oxo-1,6-dihydro-pyridazin-3-yl]-phenyl}-benzamide; and , 4-Cyclopropyl-N-(2-hydroxymethyl-3-1-methyl-5-[5-(morpholine-4-carbonyl) -pyridin-2-ylamino]-6-oxo-1,6-dihydro-pyridazin-3-yl}-phenyl)-benzamide.

\* \* \* \* \*

UNITED STATES PATENT AND TRADEMARK OFFICE
CERTIFICATE OF CORRECTION

| | | |
|---|---|---|
| PATENT NO. | : 7,943,618 B2 | Page 1 of 1 |
| APPLICATION NO. | : 12/288730 | |
| DATED | : May 17, 2011 | |
| INVENTOR(S) | : Dewdney et al. | |

It is certified that error appears in the above-identified patent and that said Letters Patent is hereby corrected as shown below:

In column 138, line 49, please insert --[5- -- before "morpholine"; at the end of line 57, please delete "," and insert --.--

In column 139, line 49, please insert --yl]- -- before "2".

In column 140, line 16, please delete "2", second occurrence, and insert --3--.

Signed and Sealed this
Twelfth Day of July, 2011

David J. Kappos
*Director of the United States Patent and Trademark Office*